US012285264B2

(12) United States Patent
Panken et al.

(10) Patent No.: US 12,285,264 B2
(45) Date of Patent: Apr. 29, 2025

(54) DETERMINING COMPOSITE SIGNALS FROM AT LEAST THREE ELECTRODES

(71) Applicant: Covidien LP, Mansfield, MA (US)

(72) Inventors: Eric J. Panken, Edina, MN (US); Philip E. Tracton, Porter Ranch, CA (US); Eric M. Christensen, Gilbert, AZ (US); Richard J. O'Brien, Hugo, MN (US); David A. Anderson, Stanchfield, MN (US); Avram Scheiner, Vadnais Heights, MN (US); Paul G. Krause, Mahtomedi, MN (US); Jonathon E. Giftakis, Maple Grove, MN (US); John Wainwright, Foothill Ranch, CA (US); Andrew J. Ries, Lino Lakes, MN (US); Randal C. Schulhauser, Phoenix, AZ (US); Ekaterina M. Ippolito, Shoreview, MN (US)

(73) Assignee: Covidien LP, Mansfield, MA (US)

( * ) Notice: Subject to any disclaimer, the term of this patent is extended or adjusted under 35 U.S.C. 154(b) by 140 days.

(21) Appl. No.: 17/333,199

(22) Filed: May 28, 2021

(65) Prior Publication Data

US 2022/0061742 A1    Mar. 3, 2022

Related U.S. Application Data

(60) Provisional application No. 63/071,908, filed on Aug. 28, 2020.

(51) Int. Cl.
*A61B 5/00* (2006.01)
*A61B 5/0205* (2006.01)
(Continued)

(52) U.S. Cl.
CPC .......... *A61B 5/4094* (2013.01); *A61B 5/0205* (2013.01); *A61B 5/02108* (2013.01);
(Continued)

(58) Field of Classification Search
CPC ...... A61B 5/4094; A61B 5/0205; A61B 5/726
See application file for complete search history.

(56) References Cited

U.S. PATENT DOCUMENTS

| 5,029,590 A | 7/1991 | Allain et al. |
| 6,505,067 B1 | 1/2003 | Lee et al. |

(Continued)

FOREIGN PATENT DOCUMENTS

| AU | 2014228116 B2 | 1/2019 |
| CN | 108834398 A | 11/2018 |

(Continued)

OTHER PUBLICATIONS

International Search Report and Written Opinion of International Application No. PCT/US2021/047801, dated Jan. 4, 2022, 15 pp.
(Continued)

*Primary Examiner* — James M Kish
*Assistant Examiner* — Laura Hodge
(74) *Attorney, Agent, or Firm* — Shumaker & Sieffert, P.A.

(57) ABSTRACT

In some examples, a device includes at least three electrodes a first pair of electrodes and a second pair of electrodes. The device also includes circuitry configured to generate a first cardiac signal based on a first differential signal received across the first pair, generate a first brain signal based on the first differential signal received across the first pair, generate a second cardiac signal based on a second differential signal received across the second pair, and generate a second brain signal based on the second differential signal received across the second pair. The circuitry is also configured to output a composite cardiac signal based on the first cardiac signal and the second cardiac signal and to output a composite brain signal based on the first brain signal and the second brain signal.

20 Claims, 22 Drawing Sheets

(51) Int. Cl.
    *A61B 5/021*     (2006.01)
    *A61B 5/024*     (2006.01)
    *A61B 5/28*     (2021.01)
    *A61B 5/291*     (2021.01)
    *A61B 5/304*     (2021.01)
    *A61B 5/318*     (2021.01)
    *A61B 5/369*     (2021.01)

(52) U.S. Cl.
    CPC ............ *A61B 5/02416* (2013.01); *A61B 5/28* (2021.01); *A61B 5/291* (2021.01); *A61B 5/304* (2021.01); *A61B 5/318* (2021.01); *A61B 5/369* (2021.01); *A61B 5/6814* (2013.01); *A61B 5/726* (2013.01); *A61B 2562/06* (2013.01)

(56) References Cited

U.S. PATENT DOCUMENTS

| | | | |
|---|---|---|---|
| 6,728,564 B2 | 4/2004 | Laehteenmaeki | |
| 6,961,601 B2 | 11/2005 | Matthews et al. | |
| 7,130,673 B2 | 10/2006 | Tolvanen-Laakso et al. | |
| 7,471,978 B2 | 12/2008 | John et al. | |
| 7,904,144 B2 | 3/2011 | Causevic et al. | |
| 8,323,188 B2* | 12/2012 | Tran | A61B 5/316 |
| | | | 600/300 |
| 8,364,254 B2 | 1/2013 | Jacquin et al. | |
| 8,370,287 B2 | 2/2013 | Snyder | |
| 8,423,145 B2 | 4/2013 | Pless et al. | |
| 8,744,582 B2* | 6/2014 | Wahlstrand | A61N 1/0476 |
| | | | 607/45 |
| 8,862,199 B2 | 10/2014 | Ko et al. | |
| 8,926,509 B2 | 1/2015 | Magar et al. | |
| 9,149,229 B1 | 10/2015 | Tarler | |
| 9,370,313 B2 | 6/2016 | Mcpeck et al. | |
| 9,408,575 B2 | 8/2016 | Bordoley et al. | |
| 9,532,748 B2 | 1/2017 | Denison et al. | |
| 9,579,028 B2 | 2/2017 | Bonmassar et al. | |
| D784,542 S | 4/2017 | Zwierstra et al. | |
| 9,675,264 B2 | 6/2017 | Acquista et al. | |
| 9,878,160 B2 | 1/2018 | Pless et al. | |
| 9,943,690 B2 | 4/2018 | Pless et al. | |
| 10,182,723 B2 | 1/2019 | Evans et al. | |
| 10,195,402 B2 | 2/2019 | Zhadkevich | |
| 10,244,949 B2* | 4/2019 | Moyer | A61B 5/282 |
| 10,252,058 B1 | 4/2019 | Fuerst | |
| 10,281,478 B2 | 5/2019 | Franco | |
| 10,285,606 B2 | 5/2019 | Jensen | |
| 10,285,617 B2 | 5/2019 | Toth et al. | |
| 10,335,083 B2 | 7/2019 | Keteyian et al. | |
| 10,398,319 B2 | 9/2019 | Wang et al. | |
| 10,463,271 B2 | 11/2019 | Intrator | |
| 10,555,861 B2 | 2/2020 | Zwierstra et al. | |
| 10,575,741 B2 | 3/2020 | Kim et al. | |
| 10,575,818 B2 | 3/2020 | O'Brien et al. | |
| 10,610,200 B2 | 4/2020 | Arant et al. | |
| 10,616,473 B2 | 4/2020 | Costa et al. | |
| 10,617,388 B2 | 4/2020 | Flores, II et al. | |
| 10,743,809 B1 | 8/2020 | Kamousi et al. | |
| 10,779,747 B2 | 9/2020 | Simon | |
| 10,786,209 B2 | 9/2020 | Park et al. | |
| 11,006,841 B2 | 5/2021 | Wainwright et al. | |
| 11,399,761 B2 | 8/2022 | Intrator | |
| 11,457,866 B2 | 10/2022 | Kesinger et al. | |
| 2002/0002390 A1 | 1/2002 | Fischell et al. | |
| 2002/0099412 A1 | 7/2002 | Fischell et al. | |
| 2002/0169485 A1 | 11/2002 | Pless et al. | |
| 2002/0193670 A1* | 12/2002 | Garfield | A61B 5/344 |
| | | | 600/304 |
| 2005/0119708 A1 | 6/2005 | Haefner | |
| 2005/0203366 A1 | 9/2005 | Donoghue et al. | |
| 2006/0235322 A1 | 10/2006 | Simske et al. | |
| 2007/0032736 A1 | 2/2007 | Finnigan et al. | |
| 2007/0239060 A1 | 10/2007 | Giftakis et al. | |
| 2008/0091090 A1 | 4/2008 | Guillory et al. | |
| 2008/0208074 A1 | 8/2008 | Snyder et al. | |
| 2009/0082691 A1* | 3/2009 | Denison | A61B 5/30 |
| | | | 600/544 |
| 2009/0247894 A1 | 10/2009 | Causevic | |
| 2010/0274152 A1 | 10/2010 | Mcpeck et al. | |
| 2010/0317958 A1* | 12/2010 | Beck | A61B 5/316 |
| | | | 600/391 |
| 2011/0093042 A1* | 4/2011 | Torgerson | A61N 1/37247 |
| | | | 607/66 |
| 2011/0125215 A1* | 5/2011 | Goetz | A61N 1/36017 |
| | | | 607/45 |
| 2011/0245707 A1 | 10/2011 | Castle et al. | |
| 2012/0245439 A1* | 9/2012 | Andre | A61B 5/0022 |
| | | | 600/595 |
| 2016/0256130 A1 | 9/2016 | Hamilton et al. | |
| 2016/0278736 A1 | 9/2016 | Hamilton et al. | |
| 2016/0367217 A1 | 12/2016 | Flores, II et al. | |
| 2017/0055839 A1 | 3/2017 | Levinson et al. | |
| 2017/0119347 A1 | 5/2017 | Flores, II et al. | |
| 2017/0127946 A1 | 5/2017 | Levinson et al. | |
| 2017/0188993 A1 | 7/2017 | Hamilton et al. | |
| 2017/0307420 A1 | 10/2017 | Flores, II et al. | |
| 2017/0319099 A1 | 11/2017 | Levinson et al. | |
| 2018/0021021 A1 | 1/2018 | Zwierstra et al. | |
| 2018/0064364 A1 | 3/2018 | Oziel et al. | |
| 2018/0078771 A1* | 3/2018 | Koop | A61B 5/076 |
| 2018/0103927 A1 | 4/2018 | Chung et al. | |
| 2018/0117331 A1 | 5/2018 | Kuzniecky et al. | |
| 2018/0153460 A1* | 6/2018 | Ternes | A61B 5/4094 |
| 2018/0220919 A1 | 8/2018 | Wershing et al. | |
| 2018/0220991 A1 | 8/2018 | O'brien et al. | |
| 2018/0249967 A1 | 9/2018 | Lederman et al. | |
| 2019/0021627 A1 | 1/2019 | Levinson et al. | |
| 2019/0051409 A1 | 2/2019 | Petrossian et al. | |
| 2019/0059850 A1 | 2/2019 | Zwierstra et al. | |
| 2019/0099132 A1 | 4/2019 | Mulinti et al. | |
| 2019/0167139 A1* | 6/2019 | Bardy | A61B 5/287 |
| 2019/0175433 A1 | 6/2019 | Zwierstra et al. | |
| 2019/0200954 A1 | 7/2019 | Flores, II et al. | |
| 2019/0209128 A1 | 7/2019 | O'brien et al. | |
| 2019/0209141 A1 | 7/2019 | O'brien et al. | |
| 2019/0216433 A1 | 7/2019 | Hamilton et al. | |
| 2019/0223830 A1 | 7/2019 | Thorpe et al. | |
| 2019/0223837 A1 | 7/2019 | Petrossian et al. | |
| 2019/0282318 A1 | 9/2019 | Arant et al. | |
| 2019/0307348 A1* | 10/2019 | Govari | A61B 5/30 |
| 2019/0357845 A1 | 11/2019 | Willis et al. | |
| 2019/0365274 A1 | 12/2019 | Wyeth et al. | |
| 2020/0008697 A1 | 1/2020 | Kesinger et al. | |
| 2020/0085255 A1 | 3/2020 | Yoo et al. | |
| 2020/0085525 A1 | 3/2020 | Zwierstra et al. | |
| 2020/0100974 A1 | 4/2020 | Hewes et al. | |
| 2020/0107779 A1* | 4/2020 | Yang | A61B 5/25 |
| 2020/0211713 A1* | 7/2020 | Shadforth | G06T 15/08 |
| 2021/0030299 A1 | 2/2021 | Naber et al. | |
| 2021/0241908 A1 | 8/2021 | Ciupa et al. | |
| 2021/0251497 A1 | 8/2021 | Schulhauser et al. | |
| 2021/0251578 A1 | 8/2021 | Schulhauser et al. | |
| 2021/0259621 A1 | 8/2021 | Alves et al. | |
| 2021/0267465 A1 | 9/2021 | Wainwright et al. | |
| 2021/0378582 A1 | 12/2021 | Day et al. | |
| 2022/0022800 A1 | 1/2022 | Abrams et al. | |
| 2022/0061678 A1 | 3/2022 | Schulhauser et al. | |
| 2022/0061742 A1 | 3/2022 | Panken et al. | |
| 2022/0071547 A1 | 3/2022 | Revels et al. | |
| 2022/0183633 A1 | 6/2022 | Kinzie et al. | |
| 2022/0203091 A1 | 6/2022 | Vysokov | |
| 2022/0296174 A1 | 9/2022 | Kinzie et al. | |

FOREIGN PATENT DOCUMENTS

| | | | | |
|---|---|---|---|---|
| DE | 102014100133 B4 | 8/2016 | | |
| EP | 1357833 B1 | 11/2001 | | |
| EP | 3068294 A1 | 9/2016 | | |
| EP | 3181036 A1 * | 6/2017 | ........... | A61B 5/0205 |
| JP | 2020511173 A | 4/2020 | | |
| WO | 2012151498 A2 | 11/2012 | | |
| WO | 2013110001 A1 | 7/2013 | | |
| WO | 2015048514 A1 | 4/2015 | | |

(56) References Cited

FOREIGN PATENT DOCUMENTS

| WO | 2015073903 | A1 | | 5/2015 | | |
| WO | 2016036946 | A1 | | 3/2016 | | |
| WO | 2016207862 | A1 | | 12/2016 | | |
| WO | 2017120382 | A1 | | 7/2017 | | |
| WO | 2017189623 | A1 | | 11/2017 | | |
| WO | 2018089035 | A1 | | 5/2018 | | |
| WO | WO-2018094720 | A1 | * | 5/2018 | ............... | A61F 2/72 |
| WO | 2019004710 | A1 | | 1/2019 | | |
| WO | 2019094877 | A1 | | 5/2019 | | |
| WO | 2019166557 | A1 | | 9/2019 | | |
| WO | 2019177630 | A1 | | 9/2019 | | |
| WO | 2019190583 | A1 | | 10/2019 | | |
| WO | 2019199334 | A1 | | 10/2019 | | |
| WO | WO-2019211314 | A1 | * | 11/2019 | ............. | A61B 5/002 |
| WO | 2020144687 | A1 | | 7/2020 | | |
| WO | 2021167988 | A1 | | 8/2021 | | |
| WO | 2021181395 | A1 | | 9/2021 | | |
| WO | 2022011077 | A1 | | 1/2022 | | |
| WO | 2022020339 | A1 | | 1/2022 | | |
| WO | 2022047066 | A1 | | 3/2022 | | |
| WO | 2022047215 | A1 | | 3/2022 | | |
| WO | 2022055948 | A1 | | 3/2022 | | |
| WO | 2022132938 | A1 | | 6/2022 | | |
| WO | 2022170150 | A1 | | 8/2022 | | |

OTHER PUBLICATIONS

Ponciano, et al., "Experimental Study for Determining the Parameters Required for Detecting ECG and EEG Related Diseases During the Timed-Up and Go Test," Citation/Abstract, Aug. 27, 2020, 2 pages.

Thakor, et al., "Applications of Adaptive Filtering to ECG Analysis: Noise Cancellation and Arrhythmia Detection," Transactions on Biomedical Engineering. vol. 18. No. 8. Aug. 1991, 10 pages.

Maddirala, et al. "Separation of Sources From Single-Channel EEG Signals Using Independent Component Analysis," IEEE Transactions on Instrumentation and Measurement, vol. 67, No. 2, Feb. 2018, 12 pages.

Bhimraj et al., "Autonomous noise removal from EEG signals using independent component analysis," Date of Conference Mar. 30-Apr. 2, 2017, 1 page.

Correa, et al., "Noise Removal from EEG Signals in Polisomnographic Records Applying Adaptive Filters in Cascade," Published: Jul. 5, 2011, 45 pages.

Finnigan, et al., "EEG in ischaemic stroke: Quantitative EEG can uniquely inform (sub- )acute prognoses and clinical management," Clinical Neurophysiology 124 (2013) 10-19, 10 pages.

Jas et al., "Autoreject: Automated Artifact Rejection for MEG and EEG Data," Oct. 1, 2017;159: 417-429. 5 pages.

Olkkonen, et al., "EEG noise cancellation by a subspace method based on wavelet decomposition," Published: Nov. 21, 2002, Med Sci Monit, 2002; 8(11): MT199-204, 7 pages.

Rosenberg, et al., "Hearables: feasibility of recording cardiac rhythms from head and in-ear locations," Accepted: Oct. 23, 2017, 13 pages.

Routray, et al., "ECG Artifact Removal of EEG signal using Adaptive Neural Network," 2018 IEEE 13th International Conference on Industrial and Information Systems (ICIIS), 4 pages.

U.S. Appl. No. 17/006,444, by Covidien LP (Inventors: Schulhauser et al.), filed Aug. 28, 2020.

International Preliminary Report on Patentability from International Application No. PCT/US2021/047801 dated Mar. 9, 2023, 9 pp.

* cited by examiner

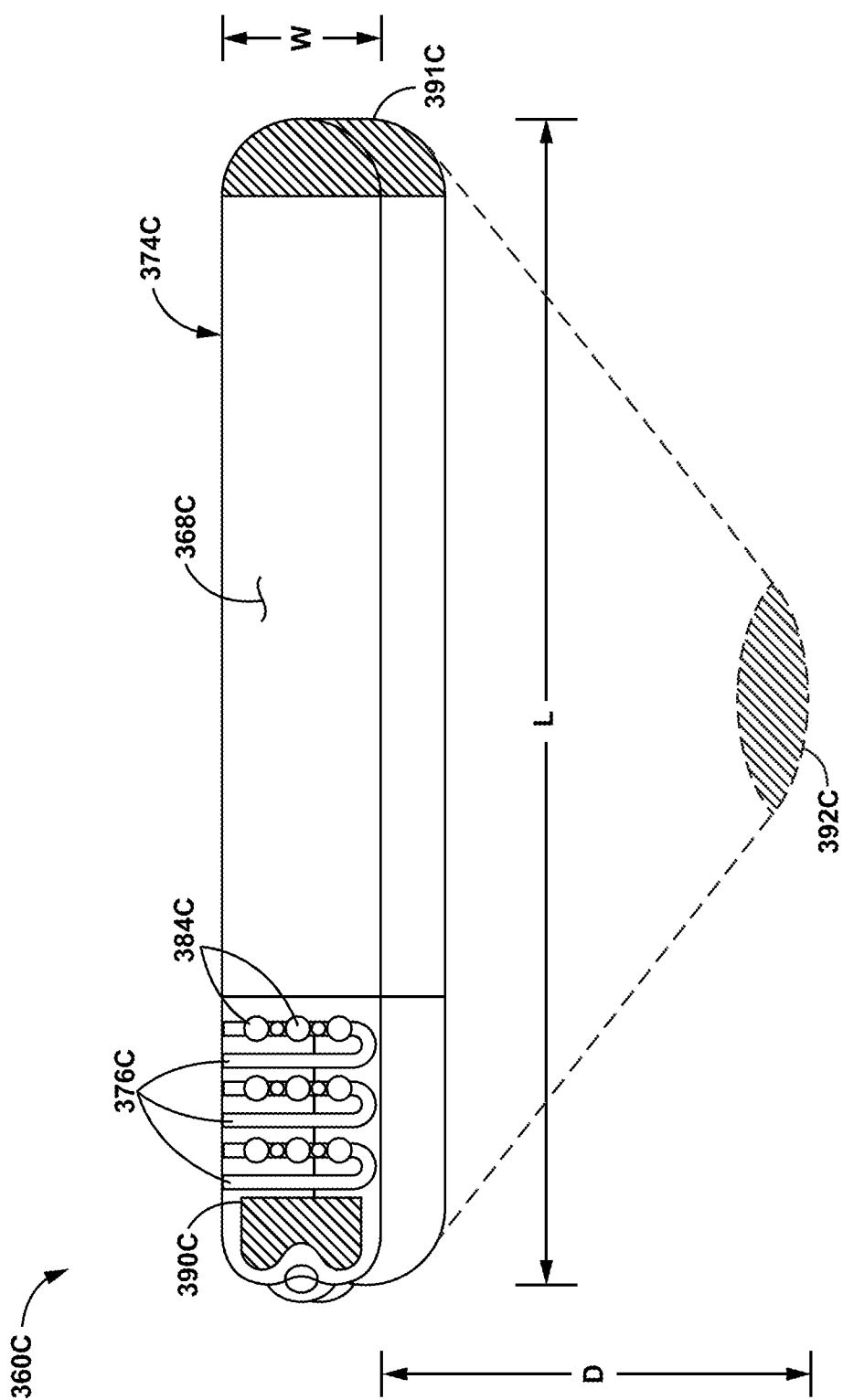

DETERMINING COMPOSITE SIGNALS FROM AT LEAST THREE ELECTRODES

This application claims the benefit of U.S. Provisional Patent Application Ser. No. 63/071,908, filed Aug. 28, 2020, the entire content of which is incorporated herein by reference. In addition, this application is related to U.S. Provisional Patent Application Ser. No. 63/071,828, filed Aug. 28, 2020, and U.S. Provisional Patent Application Ser. No. 63/071,997, filed Aug. 28, 2020, the entire content of which is incorporated herein by reference.

TECHNICAL FIELD

This disclosure is directed to medical devices and, more particularly, to systems and methods for detecting medical conditions such as cardiogenic and neurogenic seizures and stroke.

BACKGROUND

Stroke is a serious medical condition that can cause permanent neurological damage, complications, and death. Stroke may be characterized as the rapidly developing loss of brain functions due to a disturbance in the blood vessels supplying blood to the brain. The loss of brain functions can be a result of ischemia (lack of blood supply) caused by thrombosis, embolism, or hemorrhage (ruptured blood vessel). During a stroke, the blood supply to an area of a brain may be decreased, which can lead to dysfunction of the brain tissue in that area.

Stroke is the number two cause of death worldwide and the number one cause of disability. Speed to treatment is the critical factor in stroke treatment as 1.9 M neurons are lost per minute on average during stroke. Stroke diagnosis and time between event and therapy delivery are the primary barriers to improving therapy effectiveness. Stroke has 3 primary etiologies; i) ischemic stroke (representing approximately 65% of all strokes), ii) hemorrhagic stroke (representing approximately 10% of all strokes), and iii) cryptogenic strokes (includes TIA, representing approximately 25% of all strokes). Strokes can be considered as having neurogenic and/or cardiogenic origins.

A variety of approaches exist for treating patients undergoing a stroke. For example, a clinician may administer anticoagulants, such as warfarin, or may undertake intravascular interventions such as thrombectomy procedures to treat ischemic stroke. As another example, a clinician may administer antihypertensive drugs, such as beta blockers (e.g., Labetalol) and ACE-inhibitors (e.g., Enalapril) or may undertake intravascular interventions such as coil embolization to treat hemorrhagic stroke. Lastly, if stroke symptoms have resolved on their own with negative neurological work-up, a clinician may administer long-term cardiac monitoring (external or implantable) to determine potential cardiac origins of cryptogenic stroke.

Other conditions also affect humans. For example, 65 million people suffer from epilepsy worldwide, with 3.4 million people suffering from epilepsy in the United States. Epilepsy results in approximately 3,400 deaths each year in the United States alone. In some cases, patients may suffer from seizures or other medical conditions that are misdiagnosed as epilepsy. Approximately one out of four patients who are diagnosed with epilepsy are ultimately found to have symptoms caused by a medical condition other than epilepsy. Epileptic patients may also have other conditions, as approximately one quarter of epileptic patients also suffer from cardiac arrhythmias. Treatments for epilepsy may include lifestyle changes and/or drug therapies.

SUMMARY

In general, the disclosure is directed to devices, systems, and techniques for detecting a medical condition, such as cardiogenic and neurogenic seizures and stroke, via a device located internally or externally on a patient. For example, a device may include a plurality of electrodes. The device may be implanted subcutaneously or attached externally in a region of the cranium, such as at the back of the head or the back of the cranium. From this location, the device may be able to record signals from the electrodes carried on the housing. These signals may contain components attributable to brain function and components contributable to cardiac function. The device may process the sensed signals to determine a medical condition of the patient. In some examples, the device may transmit information representative of the medical condition to another device configured to deliver therapy to the patient, such as electrical stimulation therapy and/or drug delivery therapy.

The techniques of this disclosure may provide one or more advantages. For example, it may be beneficial for a single subcutaneously implanted device or externally attached device to be configured to detect a medical condition for the patient. In this manner, the device may screen the patient for potential medical conditions that may inform later treatment.

In one example, a device includes at least three electrodes a first pair of electrodes and a second pair of electrodes; circuitry configured to: generate a first cardiac signal based on a first differential signal received across the first pair; generate a first brain signal based on the first differential signal received across the first pair; generate a second cardiac signal based on a second differential signal received across the second pair; generate a second brain signal based on the second differential signal received across the second pair; output a composite cardiac signal based on the first cardiac signal and the second cardiac signal; and output a composite brain signal based on the first brain signal and the second brain signal.

In some examples, a device includes at least three segmented electrodes including: a first segmented electrode including a first portion and a second portion; a second segmented electrode including a third portion and a fourth portion; and a third segmented electrode including a fifth portion and a sixth portion; and circuitry configured to: generate a first cardiac signal based on a first differential signal received across the first portion and the third portion; generate a first brain signal based on the first differential signal received across the second portion and the fourth portion; generate a second cardiac signal based on a second differential signal received across the first portion and the fifth portion; generate a second brain signal based on the second differential signal received across the second portion and the sixth portion; output a composite cardiac signal based on the first cardiac signal and the second cardiac signal; and output a composite brain signal based on the first brain signal and the second brain signal.

In some examples, a method includes generating a first cardiac signal based on a first differential signal received across a first pair of electrodes; generating a first brain signal based on the first differential signal received across the first pair; generating a second cardiac signal based on a second differential signal received across a second pair of electrodes; generating a second brain signal based on the second differential signal received across the second pair; outputting a composite cardiac signal based on the first cardiac signal and the second cardiac signal; and outputting a composite brain signal based on the first brain signal and the second brain signal.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

FIGS. 3A-3C depict other sensor devices in accordance with embodiments of the present technology.

Figure 1A:
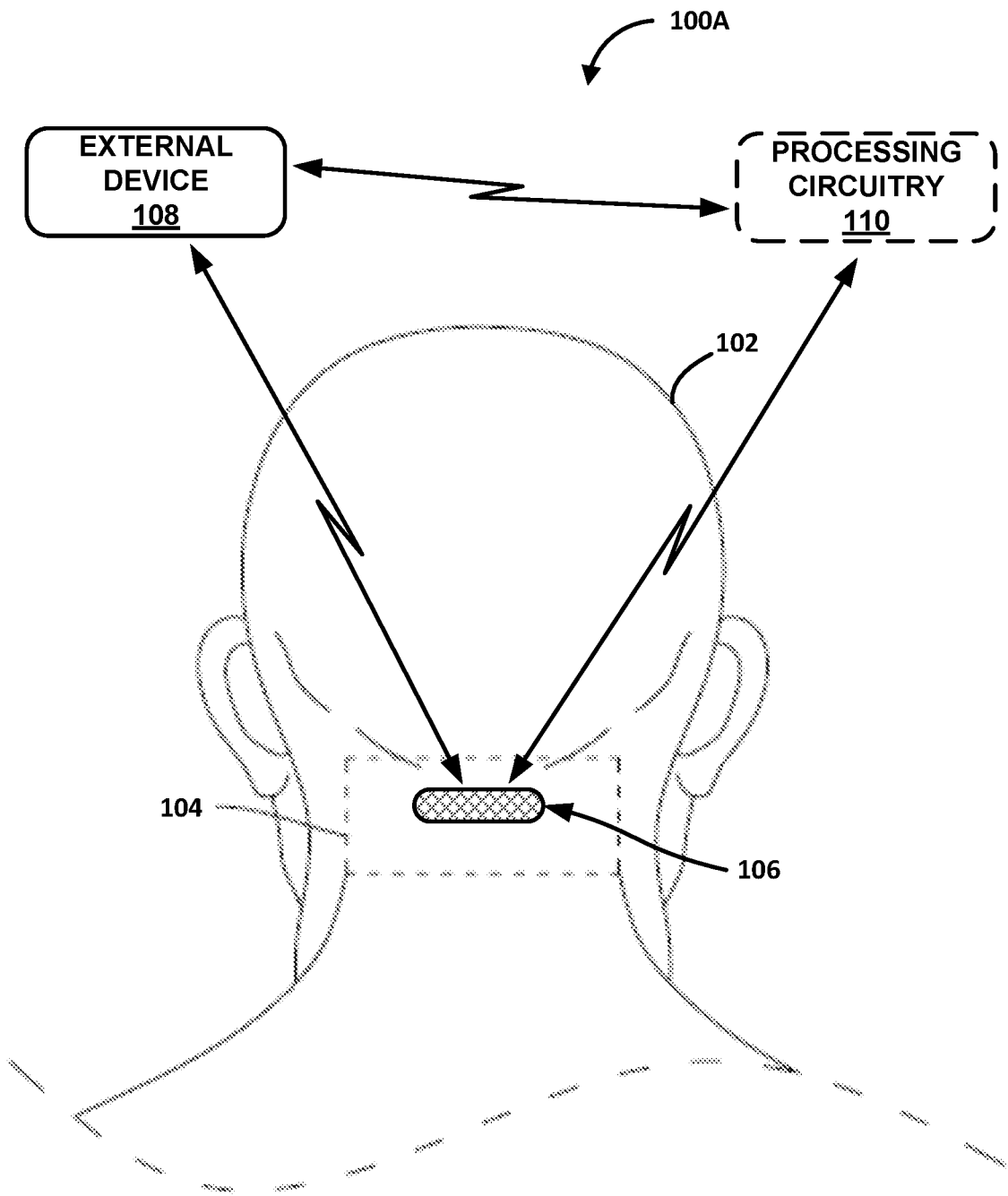
FIG. 1A is a conceptual diagram of a system configured to detect a medical condition in accordance with examples of the present disclosure.

Many aspects of the present disclosure can be better understood with reference to the following drawings. The components in the drawings are not necessarily to scale. Instead, emphasis is placed on clearly illustrating the principles of the present technology.

DETAILED DESCRIPTION

This disclosure describes various systems, devices, and techniques for generating a composite cardiac and brain signals from physiological signals received by at least three electrodes. The composite cardiac and brain signals can be used to diagnose a medical condition such as cardiogenic and neurogenic seizures and stroke. Although this disclosure describes diagnosing seizures and strokes, other medical conditions can be diagnosed such as epilepsy, fainting, cardiac conditions, neurological conditions, and so on.

It can be difficult to determine whether a patient is suffering from a stroke or has suffered from a stroke. Current diagnostic techniques typically involve evaluating a patient for visible symptoms, such as paralysis or numbness of the face, arm, or leg, as well as difficultly walking, speaking, or understanding. For example, visible stroke indicators are abbreviated as F.A.S.T.: face, arm, and speech—time to call 9-1-1. However, these techniques may result in undiagnosed strokes, particularly more minor strokes that leave patients relatively functional upon cursory evaluation. Even for relatively minor strokes, it is important to treat the patient as soon as possible because treatment outcomes for stroke patients are highly time-dependent. Accordingly, there is a need for improved methods for detecting strokes. However, such treatments may be frequently underutilized and/or relatively ineffective due to the failure to timely identify whether a patient is undergoing or has recently undergone a stroke. This is a particular risk with more minor strokes that leave patients relatively functional upon cursory evaluation.

Similarly, it can be difficult to detect or identify seizures, such as seizures that occur in patients with epilepsy. Some patients exhibit physical manifestations of the seizure, such as jerking movements of the arms and legs, other symptoms of a seizure may include temporary confusion, staring, loss of consciousness or awareness, or emotional symptoms such as fear, anxiety, or déjà vu. When patients are experiencing a seizure, the patient may not be able to understand the symptoms or accurately identify what occurred. Moreover, the patient may not be able to obtain or ask for intervention, such as medication. In some examples, a deep brain stimulation (DBS) device may detect seizure and provide electrical stimulation via electrodes implanted within the brain to prevent or reduce symptoms of seizure. However, such DBS devices require an invasive implantation procedure and may not be appropriate for screening or diagnosis of the patient.

As described herein, a device (e.g., implantable device, external device, and/or wearable device) may be configured to detect stroke and seizure from a location on or near the head of the patient. In some examples, the device may be configured to be implanted subcutaneously or positioned externally (e.g., worn) on the patient without the need for any medical leads. In some examples, instead of leads, the device may include a housing that carries multiple electrodes directly on the housing. Using these housing electrodes, the device may sense signals from one or more vectors and generate physiological information representative of patient condition. The physiological information may be indicative of brain activity and/or activity of other organs such as the heart. This physiological information may include stroke information and/or seizure information. For example, different sensing circuits may generate the stroke information and the seizure information such that respective filters and amplifiers may extract the relevant components for stroke and seizure detection, respectively. The device may then generate, from appropriate physiological information, a stroke metric indicative of whether or not the patient has experienced or has a suprathreshold risk of experiencing a stroke and/or a seizure metric indicative of whether or not the patient experienced a seizure or has a suprathreshold risk of experiencing a seizure. In some examples, the device may additionally or alternatively classify a stroke or seizure as one of a plurality of types or strokes or seizures based on the physiological information.

The device may store the stroke metrics and seizure metrics over time. The device may transmit the stroke and seizure metrics to an external device periodically or in response to a trigger event, such as detection of a stroke or seizure being experienced by the patient or prediction that a stroke will be experienced by the patient. In other examples, the device may transmit the stroke and/or seizure metric to another device or external medical device configured to deliver electrical stimulation therapy and/or drug delivery therapy. In some examples, the device may generate the stroke and seizure metrics at different frequencies as needed to provide appropriate monitoring for the patient while conserving power. For example, the device may generate seizure metrics at a higher frequency than the stroke metric because a seizure may only last for a few minutes while characteristics of a stroke may last tens of minutes or even hours. In other examples, the device may trigger the generation of seizure metrics and/or stroke metrics in response to a trigger event that indicates the risk for seizure or stroke has increased, respectively.

Conventional electroencephalogram (EEG) electrodes are typically positioned over a large portion of a patient's scalp. While electrodes in this region are well positioned to detect electrical activity from the patient's brain, there are certain drawbacks. Sensors in this location interfere with patient movement and daily activities, making them impractical for prolonged monitoring. Additionally, implanting traditional electrodes under the patient's scalp is difficult and may lead to significant patient discomfort. To address these and other shortcomings of conventional EEG sensors, embodiments of the present technology include a device configured to record signals at a region near the patient's head, such as adjacent a rear portion of the patient's neck or a rear portion of the patient's skull or near the patient's temple(s). In these positions, implantation under the patient's skin is relatively simple, and a temporary application of a wearable sensor device (e.g., coupled to a bandage, garment, band, or adhesive member) does not unduly interfere with patient movement and activity. Although primarily described in the context of leadless sensor devices, in some examples, e.g., as described with respect to FIGS. 2I-2N, 2P, and 2Q, a sensor device may include electrode extensions to increase a size of a vector for sensing signals via the electrodes, such as brain and cardiac signals, and/or may position electrodes closer to a source of the brain and cardiac signals, which may enhance the sensitivity of algorithms using such signals to detect and/or predict patient conditions.

EEG signals detected via electrodes disposed at or adjacent the back of a patient's neck may include relatively high noise amplitude. For example, the signals associated with brain activity may be intermixed with signals associated with cardiac activity (e.g., electrocardiogram (ECG) signals or signals including components associated with mechanical activity of the heart) and muscle activity (e.g., electromyography (EMG) signals) and artifacts from other electrical sources such as patient movement or external interference. Accordingly, in some embodiments, the sensor data may be filtered or otherwise manipulated to separate the brain activity data (e.g., EEG signals) and cardiac signals (e.g., ECG or other cardiac signals) from each other and other signals (e.g., EMG signals, etc.). A device of this disclosure may include multiple electrodes for sensing differential signals, where circuitry in the device may be configured to generate signals, such as a cardiac signal and a brain signal based on each differential signal.

As described in more detail below, in some embodiments, the physiological information can be analyzed to make a stroke determination or a seizure determination based on one or more thresholds, correlation between signals, or using a classification algorithm, which can itself be derived using machine-learning techniques applied to databases of patient data known to represent the conditions or classifications. The detection algorithm(s) can be passive (involving measurement of a purely resting patient) or active (involving prompting a patient to perform potentially impaired functionality, such as moving particular muscle groups (e.g., raising an arm, moving a finger, moving facial muscles, etc.) and/or speaking while recording the electrical response) or from an electrical signal or other stimulus.

Aspects of the technology described herein can be embodied in a special purpose computer or data processor that is specifically programmed, configured, or constructed to perform one or more of the computer-executable instructions explained in detail herein. Aspects of the technology can also be practiced in distributed computing environments where tasks or modules are performed by remote processing devices, which are linked through a communication network (e.g., a wireless communication network, a wired communication network, a cellular communication network, the Internet, or a short-range radio network (e.g., via Bluetooth)). In a distributed computing environment, program modules may be located in both local and remote memory storage devices.

Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g. a Bluetooth network) on a propagated signal on a propagation medium (e.g., an electromagnetic wave(s), a sound wave) over a period of time, or may be provided on any analog or digital network (packet switched, circuit switched, or other scheme).

FIG. 1A is a conceptual diagram of a system configured to detect stroke or seizure in accordance with examples of the present disclosure. The example techniques described herein may be used with a sensor device 106, which may be in wireless communication with at least one of external device 108, processing circuitry 110, and other devices not pictured in FIG. 1A. For example, an external device (not illustrated in FIG. 1A) may include at least a portion of processing circuitry 110, the external device configured for communication with sensor device 106, and external device 108. Although sensor device 106 is depicted in FIG. 1A, other devices such as an external patch or a wearable device may perform some or all of the techniques described with respect to sensor device 106.

As shown in FIG. 1A, sensor device 106 is located in target region 104. Target region 104 can be a rear portion of a user's neck or a rear portion of the skull. In other examples, target region may be located at other positions of patient, such as near the user's temple(s) (e.g., above the ear(s)) and/or over the temporal portion of the skull. Although sensor device 106 may be implanted at a location generally centered with respect to the head, neck, or target region 104, sensor device 106 may be implanted in an off-center location in order to obtain desired vectors from the electrodes carried on the housing of sensor device 106. Sensor device 106 can be disposed in target region 104 either via implantation (e.g., subcutaneously) or by being placed over the patient's skin with one or more electrodes of sensor device 106 being in direct contact with the patient's skin at or adjacent the target region 104.

While conventional EEG electrodes are placed over the patient's scalp, the present technology advantageously enables recording of clinically useful brain activity data via electrodes positioned at the target region 104 at the rear of the patient's neck or head, or other cranial locations, such as temporal locations, described herein. This anatomical area is well suited to suited both to implantation of sensor device 106 and to temporary placement of a sensor device over the patient's skin. In contrast, conventional EEG electrodes positioned over the scalp are cumbersome, and implantation over the patient's skull is challenging and may introduce significant patient discomfort. As noted elsewhere here, conventional EEG electrodes are typically positioned over the scalp to more readily achieve a suitable signal-to-noise ratio for detection of brain activity. However, by using certain digital signal processing, and a special-purpose classifier algorithm, clinically useful brain activity data can be obtained using sensors disposed at the target region 104. Specifically, the electrodes can detect electrical activity that corresponds to brain activity in the P3, Pz, and/or P4 regions (as shown in FIG. 1C).

While conventional approaches to stroke detection utilizing EEG have relied on data from a large number of EEG electrodes, this disclosure describes that clinically useful stroke and seizure determinations can be made utilizing relatively few electrodes, such as via the electrodes carried by sensor device 106. For example, sensor device 106 may extract features from EEG signals indicative of brain activity or cardiac activity. Sensor device 106 may then determine whether or not the patient has experienced a stroke or seizure based on these extracted features. In some examples, sensor device 106 takes the form of a LINQ™ Insertable Cardiac Monitor (ICM), available from Medtronic plc, of Dublin, Ireland. The example techniques may additionally, or alternatively, be used with a medical device not illustrated in FIG. 1A such as another type of sensor device, a patch monitor device, a wearable device (e.g., smart watch), or another type of external medical device.

Clinicians sometimes diagnose a patient (e.g., patient 102) with medical conditions and/or determine whether a condition of patient 102 is improving or worsening based on one or more observed physiological signals collected by physiological sensors, such as electrodes, optical sensors, chemical sensors, temperature sensors, acoustic sensors, and motion sensors. In some cases, clinicians apply non-invasive sensors to patients in order to sense one or more physiological signals while a patent is in a clinic for a medical appointment. However, in some examples, events that may change a condition of a patient, such as administration of a therapy, may occur outside of the clinic. As such, in these examples, a clinician may be unable to observe the physiological markers needed to determine whether an event, such as a seizure or stroke, has changed a medical condition of the patient and/or determine whether a medical condition of the patient is improving or worsening while monitoring one or more physiological signals of the patient during a medical appointment. In the example illustrated in FIG. 1A, sensor device 106 is implanted within patient 102 to continuously record one or more physiological signals of patient 102 over an extended period of time.

In some examples, sensor device 106 includes a plurality of electrodes. The plurality of electrodes is configured to detect signals that enable processing circuitry of sensor device 106 to determine current values of stroke metrics and seizure metrics associated with the brain and/or cardiovascular functions of patient 102. In some examples, the plurality of electrodes of sensor device 106 are configured to detect a signal indicative of an electric potential of the tissue surrounding the sensor device 106. Moreover, sensor device 106 may additionally or alternatively include one or more optical sensors, accelerometers, impedance sensors, temperature sensors, chemical sensors, light sensors, pressure sensors, and/or acoustic sensors, in some examples. Such sensors may detect one or more physiological parameters indicative of a patient condition.

External device 108 may be a hand-held computing device with a display viewable by the user and an interface for providing input to external device 108 (e.g., a user input mechanism). For example, external device 108 may include a small display screen (e.g., a liquid crystal display (LCD) or a light emitting diode (LED) display) that presents information to the user. In addition, external device 108 may include a touch screen display, keypad, buttons, a peripheral pointing device, voice activation, or another input mechanism that allows the user to navigate through the user interface of external device 108 and provide input. If external device 108 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, external device 108 may be a larger workstation or a separate application within another multi-function device, rather than a dedicated computing device. For example, the multi-function device may be a notebook computer, tablet computer, workstation, one or more servers, cellular phone, smart phone, smart watch or other wearable device, personal digital assistant, or another computing device that may run an application that enables the computing device to operate as a secure device.

When external device 108 is configured for use by the clinician, external device 108 may be used to transmit instructions to sensor device 106. Example instructions may include requests to set electrode combinations for sensing and any other information that may be useful for programming into sensor device 106. The clinician may also configure and store operational parameters for sensor device 106 within sensor device 106 with the aid of external device 108. In some examples, external device 108 assists the clinician in the configuration of sensor device 106 by providing a system for identifying potentially beneficial operational parameter values.

Whether external device 108 is configured for clinician or patient use, external device 108 is configured to communicate with sensor device 106 and, optionally, another computing device (not illustrated by FIG. 1A), via wireless communication. External device 108, for example, may communicate via near-field communication technologies (e.g., inductive coupling, NFC, or other communication technologies operable at ranges less than 10-20 cm) and far-field communication technologies (e.g., RF telemetry according to the 802.11 or Bluetooth® specification sets, or other communication technologies operable at ranges greater than near-field communication technologies). In some examples, external device 108 is configured to communicate with a computer network, such as the Medtronic CareLink® Network developed by Medtronic, plc, of Dublin, Ireland. For example, external device 108 may send data, such as data received from sensor device 106, to another external device such as a smartphone, a tablet, or a desktop computer, and the other external device may in turn send the data to the computer network. In other examples, external device 108 may directly communicate with the computer network without an intermediary device.

Processing circuitry 110, in some examples, may include one or more processors that are configured to implement functionality and/or process instructions for execution within sensor device 106. For example, processing circuitry 110 may be capable of processing instructions stored in a storage device. Processing circuitry 110 may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry 110 may include any suitable structure, whether in hardware, software, firmware, or any combination thereof, to perform the functions ascribed herein to processing circuitry 110.

Processing circuitry 110 may represent processing circuitry located within any one or both of sensor device 106 and external device 108. In some examples, processing circuitry 110 may be entirely located within a housing of sensor device 106. In other examples, processing circuitry 110 may be entirely located within a housing of external device 108. In other examples, processing circuitry 110 may be located within any one or combination of sensor device 106, external device 108, and another device or group of devices that are not illustrated in FIG. 1A. As such, techniques and capabilities attributed herein to processing circuitry 110 may be attributed to any combination of sensor device 106, external device 108, and other devices that are not illustrated in FIG. 1A.

Medical device system 100A of FIG. 1A is an example of a system configured to collect signals and generate stroke metrics and seizure metrics according to one or more techniques of this disclosure. In some examples, processing circuitry 110 includes sensing circuitry configured to generate physiological information from the sensed signal of patient 102. In one example, a signal is sensed via one or more electrode combinations of sensor device 106. A signal is representative of electrical activity of the brain, heart, or other physiological functions as measured by electrodes implanted within the body. For example, the sensed signals may include features representative of heart function such as contractions of the heart, P-waves (depolarization of the atria), R-waves (depolarization of the ventricles), and T-waves (repolarization of the ventricles), among other events. Information relating to the aforementioned events, such as time separating one or more of the events, may be applied for a number of purposes, such as to determine whether an arrhythmia is occurring and/or predict whether an arrhythmia is likely to occur. Cardiac signal analysis circuitry, which may be implemented as part of processing circuitry 110, may perform signal processing techniques to extract information indicating the one or more parameters of the cardiac signal. In other examples, the sensed signals may include features representative of brain function, such as amplitudes of frequencies in one or more frequency bands, such as alpha bands, beta bands, or gamma bands. Brain signal analysis circuitry, which may be implemented as part of processing circuitry 110 may perform various signal processing to extract these brain features from the sensed signals. In some examples, the sensed signals may be surrogates for brain and cardiac electrical signals (e.g., EEG or ECG signals). Pulsatile signals sensed from the scalp vasculature correspond to ventricular contractions and ECG R-waves, albeit with a slight timing delay.

In some examples, processing circuitry 110 may similarly use a comparison of timing between different signals to identify from which hemisphere of the brain a stroke or seizure emanates. For example, a single sensor device with one or more extensions, or bilateral sensor devices, may position electrodes or other sensors to sense signals from each hemisphere of the brain, e.g., from respective temporal locations. Processing circuitry 110 may compare parameter values from the hemispheres to determine from which hemisphere the condition emanates and/or an extend of electrographic spread.

In some examples, processing circuitry 110 may utilize a timing-based evaluation of brain and cardiac signals to discriminate between ischemic and hemorrhagic stroke. For example, processing circuitry 110 may determine whether increases in heart beat variability determined from a cardiac signal precede or follow changes in the brain signal associated with a stroke. Changes in the brain signal may include suppression of frequency and/or amplitude of the signal, or power in one or more frequency bands. Measures of heart beat variability include heart rate variability, intra-beat interval variability (such as QT interval variability), beat feature morphological variability, Lorenz Plot, ST elevation, or T-wave alternans. Changes in heart beat variability following changes in the brain signal may suggest a hemorrhagic stroke, while changes in the brain signal following changes in heart beat variability may suggest an ischemic stroke.

In some examples, sensor device 106 includes one or more accelerometers. An accelerometer of sensor device 106 may collect an accelerometer signal which reflects a measurement of any one or more of a motion of patient 102, a posture of patient 102 and a body angle of patient 102. In some cases, the accelerometer may collect a three-axis accelerometer signal indicative of patient 102's movements within a three-dimensional Cartesian space. For example, the accelerometer signal may include a vertical axis accelerometer signal vector, a lateral axis accelerometer signal vector, and a frontal axis accelerometer signal vector. The vertical axis accelerometer signal vector may represent an acceleration of patient 102 along a vertical axis, the lateral axis accelerometer signal vector may represent an acceleration of patient 102 along a lateral axis, and the frontal axis accelerometer signal vector may represent an acceleration of patient 102 along a frontal axis. In some cases, the vertical axis substantially extends along a torso of patient 102 when patient 102 from a neck of patient 102 to a waist of patient 102, the lateral axis extends across a chest of patient 102 perpendicular to the vertical axis, and the frontal axis extends outward from and through the chest of patient 102, the frontal axis being perpendicular to the vertical axis and the lateral axis.

Sensor device 106 may measure a set of parameters including an impedance (e.g., subcutaneous impedance, an intrathoracic impedance or an intracardiac impedance measured via electrodes depicted in FIGS. 2A-2N, 2P and 2Q) of patient 102, a respiratory rate of patient 102 during night hours, a respiratory rate of patient 102 during day hours, a heart rate of patient 102 during night hours, a heart rate of patient 102 during day hours, an atrial fibrillation (AF) burden of patient 102, a ventricular rate of patient 102 while patient 102 is experiencing AF, or any combination thereof. Processing circuitry 110 may analyze any one or more of the set of parameters in order to determine whether or not the patient is experiencing stroke or seizure, and may indicate an efficacy of a treatment program administered to patient 102. In some examples, the treatment program may include treatment delivered by one or more medical devices such as ICDs with intravascular or extravascular leads, pacemakers, CRT-Ds, neuromodulation devices, LVADs, implantable sensors, orthopedic devices, or drug pumps. Additionally, or alternatively, the treatment program may include in-clinic treatments administered by medical professionals, prescribed pharmaceutical regimens, treatments administered by one or more external medical devices, or any combination thereof. In any case, processing circuitry 110 may determine the efficacy of the treatment program by determining a time in which the treatment program is administered (e.g., including a time in which the treatment program begins and/or a time in which the treatment program ends) and analyzing values of any one or combination of the set of parameters relative to the time in which the treatment program is administered. Alternatively, in some examples, processing circuitry 110 may determine the efficacy of a treatment program by evaluating one or more parameters on a rolling basis in order to determine whether the one or more parameters have changed over a period of time.

In some examples, one or more sensors (e.g., electrodes, motion sensors, optical sensors, temperature sensors, or any combination thereof) of sensor device 106 may generate a signal that indicates a parameter of a patient. In some examples, the signal that indicates the parameter includes a plurality of parameter values, where each parameter value of the plurality of parameter values represents a measurement of the parameter at a respective interval of time. The plurality of parameter values may represent a sequence of parameter values, where each parameter value of the sequence of parameter values are collected by sensor device 106 at a start of each time interval of a sequence of time intervals. For example, sensor device 106 may perform a parameter measurement in order to determine a parameter value of the sequence of parameter values according to a recurring time interval (e.g., every day, every night, every other day, every twelve hours, every hour, or any other recurring time interval). In this way, sensor device 106 may be configured to track a respective patient parameter more effectively as compared with a technique in which a patient parameter is tracked during patient visits to a clinic, since sensor device 106 is implanted within patient 102 and is configured to perform parameter measurements according to recurring time intervals without missing a time interval or performing a parameter measurement off schedule. Processing circuitry 110 may determine these different parameters separately from the seizure or stroke metrics or determine the seizure or stroke metrics based at least partially on one or more other parameter measurements.

Sensor device 106 may be referred to as a system or device. In one example, sensor device 106 may include a memory, a plurality of electrodes carried by the housing of sensor device 106, sensing circuitry configured to sense, via at least two electrodes of the plurality of electrodes, signals from patient 10 and generate, based on the signals, physiological information. Sensor device 106 may also include processing circuitry configured to receive, from the sensing circuitry, the physiological information and determine, based on the physiological information, a seizure metric indicative of a seizure status of the patient and a stroke metric indicative of a stroke status of the patient. The processing circuitry may be configured to then store the seizure metric and the stroke metric in the memory. The housing of sensor device 106 carries the plurality of electrodes and contains, or houses, both of the sensing circuitry and the processing circuitry. In this manner, sensor device 106 may be referred to as a leadless sensing device because the electrodes are carried directly by the housing instead of by any leads that extend from the housing. In some examples, however, sensor device 106 may include one or more sensing leads extending therefrom and into the tissue of the patient. Such lead(s) may be employed instead of or in addition to the electrodes of sensor device 106 (e.g., such as electrode extensions depicted in FIGS. 2I-2N, 2P, and 2Q), and may perform any of the functions attributed herein to the electrodes.

The physiological data can include electrical brain activity data and/or electrical heart activity data. In some examples, the plurality of electrodes are configured to detect brain activity data corresponding to activity in at least one of a P3, Pz, or P4 brain region, which is at the back of the head or upper neck region as shown in FIG. 1C. In this manner, the housing of sensor device 106 may be configured to be disposed at or adjacent a rear portion of a neck or skull of patient 102 or above the ear(s) of patient 102. The housing of sensor device 106 may be configured to be implanted within patient 104, such as implanted subcutaneously. In other examples, the housing of sensor device 106 may be configured to be disposed on an external surface of skin of patient 102.

In some examples, sensor device 106 may include a single sensing circuitry configured to generate, from the sensed signals, information that includes both the brain activity data (e.g., EEG data) and the heart activity data (e.g., ECG data or contraction data). In other examples, the processing circuitry of sensor device 106 may include separate hardware that generates different information from the sensed signals. For example, sensor device 106 may include first circuitry configured to generate the electrical brain activity from the signals and second circuitry different from the first circuitry and configured to generate the electrical heart activity data from the signals. Even with the first and second circuitry configured to generate different information, or data, in some examples, sensed signals may be conditioned or processed by one or more electrical components (e.g., filters or amplifiers) prior to being processed by the first and second circuitry. In some examples, electrical brain activity data may include features, such as spectral features, indicative of the strength of signals in various frequency bands or at various frequencies. In this manner, sensor device 106 may generate a seizure metric based on this electrical brain activity data. In some examples, electrical heart activity data may include features such as the timing and/or amplitude of P-waves, R-waves, or any other features representative of heart function.

Each of the stroke metrics and the seizure metrics may be indicative of the likelihood that patient 102 has experienced, or is experiencing, a stroke or a seizure, respectively. For example, each stroke metric and seizure metric may include a numerical value representative of the probability that patient 102 has experienced a stroke or a seizure. Sensor device 106 may then compare the metric to a respective threshold or monitor a relative change in the metric value over time to determine whether or not a stroke or seizure has occurred. In other examples, the stroke and/or seizure metric may be a binary value that indicates no event occurred or that an event did occur. In some examples, sensor device 106 may generate each stroke metric and/or seizure metric based on sensed data other than the sensed signals from the carried electrodes on the housing of sensor device 106.

In one example, sensor device 106 may include one or more accelerometers within the housing. The accelerometer may be configured to generate motion data representative of motion of patient 102. Sensor device 106 may then be configured to determine, based on the physiological data that includes the motion data, the seizure metric, and the stroke metric. For example, body motion, or lack thereof, may be indicative of a type of seizure experienced by patient 102. As another example, certain body motions or behaviors (e.g., patterns of motion) may be indicative of stroke. In one example, the processing circuitry of sensor device 106 may be configured to determine, based on the motion data, that patient 102 has fallen. In response to determining that patient 102 has fallen, the processing circuitry may be configured to determine, or inform, the stroke metric based on the determination that the patient has fallen. In some examples, stroke may cause a patient to fall. Therefore, in combination with other features extracted from sensed signals, sensor device 106 may determine from the fall indication that the stroke metric indicates detection of a stroke. In other examples, sensor device 106 may determine that a characteristic of the motion data exceeds a threshold. The threshold may be an acceleration value indicative of a fall, for example. Responsive to determining that the characteristic of the motion data exceeds the threshold, the processing circuitry of sensor device 106 may determine at least one of the seizure metric or the stroke metric. For seizure, for example, a frequency of the motion data exceeding a frequency threshold may be indicative of body movement from a seizure.

In some examples, the physiological information generated from the sensed signals may include ECG information. Sensor device 106 may extract various features from the ECG information or from a signal representative of cardiac mechanical activity, such as heart rate, heart rate variability, etc. Sensor device 106 may determine, based on the seizure metric, that patient 102 has experienced a seizure and select, based on the ECG information and from a plurality of seizure types, one seizure type representative of the seizure experienced by the patient. For example, seizure types may include single seizure, stroke induced seizure, epileptic seizure, absence seizures, tonic-clonic or convulsive seizures, atonic seizures, clonic seizures, tonic seizures, and myoclonic seizures. In some examples, sensor device 106 may also determine the seizure type based on accelerometer data, temperature data, or any other parameter extracted from one or more sensors.

Sensor device 106 may generate the seizure metrics and the stroke metrics at the same or different frequencies. In some examples, these frequencies may refer to the frequency at which the sensing circuitry generates appropriate information from which the stroke or seizure metric is determined. In other examples, sensor device 106 may continually generate physiological information from which both stroke and seizure metrics can be determined. However, the frequency may refer to how often the processing circuitry generates the stroke or seizure metric from the physiological information. The seizure detection frequency may be different than the stroke detection frequency due to the duration and/or effects from a seizure or stroke. For example, a seizure may only last for a few minutes, but stroke may last for hours. Therefore, the seizure detection frequency is greater than the stroke detection frequency in some examples. In this manner, timers may be used to trigger the detection of stroke and seizure. Such variation in detection frequency may enable sensor device 106 to conserve power and only monitor for stroke or seizure when appropriate.

In other examples, trigger events for seizure or stroke detection may be identified from various sensed data. For example, the processing circuitry of sensor device 106 may be configured to determine, based on an ECG signal of the physiological information, an arrhythmia of a heart of the patient 102. For some patients, arrhythmias may cause, or be caused by, seizures. Responsive to determining the arrhythmia, sensor device 106 may thus increase a seizure detection frequency that controls determination of the seizure metric and determine the seizure metric according to the seizure detection frequency. In this manner, sensor device 106 may vary the monitoring frequency for seizure based on the presence of any arrythmias in the heart.

Figure 1B:
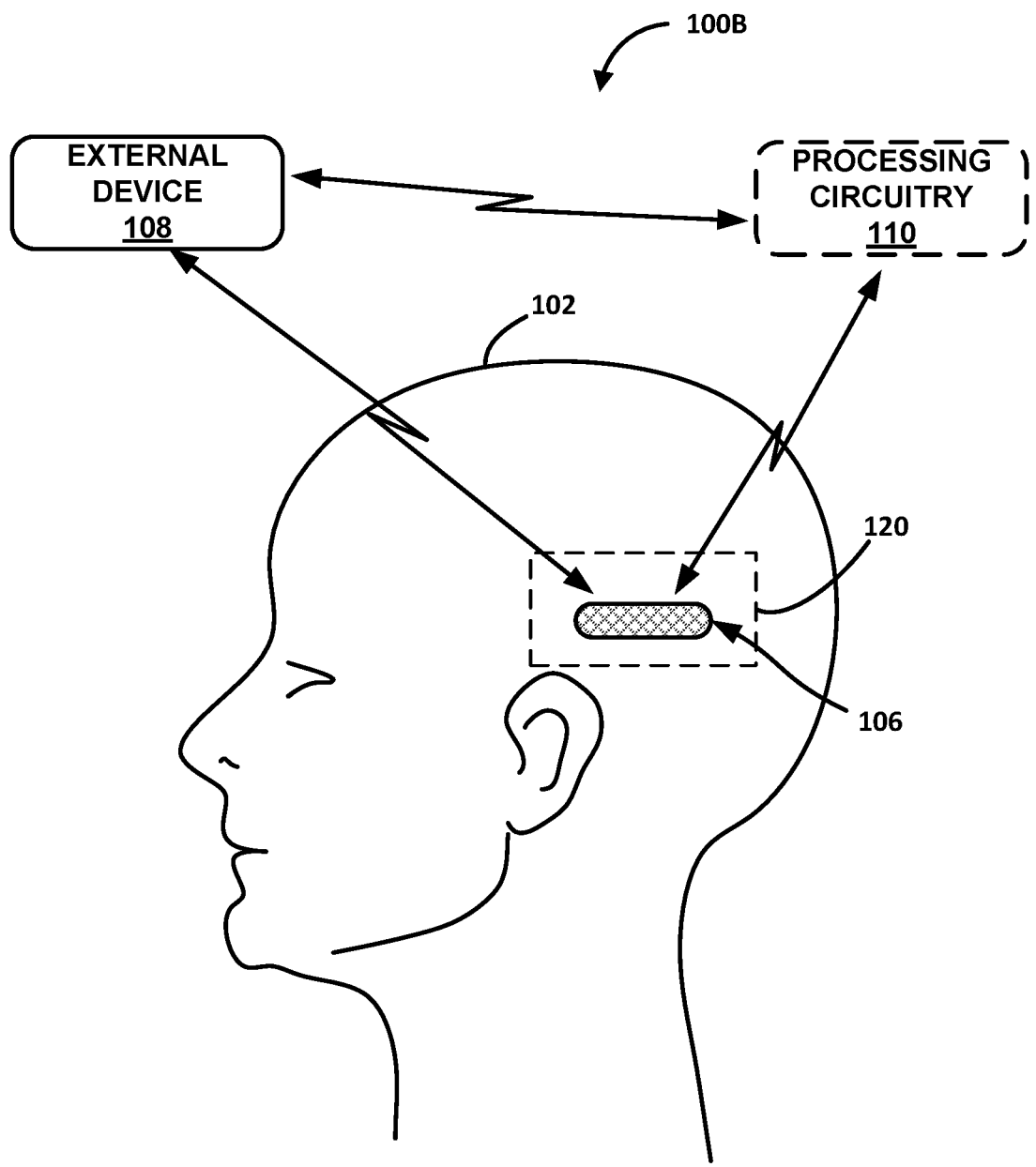
FIG. 1B is a conceptual diagram of a system configured to detect medical condition in accordance with examples of the present disclosure.
Figure 1C:
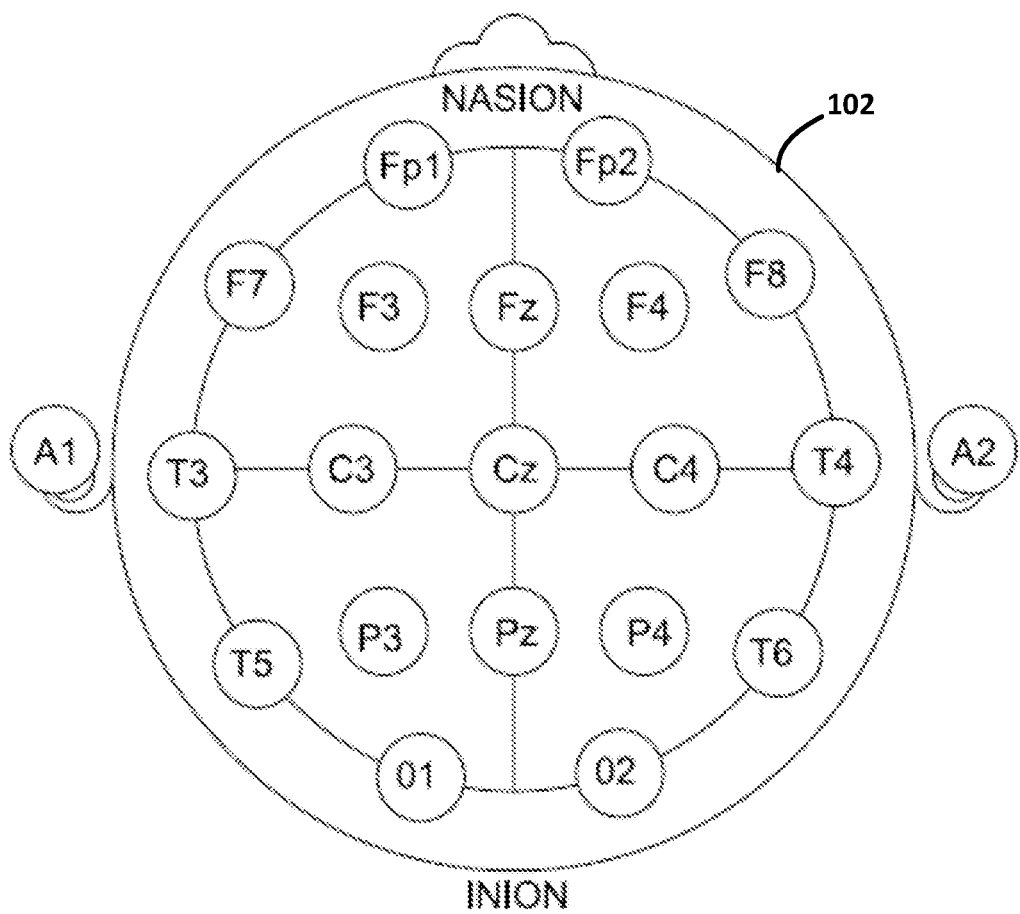
FIG. 1C is a diagram of the 10-20 map for electroencephalography sensor measurements.

FIG. 1B is a conceptual diagram of a system 100B configured to detect stroke or seizure in accordance with examples of the present disclosure. System 100B may be substantially similar to system 100A of FIG. 1A. However, system 100B may be configured to be implanted in target region 120 which is located on the side of the head posterior of the temple of patient 102, e.g., above the ear and/or over the temporal portion of the cranium. Sensor device 106 implanted at target region 120 may be configured to generate stroke metrics and seizure metrics based on signals sensed in this area. In some examples, sensor device 106 may need to employ different filters or other processing or signal conditioning techniques than those at target region 104 due to different types of noise at target region 120, such as muscle activity due to mandible movement or other types of electrical activity. In other examples, sensor device 106 may be configured to determine seizure metrics and stroke metrics from other areas of the head of patient 102 that may be outside of target regions 104 and 120.

FIG. 1C is a diagram of the 10-20 map for EEG sensor measurements. As shown in FIG. 1C, various locations on the head of patient 102 may be targeted using the electrodes carried by sensor device 106. The various locations may include F7, T3, T5, F8, T4, T6, P3, Pz, P4, O1, O2, Fp1, Fp2, A1, A2, C3, Cz, C4, F3, Fz, and/or F4. At the back of the head, such as in target region 104 of FIG. 1A, sensor device 106 may sense signals at one or more of P3, Pz or P4. At the side of the head, such as in target region 120 of FIG. 1B, sensor device 106 may sense signals at one or more of F7, T3, or T5 and/or at one or more of F8, T4, or T6.

Figure 2A:
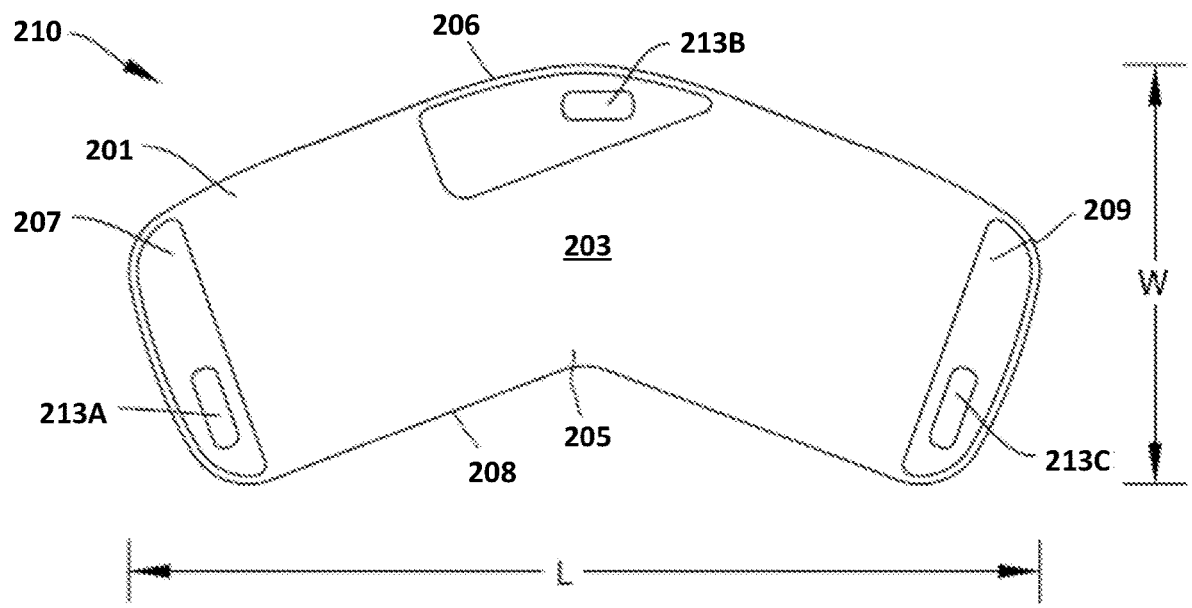
FIGS. 2A, 2C, 2G, and 2H depict top views of devices in accordance with examples of the present disclosure.
Figure 2B:
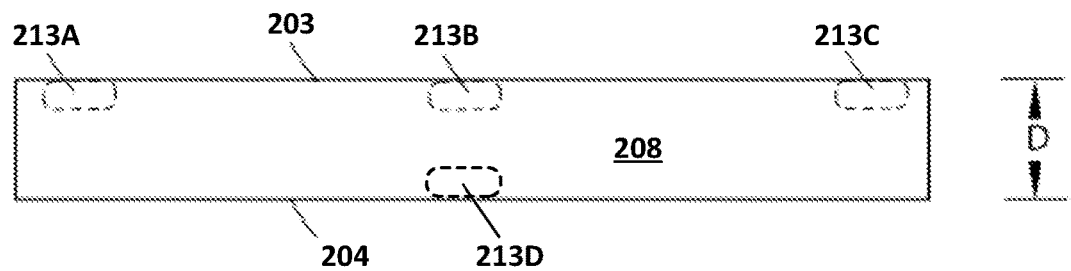
FIGS. 2B and 2D-2F depict side views of devices shown in FIG. 2A in accordance examples of the present disclosure.

FIG. 2A depicts a top view of a sensor device (e.g., an implantable medical device) in accordance with embodiments of the present technology. FIG. 2B depicts a side view of sensor device 210 shown in FIG. 2A in accordance with the present technology. FIG. 2A illustrates a plan view of an example sensor device 210. In some embodiments, the sensor device 210 can include some or all of the features of, and be similar to, sensor device 106 described above with respect to FIGS. 1A and 1B and/or the sensor devices 310, 360B, 360C, or 400 described below with respect to FIGS. 3A-3C and 4, and can include additional features as described in connection with FIG. 2A. In the illustrated example, the sensor device 210 includes a housing 201 that carries a plurality of electrodes 213A, 213B, 213C, and 213D (collectively "electrodes 213") therein. Although four electrodes are shown for sensor device 210, in other examples, only two or three electrodes, or more than four electrodes may be carried by housing 201. As shown in FIG. 2H, any of the electrodes may be segmented; that is, each electrode may include two conductive portions separated by an insulative material. In some examples, a first portion of each electrode may be configured to sense ECG signals or other cardiac signals, and a second portion may be configured to sense EEG signals.

In operation, electrodes 213 can be placed in direct contact with tissue at the target site (e.g., with the user's skin if placed over the user's skin, or with subcutaneous tissue if the sensor device 210 is implanted). Housing 201 additionally encloses electronic circuitry located inside the sensor device 210 and protects the circuitry (e.g., processing circuitry, sensing circuitry, communication circuitry, sensors, and a power source) contained therein from body fluids. In various embodiments, electrodes 213 can be disposed along any surface of the sensor device 210 (e.g., anterior surface, posterior surface, left lateral surface, right lateral surface, superior side surface, inferior side surface, or otherwise), and the surface in turn may take any suitable form.

In the example of FIGS. 2A and 2B, housing 201 can be a biocompatible material having a relatively planar shape including a first major surface 203 configured to face towards the tissue of interest (e.g., to face anteriorly when positioned at the back of the patient's neck) a second major surface 204 opposite the first, and a depth D or thickness of housing 201 extending between the first and second major surfaces. Housing 201 can define a superior side surface 206 (e.g., configured to face superiorly when sensing device 210 is implanted in or at the patient's head or neck) and an opposing inferior side surface 208. Housing 201 can further include a central portion 205, a first lateral portion (or left portion) 207, and a second lateral portion (or right portion) 209. Electrodes 213 are distributed about housing 201 such that a central electrode 213B is disposed within the central portion 205 (e.g., substantially centrally along a horizontal axis of the device), a back electrode 213D is disposed on inferior side surface, a left electrode 213A electrode is disposed within the left portion 207, and a right electrode 213C is disposed within the right portion 209. The arrangement of electrodes 213 in three dimensions may provide for more effective signal discrimination.

As illustrated, housing 201 can define a boomerang or chevron-like shape in which the central portion 205 includes a vertex, with the first and second lateral portions 207 and 209 extending both laterally outward and from the central portion 205 and also at a downward angle with respect to a horizontal axis of the device. In other examples, housing 201 may be formed in other shapes which may be determined by desired distances or angles between different electrodes 213 carried by housing 201.

The configuration of housing 201 can facilitate placement either over the user's skin in a wearable or bandage-like form or for subcutaneous implantation. As such, a relatively thin housing 201 can be advantageous. Additionally, housing 201 can be flexible in some embodiments, so that housing 201 can at least partially bend to correspond to the anatomy of the patient's neck (e.g., with left and right lateral portions 207 and 209 of housing 201 bending anteriorly relative to the central portion 205 of housing 201).

In some embodiments, housing 201 can have a length L of from about 15 to about 50 mm, from about 20 to about 30 mm, or about 25 mm. Housing 201 can have a width W from about 2.5 to about 15 mm, from about 5 to about 10 mm, or about 7.5 mm. In some embodiments, housing 201 can have a thickness of the thickness is less than about 10 mm, about 9 mm, about 8 mm, about 7 mm, about 6 mm, about 5 mm, about 4 mm, or about 3 mm. In some embodiments, the thickness of housing 201 can be from about 2 to about 8 mm, from about 3 to about 5 mm, or about 4 mm. Housing 201 can have a volume of less than about 1.5 cc, about 1.4 cc, about 1.3 cc, about 1.2 cc, about 1.1 cc, about 1.0 cc, about 0.9 cc, about 0.8 cc, about 0.7 cc, about 0.6 cc, about 0.5 cc, or about 0.4 cc. In some embodiments, housing 201 can have dimensions suitable for implantation through a trocar introducer or any other suitable implantation technique.

As illustrated, electrodes 213 carried by housing 201 are arranged so that all three electrodes 213 do not lie on a common axis. In such a configuration, electrodes 213 can achieve a variety of signal vectors, which may provide one or more improved signals, as compared to electrodes that are all aligned along a single axis. This can be particularly useful in a sensor device 210 configured to be implanted at the neck or head while detecting electrical activity in the brain. In some embodiments, this electrode configuration also provides for improved cardiac ECG sensitivity by integrating 3 potential signal vectors. A virtual vector can also be created using a weighted sum of two or more of the physical signal vectors.

In some examples, all of electrodes 213 are located on the first major surface 203 and are substantially flat and outwardly facing. However, in other examples one or more electrodes 213 may utilize a three-dimensional configuration (e.g., curved around an edge of the device 210). Similarly, in other examples, such as that illustrated in FIG. 2B, one or more electrodes 213 may be disposed on the second major surface opposite the first. The various electrode configurations allow for configurations in which electrodes 213 are located on both the first major surface and the second major surface. In other configurations, such as that shown in FIG. 2B, electrodes 213 are only disposed on one of the major surfaces of housing 201. Electrodes 213 may be formed of a plurality of different types of biocompatible conductive material (e.g., stainless steel, titanium, platinum iridium, or alloys thereof), and may utilize one or more coatings such as titanium nitride or fractal titanium nitride. In some embodiments, the material choice for electrodes can also include materials having a high surface area (e.g., to provide better electrode capacitance for better sensitivity) and roughness (e.g., to aid implant stability). Although the example shown in FIGS. 2A and 2B includes four electrodes 213, in some embodiments the sensor device 210 can include 1, 2, 3, 5, 6, or more electrodes carried by housing 201.

Figure 2C:
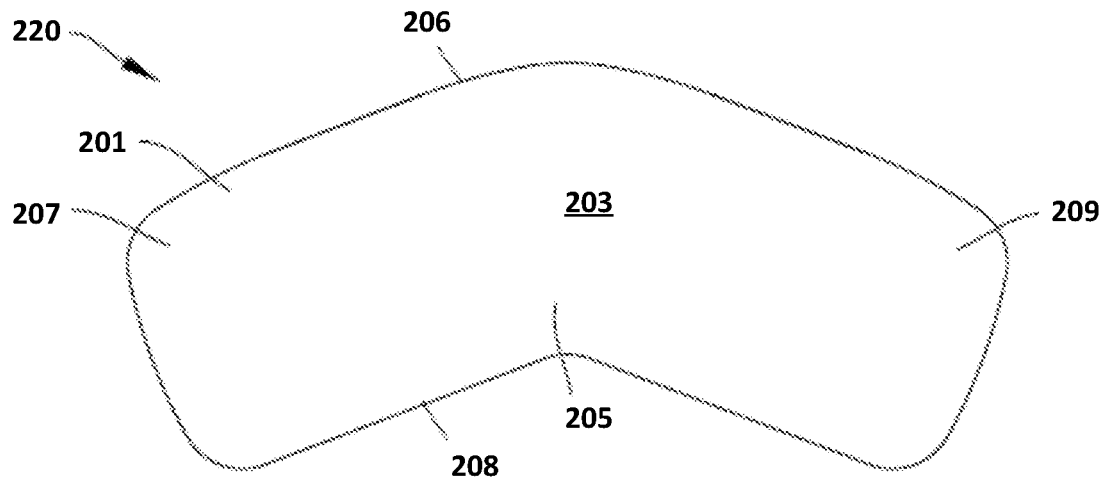
Figure 2D:
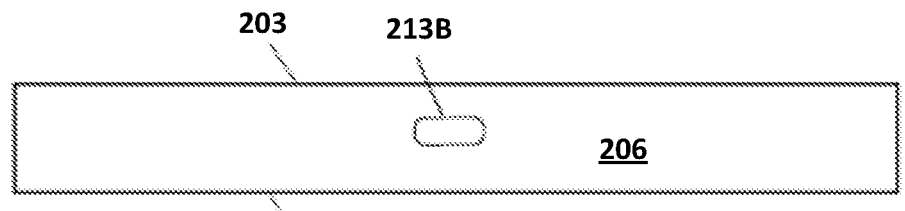
Figure 2E:
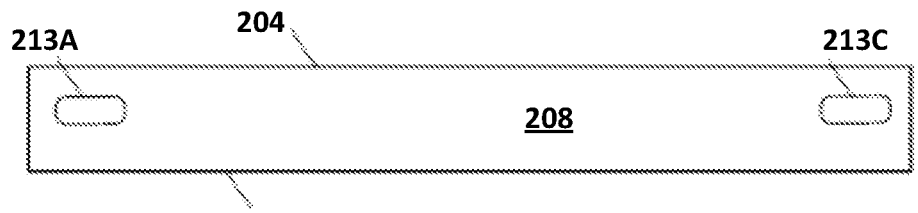
Figure 2F:
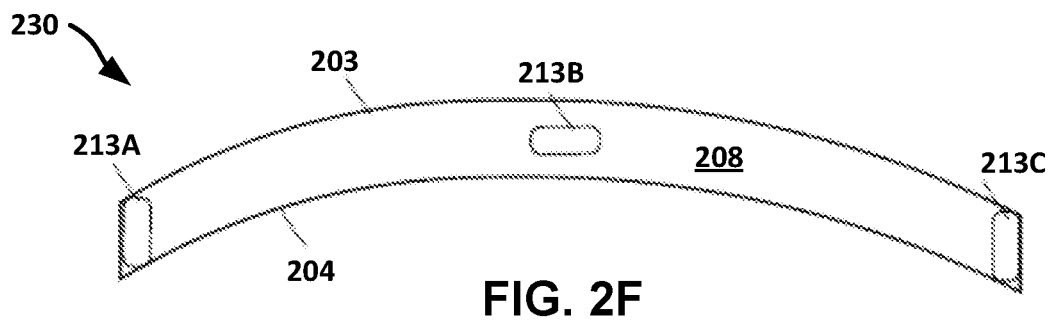

FIG. 2C depicts a top view of another example of sensor device 220 in accordance with the present technology. FIG. 2C illustrates sensor device 220 which is substantially similar to sensor device 210, but sensor device 220 includes electrodes 213 (not shown in FIG. 2C) which are not exposed along the first major surface 203 of housing 201. Instead, electrodes 213 can be exposed along superior and inferior side surfaces (e.g., facing superiorly and inferiorly when implanted at or on a patient's neck), as shown in FIGS. 2D and 2E. FIG. 2F illustrates sensor device 230 which is substantially similar to sensor devices 210 and 220, but housing 201 is constructed to have a curved configuration, and in which the electrodes can be place along the superior and/or inferior side surfaces of housing 201. In some embodiments, a curved configuration can improve patient comfort and more readily conform to the anatomy of the patient's neck region. In some examples, any of sensor devices 210, 220, or 230 may be flexible in order to conform to the anatomy of the patient at the desired implant or external surface location. Additionally, examples that include electrode extensions, e.g., as depicted in FIGS. 2I-2Q, are inherently flexible, allowing conformance to neck and/or cranial anatomy. In some examples, sensor device 220 and/or sensor device 230 may be implanted at a location generally centered with respect to the thorax, the head (e.g., back or temporal regions), neck, or another target region. In some examples, sensor device 220 and/or sensor device 230 may be placed on an external surface of skin of a patient.

In operation, electrodes 213 are used to sense signals (e.g., EEG signals and/or ECG signals) which may be submuscular or subcutaneous. The sensed signals may be stored in a memory of the sensor device 210, and signal data may be transmitted via a communications link to another device (e.g., external device 108 of FIG. 1A). The sensed signals may be time-coded or otherwise correlated with time data, and stored in this form, so that the recency, frequency, time of day, time span, or date(s) of a particular signal data point or data series (or computed measures or statistics based thereon) may be determined and/or reported. In some examples, electrodes 213 may additionally or alternatively be used for sensing any bio-potential signal of interest, such as an ECG, intracardiac electrogram (EGM), EMG, or a nerve signal, from any implanted location. These data may be time-coded or time-correlated, and stored in that form, in the manner described above with respect to EEG signal data.

Figure 2G:
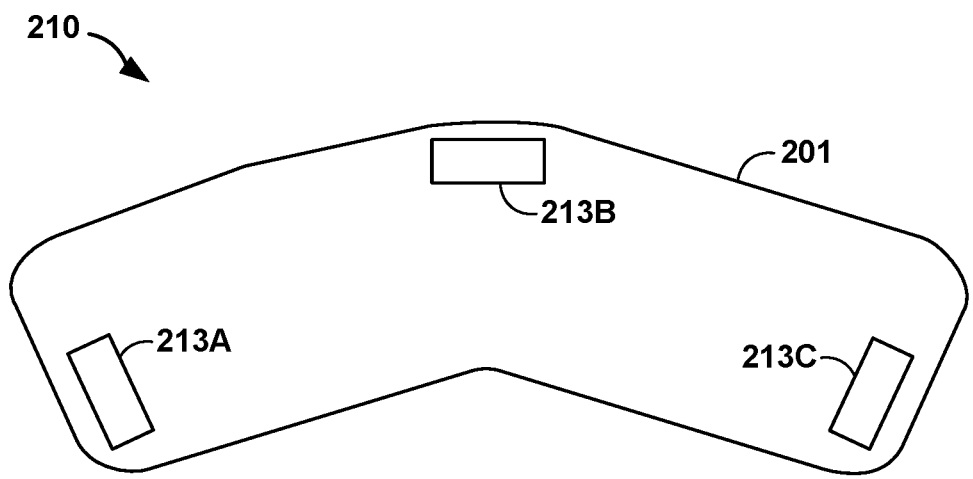
Figure 2H:
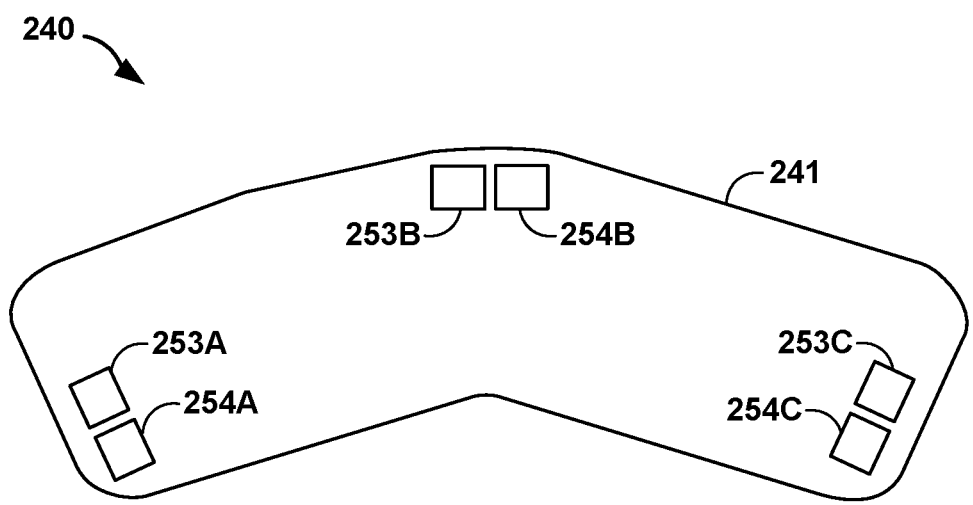

FIGS. 2G and 2H depict top views of devices in accordance with examples of the present disclosure. FIG. 2G depicts housing 201 of sensor device 210, which includes electrodes 213A-213C arranged at the perimeter of housing 201. Each of electrodes 213A-213C may be configured to receive raw signals including cardiac and brain components. Sensor device 210 may include circuitry configured to filter the raw signals received by electrodes 213A-213C to generate cardiac signals and brain signals, e.g., ECG and EEG signals. In some examples, this circuitry may be located outside of sensor device 210.

FIG. 2H depicts housing 241 of sensor device 240, which includes electrodes 253A-253C and 254A-254C. Electrodes 253A and 254A together may be referred to as a segmented electrode. Similarly, electrodes 253B and 254B may be referred to as a segmented electrode, and electrodes 253C and 254C may be referred to as a segmented electrode. Insulative material may separate the conductive portions (e.g., electrodes 253A and 254A) of a segmented electrode.

Circuitry may be configured to generate a first cardiac, e.g., ECG, signal based on a differential signal received at electrodes 253A and 253B, generate a second cardiac signal based on a differential signal received at electrodes 253B and 253C, and/or generate a third cardiac signal based on a differential signal received at electrodes 253C and 253A. Likewise, the circuitry may be configured to generate a first brain signal based on a differential signal received at electrodes 254A and 254B, generate a second brain signal based on a differential signal received at electrodes 254B and 254C, and/or generate a third brain signal based on a differential signal received at electrodes 254C and 254A.

Figure 2I:
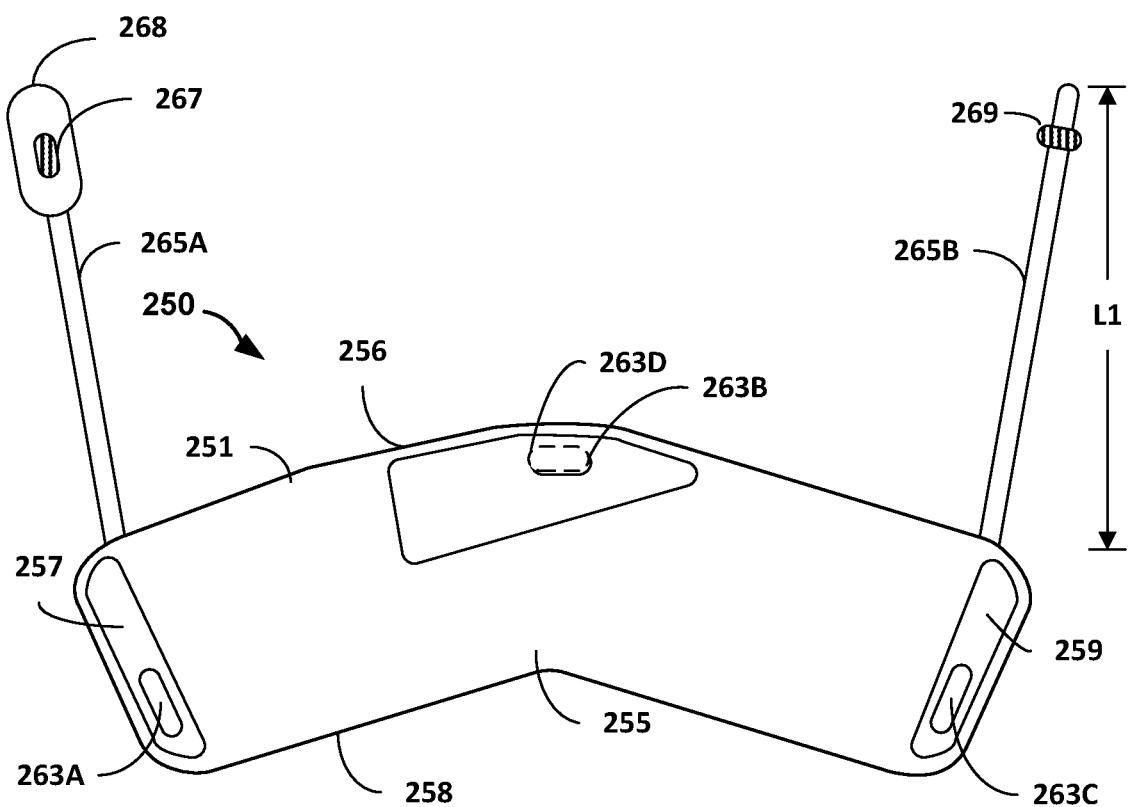
FIG. 2I depicts a top view of another example sensor device that includes electrode extensions in accordance with examples of the present disclosure.

FIG. 2I depicts a top view of another example sensor device 250, which includes electrodes 263A-263D, 267, and 269. Each of electrodes 263A-263D, 267, and 269 may be configured to receive raw signals including cardiac and brain, e.g., ECG and EEG, components. Sensor device 250 may include circuitry configured to filter the raw signals received by electrodes 263A-263D, 267, and 269 to generate cardiac signals and brain signals, e.g., ECG and EEG signals. Sensor device 250 may also include circuitry configured to measure impedance of tissue via electrodes 263A-263D, 267, and 269.

In the example of FIG. 2I, sensor device 250 include a housing 251, which includes a superior side surface 256, an opposing inferior side surface 258, a central portion 255, a first lateral portion (or left portion) 257, and a second lateral portion (or right portion) 259. Electrodes 263 are distributed about housing 251 such that a central electrode 263B is disposed within the central portion 255 (e.g., substantially centrally along a horizontal axis of the device), a left electrode 263A is disposed within the left portion 257, and a right electrode 263C is disposed within the right portion 259.

Sensor device 250 further include electrode extensions 265A and 265B (collectively "electrode extensions 265"). As illustrated in FIG. 2I, electrode extension 265A includes a paddle 268 such that one or more electrodes 267 are distributed on paddle 268. Electrode extension 265B includes one or more ring electrodes 269. In some examples, electrode extensions 265 may be connected to a housing 256 of sensor device 250 via header pins. In some examples, electrode extensions 265 may be permanently attached to housing 256 of sensor device 250. The number and types of electrode extensions 265, electrodes on such extensions, and electrodes on housing 251 may differ from that illustrated by FIG. 2I in some examples. For example, there may be two or more electrodes on electrode extension 265A and/or 265B.

In some examples, electrode extensions 265 can have a length L1 of from about 15 to about 50 mm, from about 20 to about 30 mm, or about 25 mm. One or more electrode extensions 265 may provide sensor device 250 larger sensing vectors for sensing signals via electrodes. The larger (longer) sensing vectors that include one or more electrodes on one or more extensions may facilitate improved signal quality relative to smaller (shorter) sensing vectors. The location for sensing each desired signal may vary from patient to patient, so using electrode extensions 265 can improve the detection of signals such as EEG signals. Electrodes 263, 267, and 269 may create a matrix of electrodes on the head of the patient.

Electrode extensions 265 are inherently flexible, allowing conformance to neck and/or cranial anatomy. Additionally, the length and flexibility of one or more electrode extensions 265 may allow electrodes on the extension to advantageously be positioned proximate to certain brain structures or locations, vascular structures, or other anatomical structures or locations, which may also facilitate improved signal quality, e.g., when the signal originates from or is affected by the structure. Electrode extensions 265A and 265B can extend superiorly from sensor device 250 for enhanced brain signal sensing and detection. Improved signal quality may result in improved performance of algorithms for predicting or detecting patient conditions using such signals. In examples in which one or more electrode extensions 265 are implanted, the extension may be tunneled under the scalp to a position one or more electrodes on the extension at a desired location of the cranium.

FIGS. 2J-2N and 2P depict example sensor devices 270J-270N and 270P that includes electrode extensions 272J-272N and 272P, 276K, 276N, 284M-284N and 284P, 285M-285N and 285P, 286M-286N and 286P, in accordance with examples of the present disclosure. Sensor devices 270J-270N and 270P may be similar in other aspects to the sensor devices illustrated and described with respect to FIGS. 1A-2I, e.g., may include electronics within a housing, and electrodes on the housing. The electrode extensions shown in FIGS. 2J-2N and 2P may also be referred to as leads. The electrodes on electrode extensions 272J-272N and 272P, 276K, 276N, 284M-284N and 284P, 285M-285N and 285P, 286M-286N and 286P may be ring electrodes or paddle electrodes, as examples.

Figure 2J:
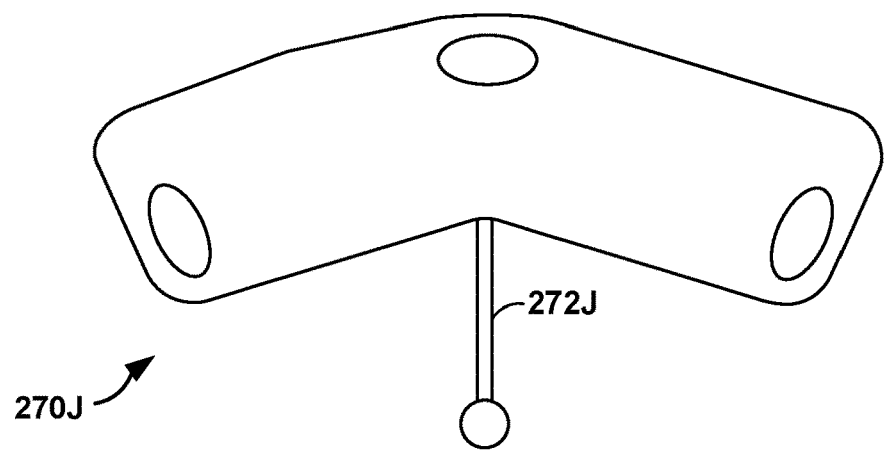
FIGS. 2J-2N and 2P depict example sensor devices that includes electrode extensions, in accordance with examples of the present disclosure.
Figure 2K:
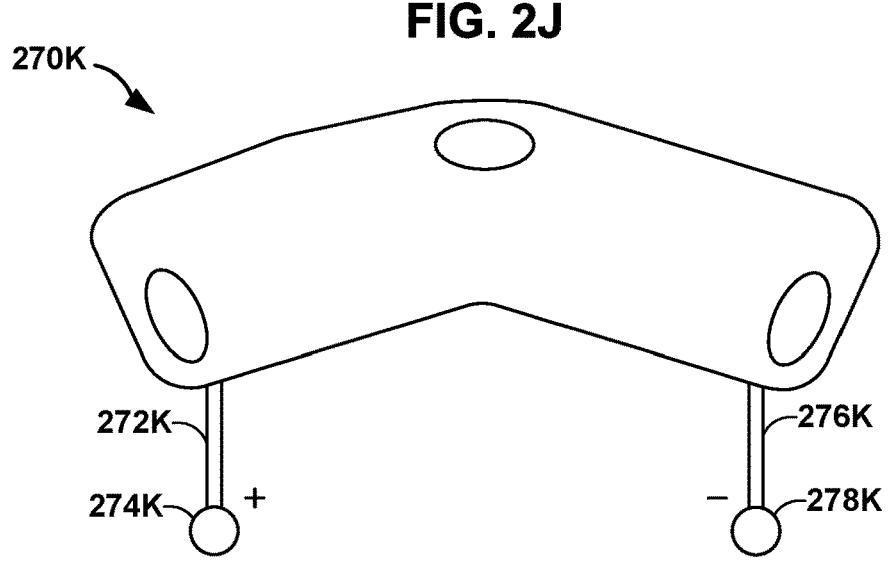
Figure 2L:
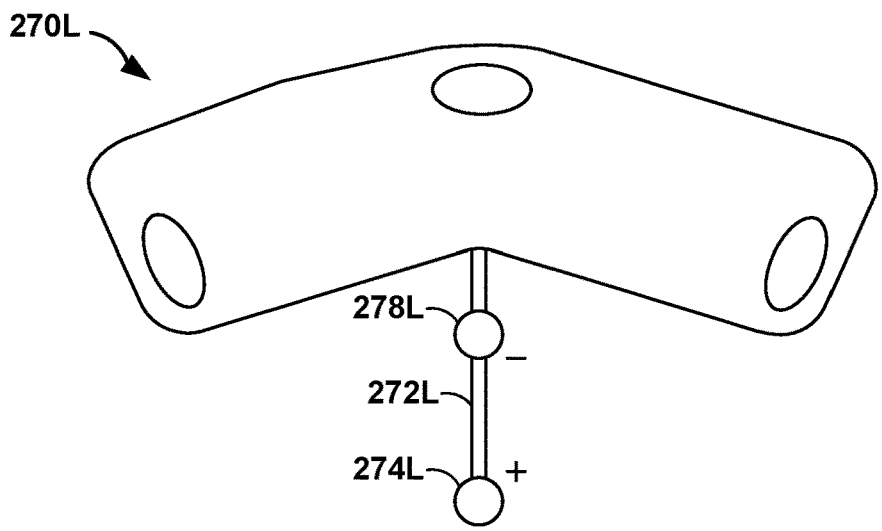
Figure 2M:
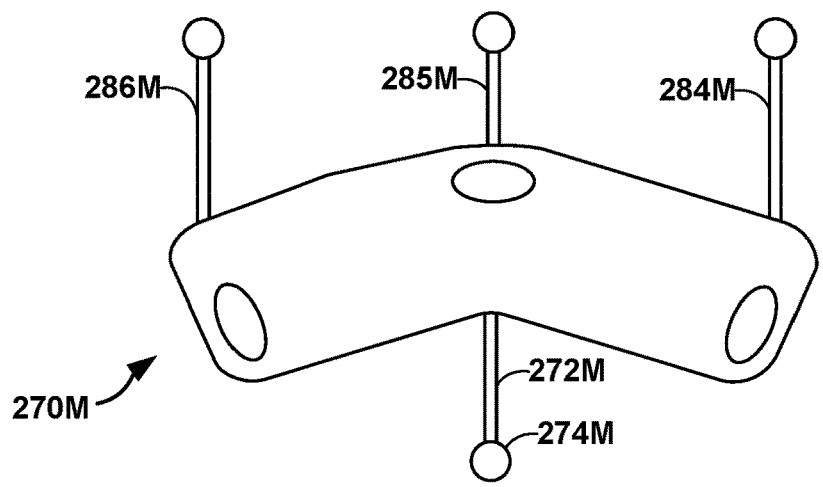
Figure 2N:
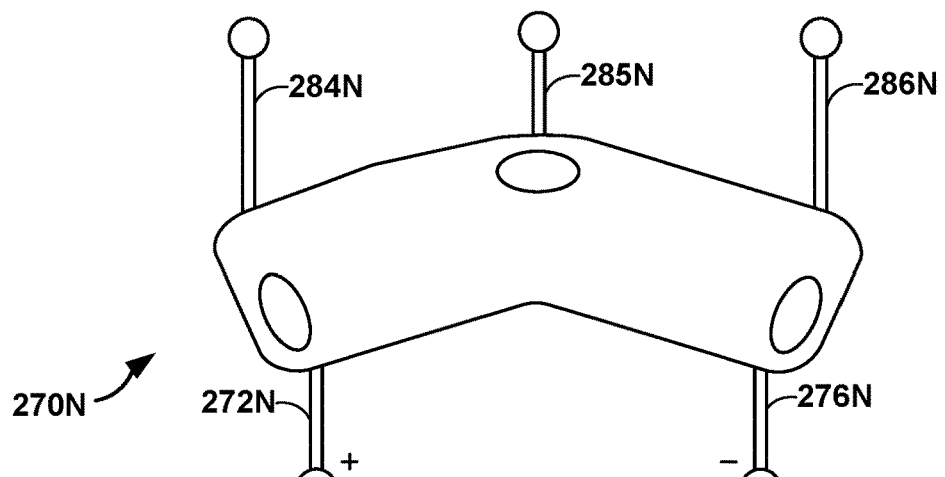
Figure 2P:
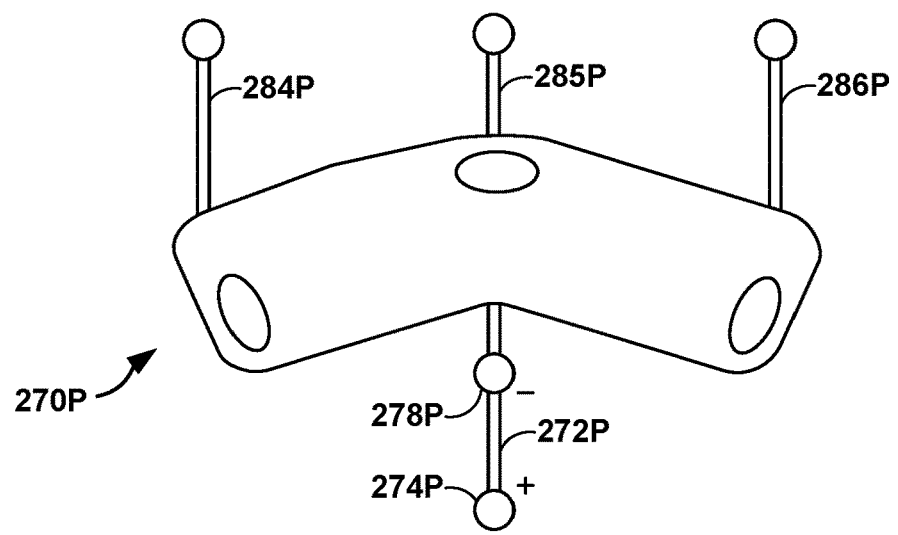

FIGS. 2J-2L show examples of electrode extensions 272J-272L and 276K that can be positioned to extend from sensor devices 270J-270L in a first direction, and FIGS. 2M, 2N, and 2P show examples of electrode extensions 272M-272P and 276N that can be positioned to extend from sensor devices 270M-270P in the first direction and electrode extensions 284M-284P, 285M-285P, and 286M-286P that can be positioned to extend from sensor devices 270M-270P in a second direction that is opposite from the first direction. In some examples, the first direction may be an inferior direction, e.g., towards the neck and shoulders of the patient, and the second direction may be a superior direction, e.g., towards the upper cranium and scalp of the patient. For example, a first electrode extension may be positioned to extend towards a first temporal region, and a second electrode extension may be positioned to extend towards a second temporal region. Electrode extensions 272J-272P and 276K shown in FIGS. 2J-2N and 2P can extend towards the neck and shoulders for enhanced cardiac signal sensing and detection. Electrode extensions 284M-284P, 285M-285P, and 286M-286P shown in FIGS. 2M, 2N, and 2P can be positioned to extend superiorly toward the upper cranium and scalp for enhanced brain signal sensing.

FIG. 2J shows an example of single electrode extension 272J that extends from the center of sensor device 270J. FIG. 2K shows an example of two electrode extensions 272K and 276K that extend from opposing ends of sensor device 270K. Electrode 274K on electrode extension 272K may have a positive polarity, and electrode 278K on electrode extension 276K may have a negative polarity, or the polarities of the electrodes may be reversed, such that the electrodes have opposite polarities. FIG. 2L shows an example of single electrode extension 272L that extends from the center of sensor device 270L. There are two electrodes 274L and 278L with opposing polarities on single electrode extension 272L. Thus, sensor devices 270K and 270L shown in FIGS. 2K and 2L may be configured to receive a differential signal via electrodes 274K, 278K, 274L, and 278L on one or more electrode extensions 272K, 276K, and 272L. In the example of FIG. 2J, a generally vertical or non-horizontal sensing vector may be formed between the electrode on extension 272J and an electrode on a housing of sensor device 270 J, and in the example of FIG. 2L, a generally vertical sensing vector may be formed between electrodes 274L and 278L on extension 272L. In the example of FIG. 2K, a generally horizontal sensing vector may be formed between electrode 274K on extension 272K and electrode 278K on extension 276K.

Each of sensor devices 270M-270P shown in FIGS. 2M-2P includes one or more electrode extensions 272M-272P and 276N that extend in a first direction and three electrode extensions 284M-284P, 285M-285P, and 286M-286P that extend in a second direction that is opposite from the first direction. FIG. 2M shows single electrode extension 272M that extends in the first direction from the center of sensor device 270M, where single electrode extension 272M includes electrode 274M. FIG. 2N shows two electrode extensions 272N and 276N that extend in the first direction from opposing ends of sensor device 270N. FIG. 2P shows single electrode extension 272P that extends from the center of sensor device 270P, where single electrode extension 272P includes two electrodes 274P and 278P of opposing polarities.

Figure 2Q:
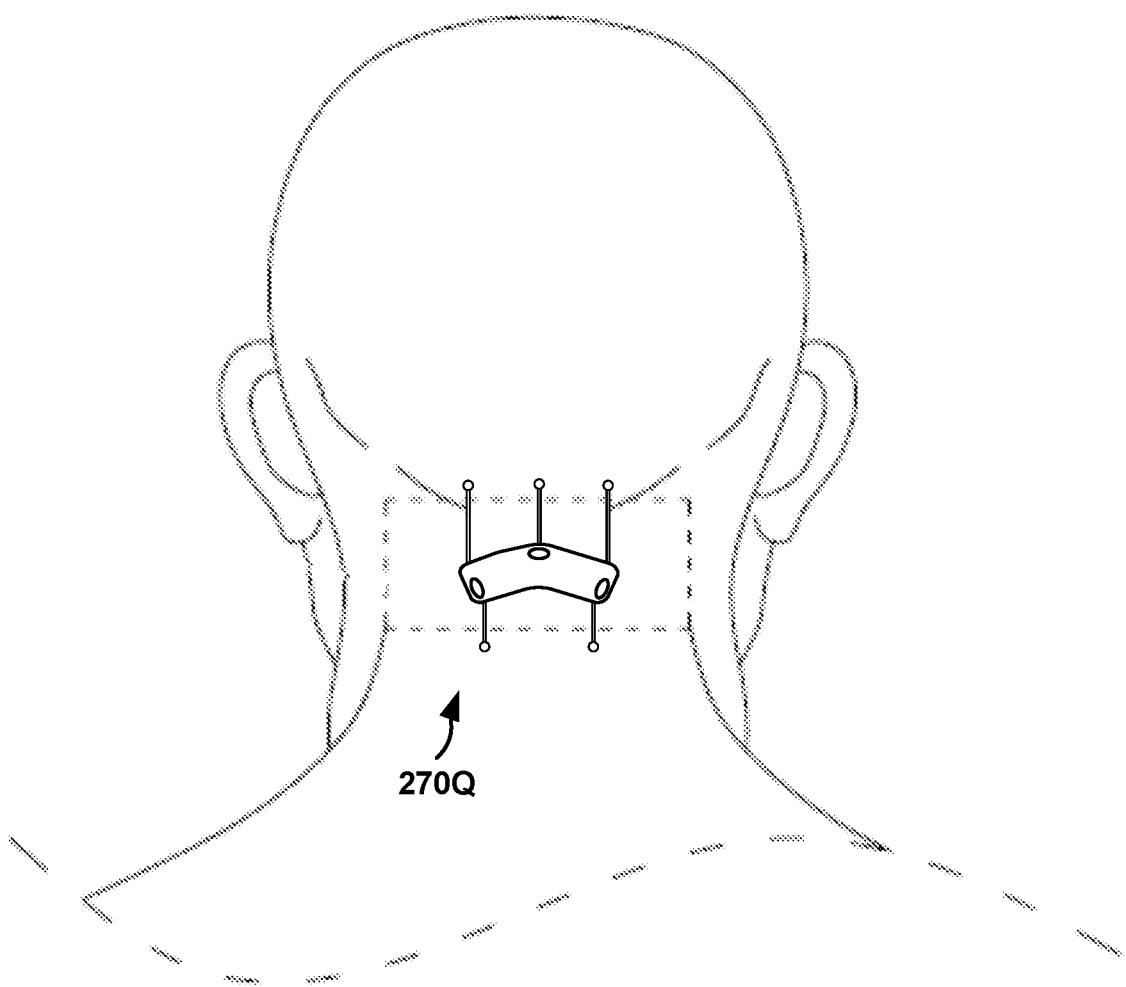
FIG. 2Q depicts an example sensor device that includes electrode extensions, in accordance with examples of the present disclosure.

FIG. 2Q shows sensor device 270Q on the back of a patient's neck. In the illustrated example, sensor device 270Q is configured similarly to sensor device 270N of FIG. 2N. However, any of the sensor devices including extensions described with respect to FIGS. I-P may be positioned in the manner illustrated by sensor device 270Q in FIG. 2Q. Additionally, any of the sensor devices including extensions described with respect to FIGS. 2I-2N, and 2P may be positioned at other locations described herein, such as temporally as illustrated with respect to FIG. 1B.

Such sensor devices may include one or more extensions extending in a first, inferior direction, toward the neck or shoulders of the patient. Extensions extending in this first direction may position electrodes to facilitate cardiac signal, e.g., ECG, sensing. Such sensor devices may include one or more extensions extending in a second, superior direction, opposite the first direction, toward the upper cranium and scalp of the patient. Extensions extending in this second direction may facilitate brain signal, e.g., EEG, sensing. Each extension may include one or more electrodes to provide one or more sensing vectors of one or more orientations with another electrode on the same extension, a different extension, or a housing of the sensor device.

Figure 3A:
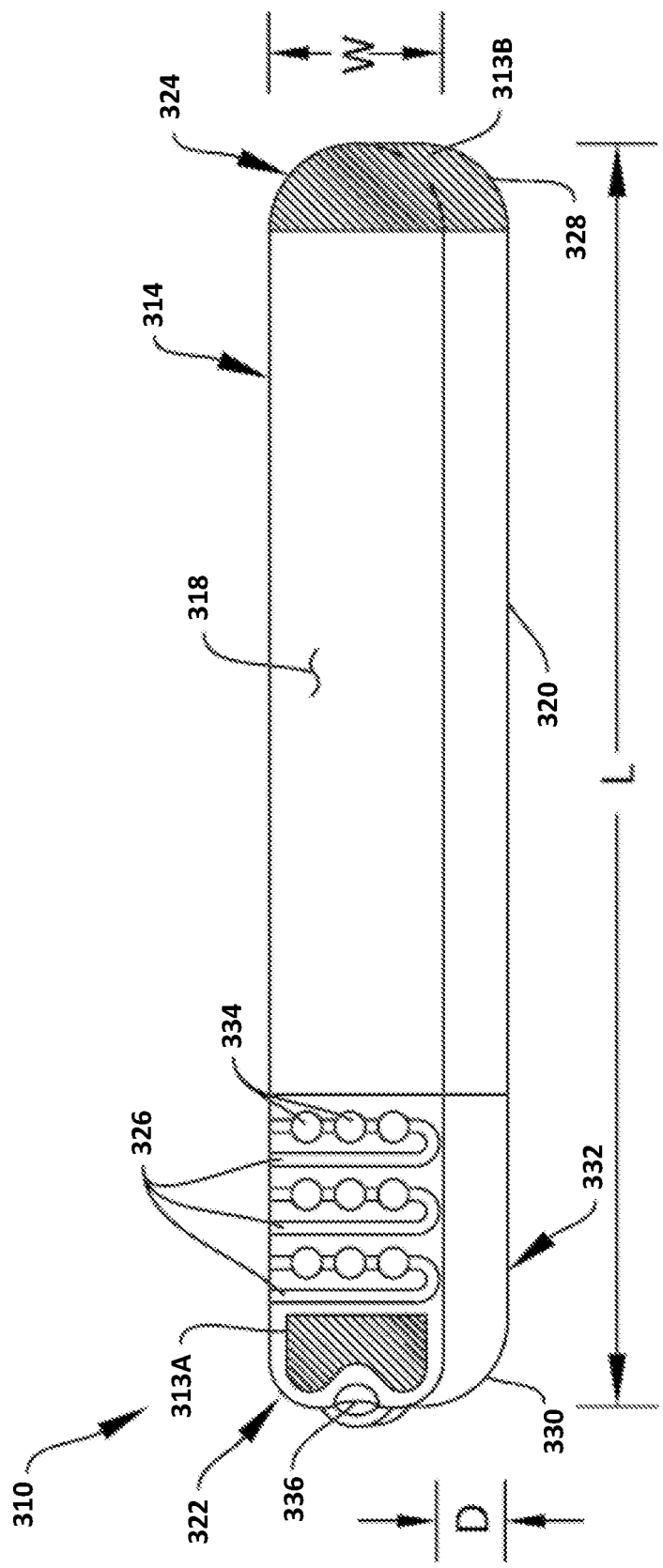
Figure 3B:
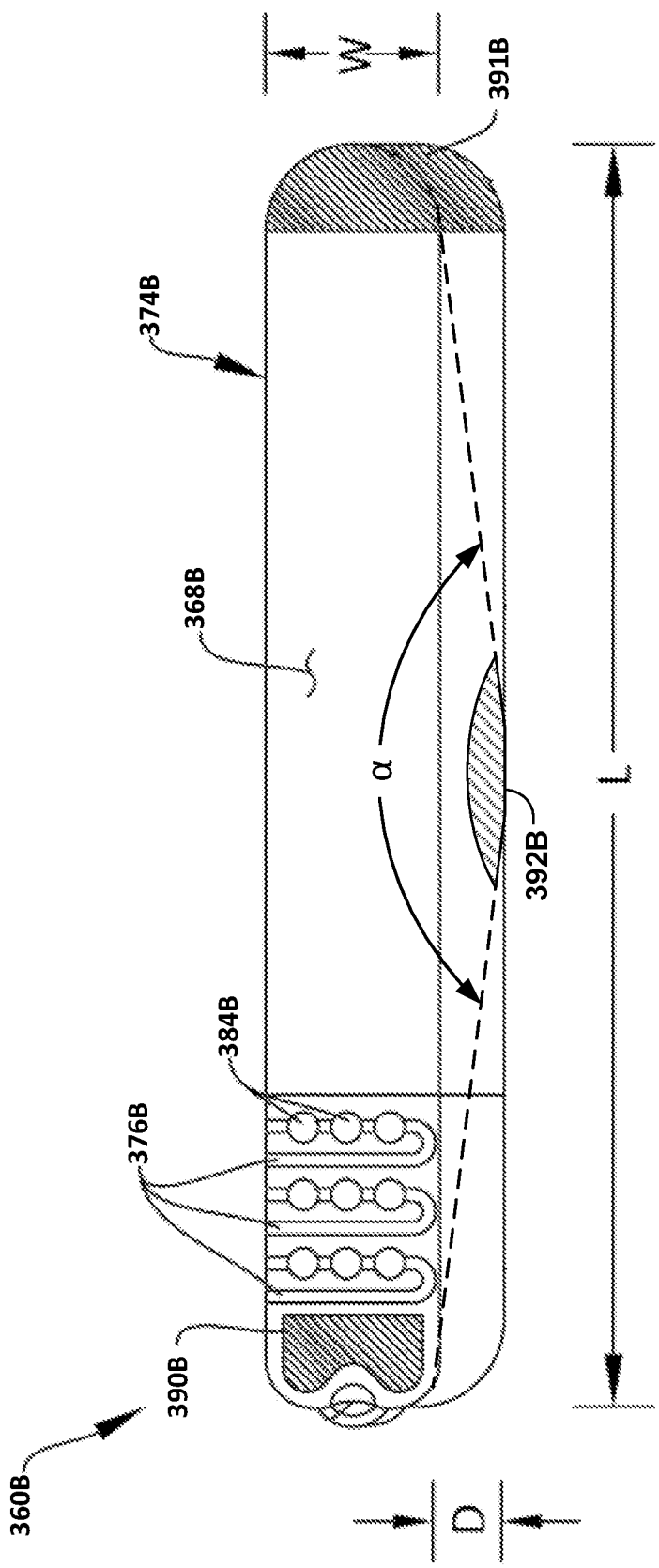

FIGS. 3A-3C depict other example sensor devices 310, 360B, and 360C in accordance with embodiments of the present technology. In some examples, sensor device 310 can include some or all of the features of sensor devices 106, 210, 220, 230, and 400, described herein in accordance with embodiments of the present technology, and can include additional features as described in connection with FIG. 3A. In the example shown in FIG. 3A, sensor device 310 may be embodied as a monitoring device having housing 314, proximal electrode 313A and distal electrode 313B (individually or collectively "electrode 313" or "electrodes 313"). Housing 314 may further comprise first major surface 318, second major surface 320, proximal end 322, and distal end 324. Housing 314 encloses electronic circuitry located inside sensor device 310 and protects the circuitry contained therein from body fluids. Electrical feedthroughs provide electrical connection of electrodes 313. In an example, sensor device 310 may be embodied as an external monitor, such as patch that may be positioned on an external surface of the patient, or another type of medical device (e.g., instead of as an ICM), such as described further herein.

In the example shown in FIG. 3A, sensor device 310 is defined by a length "L," a width "W," and thickness or depth "D." sensor device 310 may be in the form of an elongated rectangular prism wherein the length L is significantly larger than the width W, which in turn is larger than the depth D. In one example, the geometry of sensor device 310—in particular, a width W being greater than the depth D—is selected to allow sensor device 310 to be inserted under the skin of the patient using a minimally invasive procedure and to remain in the desired orientation during insertion. For example, the device shown in FIG. 3A includes radial asymmetries (notably, the rectangular shape) along the longitudinal axis that maintains the device in the proper orientation following insertion. For example, in one example the spacing between proximal electrode 313a and distal electrode 313B may range from 30 millimeters (mm) to 55 mm, 35 mm to 55 mm, and from 40 mm to 55 mm and may be any range or individual spacing from 25 mm to 60 mm. In-some examples, the length L may be from 30 mm to about 70 mm. In other examples, the length L may range from 40 mm to 60 mm, 45 mm to 60 mm and may be any length or range of lengths between about 30 mm and about 70 mm. In addition, the width W of first major surface 18 may range from 3 mm to 10 mm and may be any single or range of widths between 3 mm and 10 mm. The thickness of depth D of sensor device 310 may range from 2 mm to 9 mm. In other examples, the depth D of sensor device 310 may range from 2 mm to 5 mm and may be any single or range of depths from 2 mm to 9 mm. In addition, sensor device 310 according to an example of the present disclosure is has a geometry and size designed for ease of implant and patient comfort. Examples of sensor device 310 described in this disclosure may have a volume of 3 cc or less, 2 cc or less, 1 cc or less, 0.9 cc or less, 0.8 cc or less, 0.7 cc or less, 0.6 cc or less, 0.5 cc or less, 0.4 cc or less, any volume between 3 and 0.4 cc, or any volume that is less than 3 cc and greater than zero. In addition, in the example shown in FIG. 3A, proximal end 322 and distal end 324 are rounded to reduce discomfort and irritation to surrounding tissue once inserted under the skin of the patient.

In the example shown in FIG. 3A, once inserted within the patient, the first major surface 318 faces outward, toward the skin of the patient while the second major surface 320 is located opposite the first major surface 318. Consequently, the first and second major surfaces may face in directions along a sagittal axis of patient, and this orientation may be consistently achieved upon implantation due to the dimensions of sensor device 310. Additionally, an accelerometer, or axis of an accelerometer, may be oriented along the sagittal axis.

Proximal electrode 313A and distal electrode 313B are used to sense signals (e.g., EEG signals, ECG signals, other brain and/or cardiac signals, or impedance) which may be submuscular or subcutaneous. Signals may be stored in a memory of sensor device 310, and signal data may be transmitted via integrated antenna 326 to another medical device, which may be another implantable device or an external device, such as external device 108 (FIG. 1A). In some examples, electrodes 313A and 313B may additionally or alternatively be used for sensing any bio-potential signal of interest, such as an EMG or a nerve signal, from any implanted location.

In the example shown in FIG. 3A, proximal electrode 313A is in close proximity to the proximal end 322, and distal electrode 313B is in close proximity to distal end 324. In this example, distal electrode 313B is not limited to a flattened, outward facing surface, but may extend from first major surface 318 around rounded edges 328 or end surface 330 and onto the second major surface 320 so that the electrode 313B has a three-dimensional curved configuration. In the example shown in FIG. 3A, proximal electrode 313A is located on first major surface 318 and is substantially flat, outward facing. However, in other examples proximal electrode 313A may utilize the three-dimensional curved configuration of distal electrode 313B, providing a three-dimensional proximal electrode (not shown in this example). Similarly, in other examples distal electrode 313B may utilize a substantially flat, outward facing electrode located on first major surface 318 similar to that shown with respect to proximal electrode 313A. The various electrode configurations allow for configurations in which proximal electrode 313A and distal electrode 313B are located on both first major surface 318 and second major surface 320. In other configurations, such as that shown in FIG. 3A, only one of proximal electrode 313A and distal electrode 313B is located on both major surfaces 318 and 320, and in still other configurations both proximal electrode 313A and distal electrode 313B are located on one of the first major surface 318 or the second major surface 320 (e.g., proximal electrode 313A located on first major surface 318 while distal electrode 313B is located on second major surface 320). In another example, sensor device 310 may include electrodes 313 on both first major surface 318 and second major surface 320 at or near the proximal and distal ends of the device, such that a total of four electrodes 313 are included on sensor device 310. Electrodes 313 may be formed of a plurality of different types of biocompatible conductive material (e.g., stainless steel, titanium, platinum iridium, or alloys thereof), and may utilize one or more coatings such as titanium nitride or fractal titanium nitride. Although the example shown in FIG. 3A includes two electrodes 313, in some embodiments sensor device 310 can include 3, 4, 5, or more electrodes carried by the housing 314.

In the example shown in FIG. 3A, proximal end 322 includes a header assembly 332 that includes one or more of proximal electrode 313A, integrated antenna 326, anti-migration projections 334, or suture hole 336. Integrated antenna 326 is located on the same major surface (i.e., first major surface 318) as proximal electrode 313a and is also included as part of header assembly 332. Integrated antenna 326 allows sensor device 310 to transmit or receive data. In other examples, integrated antenna 326 may be formed on the opposite major surface as proximal electrode 313A, or may be incorporated within the housing 314 of sensor device 310. In the example shown in FIG. 3A, anti-migration projections 334 are located adjacent to integrated antenna 326 and protrude away from first major surface 318 to prevent longitudinal movement of the device. In the example shown in FIG. 3A anti-migration projections 334 includes a plurality (e.g., six or nine) small bumps or protrusions extending away from first major surface 318. As discussed above, in other examples anti-migration projections 334 may be located on the opposite major surface as proximal electrode 313A or integrated antenna 326. In addition, in the example shown in FIG. 3A header assembly 332 includes suture hole 336, which provides another means of securing sensor device 310 to the patient to prevent movement following insert. In the example shown, suture hole 336 is located adjacent to proximal electrode 313A. In one example, header assembly 332 is a molded header assembly made from a polymeric or plastic material, which may be integrated or separable from the main portion of sensor device 310.

FIG. 3B shows a third electrode 392B at a midpoint between electrodes 390B and 391B. The dimension D of housing 374B of sensor device 360B can be increased to adjust the angle α to obtain a more orthogonal orientation for the triangular configuration of electrodes 390B-392B. In some examples, sensor device 360B may have the same shape and dimensions as sensor device 310, except that electrode 392B is added to the side surface or back surface of housing 374B to create a triangle-shaped electrode configuration. In some examples, sensor device 360B may have a first major surface 368B, integrated antenna 376B, and anti-migration projections 384B. In addition, FIG. 3C shows sensor device 360C with an extended third dimension D. In some examples, sensor device 360C may have a first major surface 368C, integrated antenna 376C, and anti-migration projections 384C. Third electrode 392C is positioned at a corner to create a triangular-shaped electrode configuration with electrodes 390C and 391C. Dimension D can be designed to achieve specific angles for the triangular configuration of electrodes 390C-392C.

In addition to the electrodes shown in FIGS. 2A-2H and 3A-3C, a sensor device may include supplementary electrodes configured to record noise, such as environmental noise and/or EMG signals from the skeletal muscles. The recorded noise could be subtracted from the signals sensed by a pair of primary electrodes to cancel or reduce the noise in the signals sensed by the pair of primary electrodes. The supplementary electrodes can be positioned on the backside of a housing or a can of the sensor device facing the skeletal muscle to sense the skeletal muscle noise for the purpose of canceling the noise. Additionally or alternatively, a separate device such as a wearable device or external patch may include electrodes for sensing noise. The separate device may be configured to communicate sensed signals to the sensor device shown in FIGS. 2A-2H and 3A-3C, where the sensor device may be configured to use the received signals for noise reduction and cancelation to improve the signal-to-noise ratio.

Figure 4:
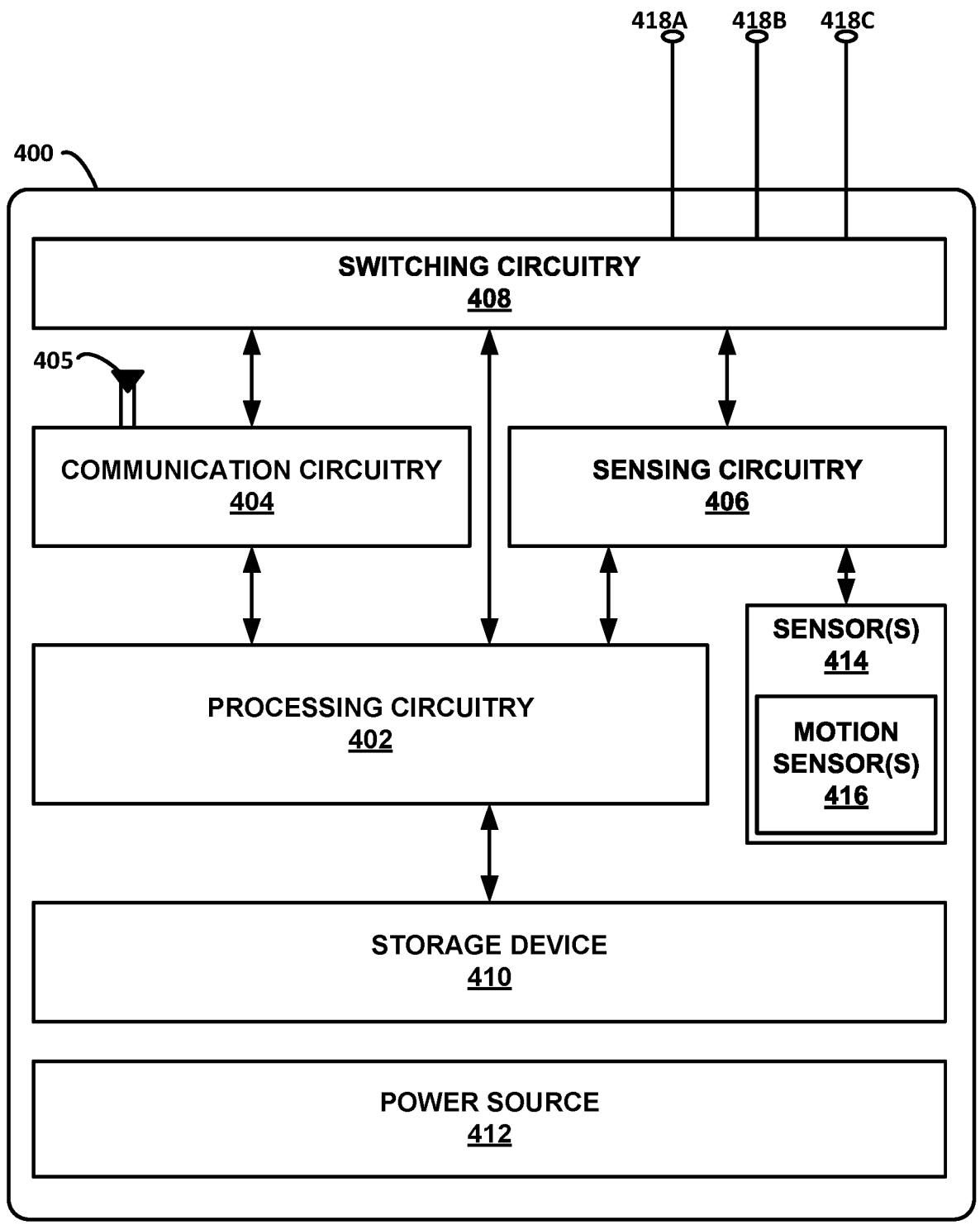
FIG. 4 is a block diagram of an example sensor device configured to detect stroke or seizure.

FIG. 4 is a block diagram of an example sensor device 400 configured to detect stroke or seizure. Sensor device 400 may be an example of any of sensor device 400 or sensor devices 106, 210, 220, 230, 240, 250, 270, 310, 360B, or 360C. In the illustrated example, sensor device 400 includes electrodes 418A-418C (collectively, "electrodes 418"), antenna 405, processing circuitry 402, sensing circuitry 406, communication circuitry 404, storage device 410, switching circuitry 408, sensors 414 including motion sensor(s) 416, and power source 412. Although not illustrated in FIGS. 3A-3C, sensors 414 may include one or more light detectors.

Processing circuitry 402 may include fixed function circuitry and/or programmable processing circuitry. Processing circuitry 402 may include any one or more of a microprocessor, a controller, a DSP, an ASIC, an FPGA, a tensor processing unit, a graphical processing unit, or equivalent discrete or analog logic circuitry. In some examples, processing circuitry 402 may include multiple components, such as any combination of one or more microprocessors, one or more controllers, one or more DSPs, one or more ASICs, or one or more FPGAs, as well as other discrete or integrated logic circuitry. The functions attributed to processing circuitry 402 herein may be embodied as software, firmware, hardware, or any combination thereof. Processing circuitry 402 may be an example of or component of processing circuitry 110 (FIGS. 1A and 1B), and may be processing circuitry of any of sensor devices 106, 210, 220, 230, 240, 250, 270, 310, 360A, and 360B.

Sensing circuitry 406 and communication circuitry 404 may be selectively coupled to electrodes 418 via switching circuitry 408, as controlled by processing circuitry 402. Sensing circuitry 406 may monitor signals from electrodes 418 in order to monitor electrical activity of the brain (e.g., to produce an EEG, and ECG or other cardiac signal) from which processing circuitry 402 may generate stroke metrics and seizure metrics. Sensing circuitry 406 may also sense physiological characteristics such as subcutaneous tissue impedance, the impedance being indicative of at least some aspects of patient 102's respiratory patterns and the EMG or ECG being indicative of at least some aspects of patient 102's cardiac patterns. Sensing circuitry 406 also may monitor signals from sensors 414, which may include motion sensor(s) 416, and any additional sensors, such as light detectors, pressure sensors, or acoustic sensors, that may be positioned on or in sensor device 400.

In some examples, a subcutaneous impedance signal collected by sensor device 400 may indicate a respiratory rate and/or a respiratory intensity of patient 102, or tissue perfusion of the patient, and an EMG collected by sensor device 400 may indicate a heart rate of patient 102 and an atrial fibrillation (AF) burden of patient 102 or other arrhythmia. In some examples, a respiration component may additionally (using a blended sensor technique) or alternatively be sensed in other signals, such as a motion sensor signal, optical signal, or as a component (e.g., baseline shift) of the cardiac signal sensed via electrodes 418. In some examples, sensing circuitry 406 may include one or more filters and amplifiers for filtering and amplifying signals received from one or more of electrodes 418 and/or motion sensor(s) 42. In some examples, sensing circuitry 406 may include separate hardware (e.g., separate circuits) configured to condition and process sensed signals from which seizure metrics and stroke metrics are generated. In this manner each separate circuit may perform one or more filters and amplifiers configured to extract relevant features or signal components from the sensed signals. Moreover, processing circuitry 402 may selective control each separate circuit depending on whether a seizure or stroke metric should be generated.

Communication circuitry 404 may include any suitable hardware, firmware, software, or any combination thereof for communicating with another device, such as external device 108 or another sensor device or sensor, such as a pressure sensing device. Under the control of processing circuitry 402, communication circuitry 404 may receive downlink telemetry from, as well as send uplink telemetry to, external device 108 or another device with the aid of an internal or external antenna, e.g., antenna 405. In some examples, communication circuitry 404 may receive downlink telemetry from, as well as send uplink telemetry to, external device 108 or another device via tissue conductance communication (TCC) using two or more of electrodes 418, e.g., as selected by processing circuitry 402 via switching circuitry 408. In addition, processing circuitry 402 may communicate with a networked computing device via an external device (e.g., external device 108) and a computer network, such as the Medtronic CareLink® Network developed by Medtronic, plc, of Dublin, Ireland. Additionally or alternatively, communication circuitry 404 may be configured to communicate with external or implanted devices using tissue conductance communication (TCC).

A clinician or other user may retrieve data from sensor device 400 using external device 108, or by using another local or networked computing device configured to communicate with processing circuitry 402 via communication circuitry 404. The clinician may also program parameters of sensor device 400 using external device 108 or another local or networked computing device.

In some examples, storage device 410 may be referred to as a memory and include computer-readable instructions that, when executed by processing circuitry 402, cause sensor device 400 and processing circuitry 402 to perform various functions attributed to sensor device 400 and processing circuitry 402 herein. Storage device 410 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Storage device 410 may also store data generated by sensing circuitry 406, such as physiological information, or data generated by processing circuitry 402, such as stroke metrics and seizure metrics.

Power source 412 is configured to deliver operating power to the components of sensor device 400. Power source 412 may include a battery and a power generation circuit to produce the operating power. In some examples, the battery is rechargeable to allow extended operation. In some examples, recharging is accomplished through proximal inductive interaction between an external charger and an inductive charging coil within external device 108. Power source 412 may include any one or more of a plurality of different battery types, such as nickel cadmium batteries and lithium ion batteries. A non-rechargeable battery may be selected to last for several years, while a rechargeable battery may be inductively charged from an external device, e.g., on a daily or weekly basis.

As described herein, sensor device 400 may be configured to sense signals and generate stroke metrics indicative of whether or not patient 102 has experienced or has a threshold risk of experiencing a stroke and/or metrics for other patient conditions. In some examples, the processing circuitry 402 is configured to analyze data from one or more electrode combinations using electrodes 418 to extract and separate brain activity data and heart activity data, and to discard or reduce any contribution from muscle activity. In some examples, the electrodes 418 are configured to be disposed over the patient's skin. In such embodiments, the electrodes 418 can include protrusions (e.g., microneedles or other suitable structures) configured to at least partially penetrate the patient's skin so as to improve detection of subcutaneous electrical activity.

In some examples, sensing circuitry 406 senses a brain signal via electrodes 418. The brain signal may represent the electrical activity of the brain, and may be an EEG. As described herein, processing circuitry 402 may determine parameter values from the brain signal, such values determined based on magnitudes of the signal in one or more frequency bands. Sensing circuitry 406 may include filters and other circuitry to isolate the brain signal of interest.

In some examples, sensing circuitry 406 senses a cardiac signal, and processing circuitry 402 may determine parameter values from the cardiac signal. Example parameter values as described herein, such as heart rate or heart rate variability, may be determined based on detection of occurrence of cardiac beats in the cardiac signal. Sensing circuitry 406 may be configured to sense a variety of different signals within which cardiac beats may be identified and values of cardiac parameters may be determined.

For example, sensing circuitry 406 may be configured to sense a cardiac signal representing the electrical activity (e.g., depolarizations and repolarizations) of the heart, such as a subcutaneous ECG signal, via electrodes 418. As another example, sensing circuitry 406 may be configured to sense a cardiac signal representing mechanical activity of the heart via electrodes 418. A component of a signal sensed via electrodes 418, e.g., on or under the scalp of the patient, may vary based on vibration, blood flow, or impedance changes associated with cardiac contractions. Filtering to isolate this component may include 0.5 to 3 Hz bandpass filtering, although other filtering ranges and cutoffs are possible. In some examples, sensing circuitry 406 may be configured to sense a cardiac signal representing mechanical activity of the heart via other sensors 414, such as optical sensors, pressure sensors, or motion sensors 416.

One or more electrodes 418 may be positioned, e.g., during implantation of sensor device 400, to facilitate sensing of a cardiac signal via the electrodes. In some examples, sensor device 400 may include one or more electrode extensions 265, 272, 276, and 284-286 to facilitate positioning of one or more electrodes 418, e.g., via tunneling under the scalp, at desired locations for sensing the brain and/or cardiac signals. Desired locations for sensing brain and cardiac signals using electrodes 418 may be determined prior to implantation of sensor device 406 for a particular patient using external sensing equipment, such as standard multi-electrode ECG and EEG equipment, either on the particular patient, or experimentally on a number of subjects. In some examples, the one or more housing-based electrodes 418 of sensor device 400 are positioned at a desired location for sensing a brain signal and the one or more extension-based electrodes 418 are positioned at a desired location for sensing a cardiac signal, or vis-a-versa. With reference to FIG. 1C, example locations for positioning an electrode for sensing cardiac signals include P3, PQ3, PQ7, F3, F2, AF3, or C2.

In some examples, processing circuitry 402 may utilize both electrical, e.g., ECG, and pulsatile cardiac signals in an integrated fashion for the detection, prediction, and/or classification of conditions. In some examples, such integration may result in an "enhanced" ECG signal. For example, processing circuitry 402 may identify features within an ECG signal based on the timing of pulses in a pulsatile signal. In some examples, processing circuitry 402 may account for a delay in pulsatile timing relative to the ECG in such integration.

Processing circuitry 402 may be configured to calculate physiological characteristics relating to one or more signals received from the electrodes 418, such as stroke metrics. For example, processing circuitry 402 may be configured to algorithmically determine the presence or absence of a stroke and/or risk thereof (via generation of a stroke metric) or other neurological and/or cardiac condition from the signal. In certain examples, processing circuitry 402 may make a determination for each electrode 418 (e.g., channel) or may make a determination using signals acquired from two or more selected electrodes 418. In some examples, to determine physiological characteristics, circuitry 402, 404, 406, and/or 408 may be configured to generate composite ECG and EEG signals based on signals received at electrodes 418.

Sensor device 400 may also be configured to sense signals and generate seizure metrics indicative of whether or not patient 102 has experienced a seizure. For example, processing circuitry 402 may be configured to analyze physiological information received from sensing circuitry 406 (e.g., EEG information). Processing circuitry 402 may search for one or more features in the physiological information that are indicative of one or more types of seizures. For example, processing circuitry 402 may identify frequency bands that include oscillations or amplitudes that exceed respective thresholds. In other examples, processing circuitry 402 may apply one or more machine-learning algorithms or other algorithms to the physiological information to identify when the patient's physiological information is indicative of a seizure.

In some examples, processing circuitry 402 may employ patient movement information as a part of seizure detection and stroke detection. For example, motion sensor 416 may include one or more accelerometers configured to detect patient movement. Processing circuitry 402 or sensing circuitry 406 may determine whether or not a patient has fallen based on the patient movement data collected via the accelerometer. Fall detection can be particularly valuable when assessing potential stroke patients, as a large percentage of patients admitted for ischemic or hemorrhagic stroke have been found to have had a significant fall within 15 days of the stroke event. Accordingly, in some embodiments, the processing circuitry 402 can be configured to initiate monitoring of brain activity via the electrodes 418 upon fall detection using the accelerometer. In some examples, the sensing performed via the electrodes 418 can be modified in response to a fall determination, for example with an increased sampling rate or other modification. In addition to fall detection, the accelerometer 115 (or similar sensor) can be used to determine potential body trauma due to sudden acceleration and/or deceleration (e.g., a vehicular accident, sports collision, concussion, etc.). These events could be thrombolytic, a precursor to stroke. Similar to stroke determination, these fall determinations or other movements can be employed by processing circuitry 402 when determining the seizure metric or otherwise determining whether or not the patient is experiencing, or has experienced, a seizure. For example, sensors 414 may detect head movement frequency indicative of a seizure and initiate or increase the sensing frequency of signal sensing and seizure metric generation.

Figure 5:
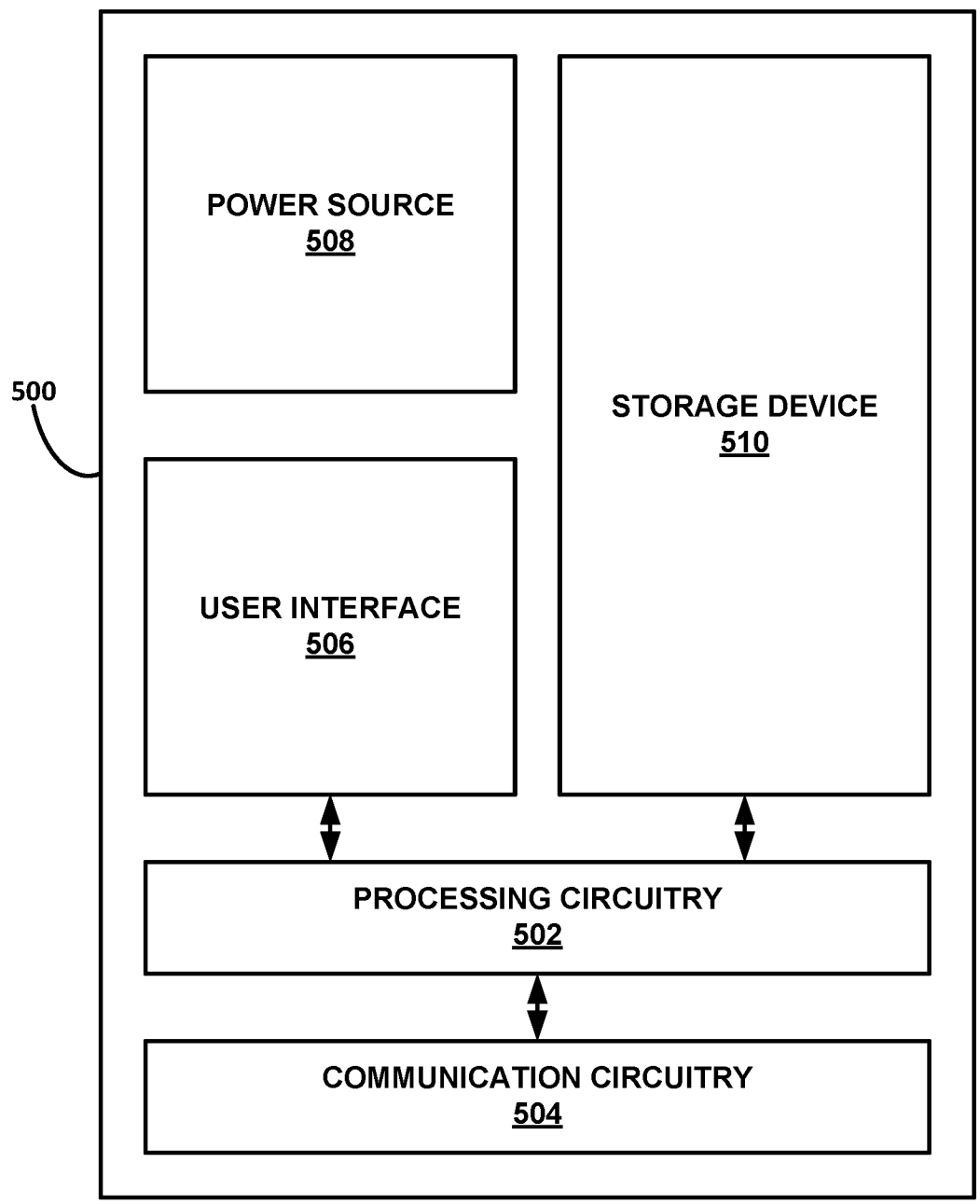
FIG. 5 is a block diagram of an example external device configured to communicate with the sensor device of FIG. 4.

FIG. 5 is a block diagram of an example external device 500 configured to communicate with any sensor device (e.g., sensor device 106 or sensor device 400) or sensor device described herein. External device 500 is an example of external device 108 of FIG. 1A. In the example of FIG. 5, external device 500 includes processing circuitry 502, communication circuitry 504, storage device 510, user interface 506, and power source 508.

Processing circuitry 502, in one example, may include one or more processors that are configured to implement functionality and/or process instructions for execution within external device 500. For example, processing circuitry 502 may be capable of processing instructions stored in storage device 510. Processing circuitry 502 may include, for example, microprocessors, DSPs, ASICs, FPGAs, or equivalent discrete or integrated logic circuitry, or a combination of any of the foregoing devices or circuitry. Accordingly, processing circuitry 502 may include any suitable structure, whether in hardware, software, firmware, or any combination thereof, to perform the functions ascribed herein to processing circuitry 502. In some examples, processing circuitry 502 is configured to determine physiological characteristics by generating composite ECG and EEG signals based on signals by a sensor device.

Communication circuitry 504 may include any suitable hardware, firmware, software, or any combination thereof for communicating with another device, such as sensor device 400. Under the control of processing circuitry 502, communication circuitry 504 may receive downlink telemetry from, as well as send uplink telemetry to, sensor device 400, or another device. Additionally or alternatively, communication circuitry 404 may be configured to communicate with external or implanted devices using TCC. For example, sensor device 400 may be configured to send raw signals received at electrodes 418 to communication circuitry 504 for processing by external device 500. Processing circuitry 502 may be configured to generate composite ECG and EEG signals based on signals received from sensor device 400.

Storage device 510 may be configured to store information within external device 500 during operation. Storage device 510 may include a computer-readable storage medium or computer-readable storage device. In some examples, storage device 510 includes one or more of a short-term memory or a long-term memory. Storage device 510 may include, for example, RAM, dynamic random access memories (DRAM), static random access memories (SRAM), magnetic discs, optical discs, flash memories, or forms of electrically programmable memories (EPROM) or EEPROM. In some examples, storage device 510 is used to store data indicative of instructions for execution by processing circuitry 502. Storage device 510 may be used by software or applications running on external device 500 to temporarily store information during program execution.

Data exchanged between external device 500 and sensor device 400 may include operational parameters. External device 500 may transmit data including computer readable instructions which, when implemented by sensor device 400, may control sensor device 400 to change one or more operational parameters and/or export collected data. For example, processing circuitry 502 may transmit an instruction to sensor device 400 which requests sensor device 400 to export collected data (e.g., data corresponding to one or more of the physiological information, seizure metrics, stroke metrics, or accelerometer signal) to external device 500. In turn, external device 500 may receive the collected data from sensor device 400 and store the collected data in storage device 510. Additionally, or alternatively, processing circuitry 502 may export instructions to sensor device 400 requesting sensor device 400 to update electrode combinations for stimulation or sensing.

A user, such as a clinician or patient 102, may interact with external device 500 through user interface 506. User interface 506 includes a display (not shown), such as an LCD or LED display or other type of screen, with which processing circuitry 502 may present information related to sensor device 400 (e.g., stroke and/or seizure metrics). In addition, user interface 506 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 502 of external device 500 and provide input. In other examples, user interface 506 also includes audio circuitry for providing audible notifications, instructions, or other sounds to patient 102, receiving voice commands from patient 102, or both. Storage device 510 may include instructions for operating user interface 506 and for managing power source 508.

Power source 508 is configured to deliver operating power to the components of external device 500. Power source 508 may include a battery and a power generation circuit to produce the operating power. In some examples, the battery is rechargeable to allow extended operation. Recharging may be accomplished by electrically coupling power source 508 to a cradle or plug that is connected to an alternating current (AC) outlet. In addition, recharging may be accomplished through proximal inductive interaction between an external charger and an inductive charging coil within external device 500. In other examples, traditional batteries (e.g., nickel cadmium or lithium ion batteries) may be used. In addition, external device 500 may be directly coupled to an alternating current outlet to operate.

In some examples, external device 500 may provide an alert to the patient or another entity (e.g., a call center) based on a stroke or seizure indication provided by sensor device 400. The alert may be overridden by user input to provide a false alarm when no emergency has occurred. Additionally or alternatively, external device 500 may output user prompts which can be synchronized with data collection via sensor device 400. For example, external device 500 may instruct the user to lift an arm, make a facial expression, etc., and sensor device 400 may record physiological data while the user performs the requested actions. Moreover, external device 500 may itself analyze the patient (e.g., the patient's activity or condition in response to such prompts), for example using a camera to detect facial drooping, using a microphone to detect slurred speech, or to detect any other indicia of stroke. In some embodiments, such indicia can be compared against pre-stroke inputs (e.g., a stored baseline facial image or voice-print with baseline speech recording). Similarly, external device 500 may user one or more sensors to detect patient movement or facial activity to provide data indicative of a seizure or upcoming seizure.

Figure 6:
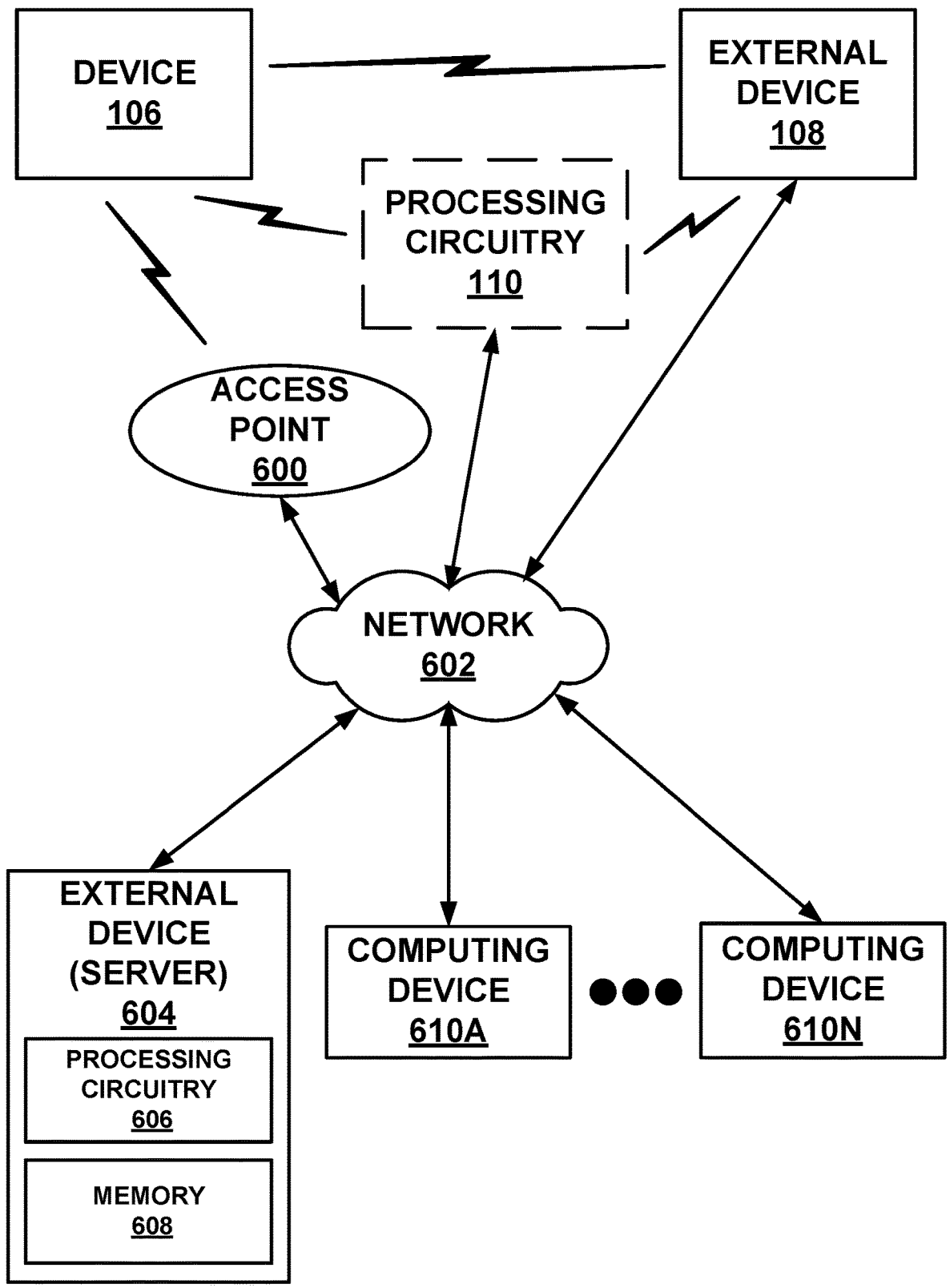
FIG. 6 is a block diagram illustrating an example system that includes an access point, a network, external computing devices, such as a server, and one or more other computing devices, which may be coupled to the IMD, the external device, and the processing circuitry of FIG. 1 via a network, in accordance with one or more techniques described herein.

FIG. 6 is a block diagram illustrating an example system that includes an access point 600, a network 602, external computing devices, such as a server 604, and one or more other computing devices 610A-610N, which may be coupled to sensor device 106, external device 108, and processing circuitry 110 via network 602, in accordance with one or more techniques described herein. In this example, sensor device 106 may use communication circuitry to communicate with external device 108 via a first wireless connection, and to communication with an access point 600 via a second wireless connection. In the example of FIG. 6, access point 600, external device 108, server 604, and computing devices 610A-610N are interconnected and may communicate with each other through network 602.

Access point 600 may include a device that connects to network 602 via any of a variety of connections, such as Wi-Fi, Bluetooth, ethernet, or cable modem connections. In other examples, access point 600 may be coupled to network 602 through different forms of connections, including wired or wireless connections. In some examples, access point 600 may be a user device, such as a tablet or smartphone, that may be co-located with the patient. As discussed above, sensor device 106 may be configured to transmit data, such as any one or combination of an EGM signal, an accelerometer signal, and a tissue impedance signal to external device 108. In addition, access point 600 may interrogate sensor device 106, such as periodically or in response to a command from the patient or network 602, in order to retrieve parameter values determined by processing circuitry of sensor device 106, or other operational or patient data from sensor device 106. Access point 600 may then communicate the retrieved data to server 604 via network 602.

In some cases, server 604 may be configured to provide a secure storage site for data that has been collected from sensor device 106, and/or external device 108. In some cases, server 604 may assemble data in web pages or other documents for viewing by trained professionals, such as clinicians, via computing devices 610A-610N. One or more aspects of the illustrated system of FIG. 6 may be implemented with general network technology and functionality, which may be similar to that provided by the Medtronic CareLink® Network developed by Medtronic plc, of Dublin, Ireland.

Server 604 may include processing circuitry 606. Processing circuitry 606 may include fixed function circuitry and/or programmable processing circuitry. Processing circuitry 606 may include any one or more of a microprocessor, a controller, a DSP, an ASIC, an FPGA, or equivalent discrete or analog logic circuitry. In some examples, processing circuitry 606 may include multiple components, such as any combination of one or more microprocessors, one or more controllers, one or more DSPs, one or more ASICs, or one or more FPGAs, as well as other discrete or integrated logic circuitry. The functions attributed to processing circuitry 606 herein may be embodied as software, firmware, hardware, or any combination thereof. In some examples, processing circuitry 606 may perform one or more techniques described herein based on an EGM signal, impedance signal, an accelerometer signal, or other sensor signals received from sensor device 106, or parameter values determined based on such signals by sensor device 106 and received from sensor device 106, as examples. For example, processing circuitry may perform one or more of the techniques described herein to identify significant changes in one or more physiological parameters resulting from an event, such changes resulting from a medical treatment.

Server 604 may include memory 608. Memory 608 includes computer-readable instructions that, when executed by processing circuitry 606, cause sensor device 106 and processing circuitry 606 to perform various functions attributed to sensor device 106 and processing circuitry 606 herein. Memory 608 may include any volatile, non-volatile, magnetic, optical, or electrical media, such as RAM, ROM, NVRAM, EEPROM, flash memory, or any other digital media.

In some examples, one or more of computing devices 610A-610N (e.g., device 610A) may be a tablet or other smart device located with a clinician, by which the clinician may program, receive alerts from, and/or interrogate sensor device 106. For example, the clinician may access data corresponding to any one or combination of sensed physiological signals, an accelerometer signal, seizure metrics, stroke metrics, and other types of signals collected by sensor device 106, or parameter values determined by sensor device 106 based on such signals, through device 610A, such as when patient 102 is in between clinician visits, to check on a status of a medical condition. In some examples, the clinician may enter instructions for a medical intervention for patient 102 into an app in device 610A, such as based on a status of a patient condition determined by sensor device 106, external device 108, processing circuitry 110, or any combination thereof, or based on other patient data known to the clinician. Device 610A then may transmit the instructions for medical intervention to another of computing devices 610A-610N (e.g., device 610B) located with patient 102 or a caregiver of patient 102. For example, such instructions for medical intervention may include an instruction to change a drug dosage, timing, or selection, to schedule a visit with the clinician, or to seek medical attention. In further examples, device 610B may generate an alert to patient 102 based on a status of a medical condition of patient 102 determined by sensor device 106, which may enable patient 102 proactively to seek medical attention prior to receiving instructions for a medical intervention. In this manner, patient 102 may be empowered to take action, as needed, to address his or her medical status, which may help improve clinical outcomes for patient 102.

Figure 7:
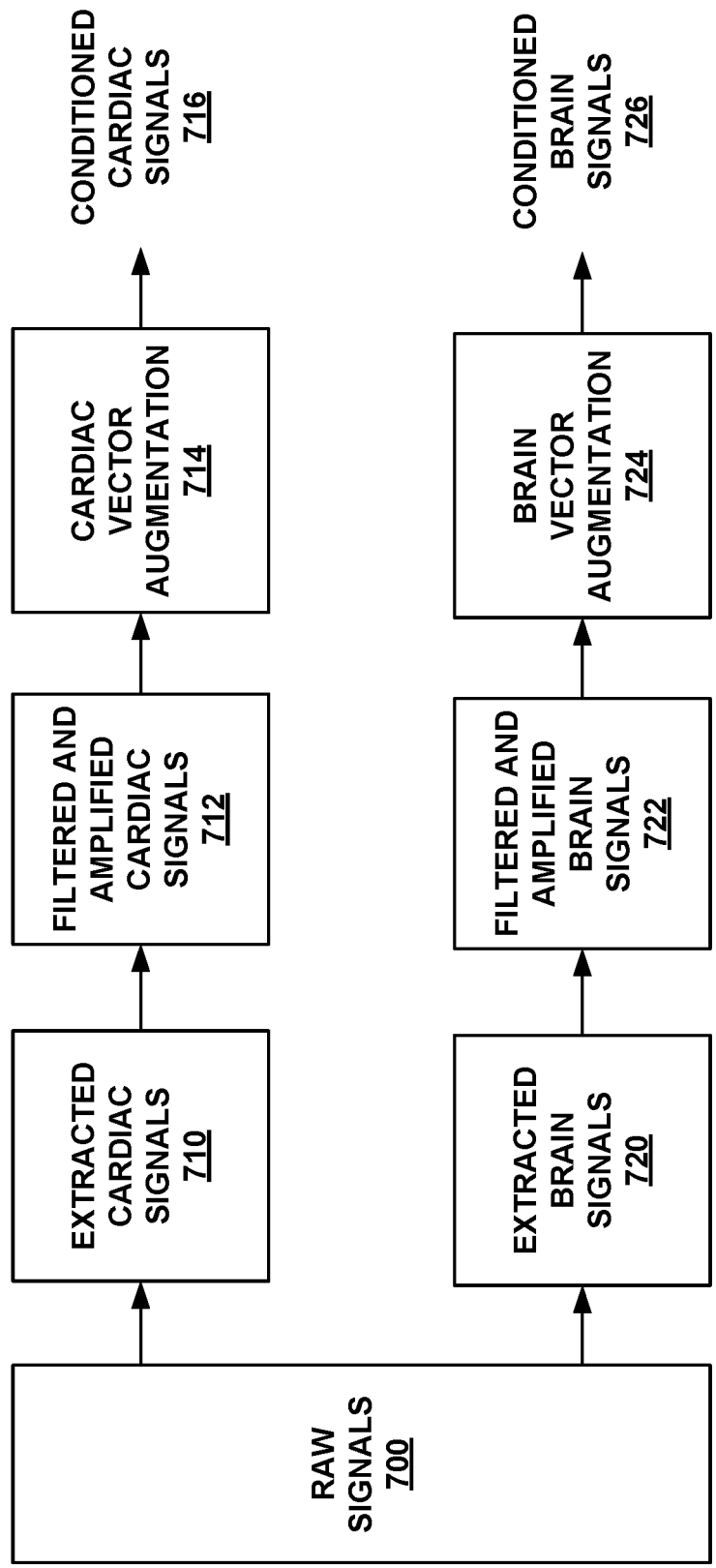
FIG. 7 is a block diagram of signal pre-conditioning for raw cardiac and brain signals.

FIG. 7 is a block diagram of signal pre-conditioning for raw cardiac and brain signals 700. Raw signals 700 include the raw cardiac and brain signals along with noise received by a pair of electrodes. Additionally or alternatively, raw signals 700 may include any brain signal and any cardiac or heart signal (e.g., a cardiac mechanical signal). For example, raw signals 700 may include a pulse pressure wave that corresponds to heart contractions. A cardiac mechanical signal or a pulse pressure wave can be sensed by monitoring the ECG (e.g., because the pulse affects the ECG), through the impedance change caused by fluid flow, by the mechanical effect on the electrodes, through optical sensing (e.g., changes in reflectivity of the particular wavelength of light), accelerometer detection (e.g., ballistic cardiogram). In some examples, one or more of raw signals 700 are surrogates for EEG signals or ECG signals. Pulsatile signals sensed from the scalp vasculature may correspond to ventricular contractions/ECG R-waves with a slight timing delay.

An optical pulse signal (e.g., a photoplethysmographic signal) can be used as a timing base for ensemble averaging or other means of incorporating heart rate information to improve the signal-to-noise ratio for a cardiac signal. The optical pulse signal can therefore be used to derive a surrogate cardiac signal, which may be particularly useful when the cardiac signal has poor quality. A first or second derivative of an optical pulse signal can be used as a trigger for ensemble averaging by, for example, determining the time associated with a maximum/minimum value of the first or second derivative and/or a zero-crossing of the first or second derivative. Sharp, high-frequency points can be used as trigger points to increase the resolution of the ensemble signal, whereas lower-frequency trigger points may smear or distort the ensemble average. The cardiac waveforms that are aligned with the trigger points can be stored and averaged to generate the ensemble signal. The optical signal can also be used to measure high or low blood pressure or local tissue perfusion, any of which can be useful in detecting the presence of a stroke or discriminating between ischemic and hemorrhagic conditions.

Each pair of electrodes may be referred to as a vector or a channel for a differential signal. For example, a sub-scalp implanted cranial device may include at least three electrodes, where raw signal 700 represents a differential signal received across the pair of the electrodes. An ECG signal received at the back-of-head/neck region has a typical amplitude of approximately plus/minus one millivolt or one thousand microvolts. An EEG signal received at the back-of-head/neck region has a typical amplitude of approximately plus/minus one hundred microvolts.

Raw signals 700 received across the pair of electrodes may be split or copied into two processing/filtering pathways. A first copy of raw signals 700 becomes extracted cardiac signals 710, and a second copy of raw signals 700 becomes extracted brain signals 720. Extracted cardiac signals 710 are filtered and amplified to generate signals 712, and extracted brain signals 720 are filtered and amplified to generate signals 722. The filtering may include bandpass filtering based on the frequency ranges shown below in Table I. The filtering may be digital or analog and may occur in the time domain or the frequency domain. Conditioned cardiac signals 716 are generated by performing cardiac vector augmentation 714, and conditioned cardiac signals 726 are generated by performing cardiac vector augmentation 724. Vector augmentation may include signal augmentation techniques such as addition, multiplication, division, and/or performing ratio operations. Vector augmentation may be performed to combine signal vectors using these vector operations. Although not shown in Table I, a filter with a passband from about 1.5 Hz to about 2 Hz or from about 1.5 Hz to about 3 Hz can be used to extract pulse artifacts.

TABLE I

Typical ECG and EEG signal sampling and sense amplifier specifications

| Parameter | ECG signal value | EEG signal value |
| --- | --- | --- |
| Sampling rate | 256 Hz | 250 Hz |
| Sampling resolution | 16 bits/sample | |
| Bandwidth | 0.5-95 Hz | 0.05-100 Hz, or 0.05-150 Hz |
| Amplifier gain | | up to 250 Hz |
| Range | +/−11.3 mV | 0-400 µV |
| Compressed stored waveform sample rate | 128 Hz | |
| Symptomatic episode duration | 30 minutes configurable/ 1 minute post-storage | |

Figure 8:
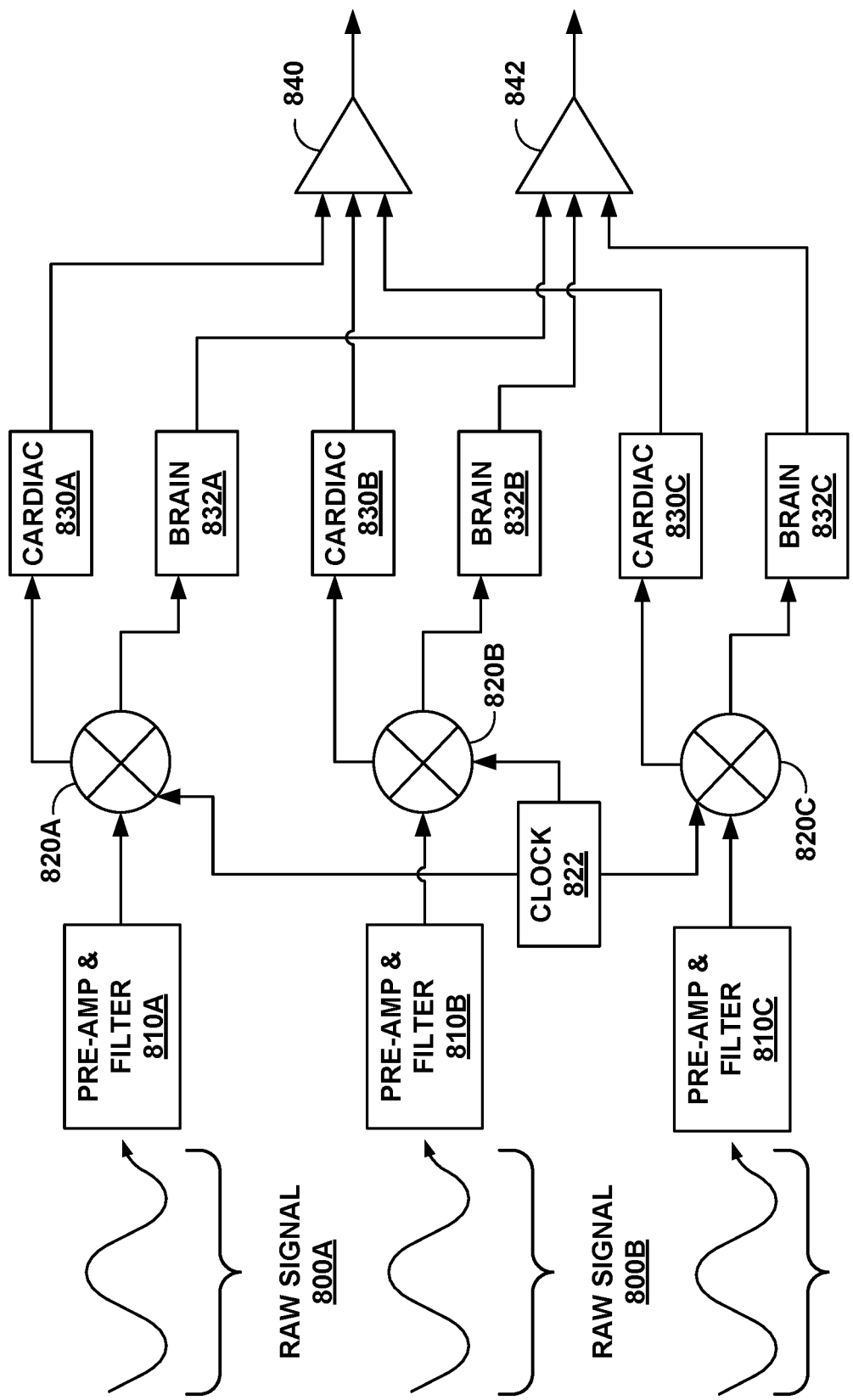
FIG. 8 is a block diagram of circuitry for generating composite cardiac and brain signals.

FIG. 8 is a block diagram of circuitry for generating composite cardiac and brain signals. The circuitry shown in FIG. 8 includes three vectors or channels received by pre-amplifier and filter circuitry 810A-810C. Each of the vectors may represent a pair of electrodes, such that each of raw signals 800A-800C is a differential signal received across a respective pair of electrodes. Although not shown in FIG. 8, a switch (electrical or mechanical) or other circuitry may be configured to generate raw differential signal 800A by subtracting or taking the difference of the amplitudes received at two electrodes.

In some examples, a device may be configured to generate a virtual signal representing a differential signal across a pair of electrodes. For example, a device may include circuitry for generating raw signal 800A by subtracting the amplitude of a signal received at a first electrode from the amplitude of a signal received at a second electrode. The circuitry may also be configured to generate raw signal 800B by subtracting the amplitude of a signal received at the second electrode from the amplitude of a signal received at a third electrode. The circuitry may be configured to then generate raw signal 800C as a virtual signal by subtracting raw signal 800A from raw signal 800B, rather than by subtracting the amplitudes at two electrodes. The generation of a virtual signal may involve simpler circuitry, as compared to generating a differential signal from the amplitudes at two electrodes.

The circuitry shown in FIG. 8 may include entirely analog circuitry or partially or entirely digital circuitry. For example, the circuitry may include analog-to-digital converters (ADCs) between pre-amplifiers and filters 810A-810B and multiplexers 820A-820C or at the input of pre-amplifiers and filters 810A-810B. Alternatively, the circuitry may include an ADC to convert the output of summation blocks 840 and 842 to digital representations (e.g., a digitized signal). The circuitry shown in FIG. 8 may be entirely inside of an IMD, an externally mountable device, a wearable device, an external device in communication with one of these devices, a remote computing device, and/or distributed across any number of these devices.

Pre-amplifiers and filters 810A-810B may be configured to bandpass-filter or low-pass-filter raw signals 800A-800C to generate filtered signals. The passbands of filters 810A-810B may be based on the frequency ranges shown in Table I above. In some examples, the passbands may have an upper limit that is lower than 100 Hertz because the higher frequencies may include less useful or less valuable information about the cardiac and brain signals. After filtering, pre-amplifiers and filters 810A-810B may amplify the filtered signals.

Multiplexers 820A-820C may be configured to split or copy the signals received from pre-amplifiers and filters 810A-810B based on a shared clock signal received from clock 822. Although described as multiplexers, multiplexers 820A-820C may include any circuitry for splitting or copying an input signal, such as a splitter, a coupler, a transistor network, a single-pole double-throw switch, a register for storing the value of a digitized input signal, and/or any other element for splitting or copying an input signal. Clock 822 may synchronize the three channels shown in FIG. 8 by generating a shared clock signals. Thus, each of the channels may have a shared time reference, which can allow summation blocks 840 and 842 to add three synchronized signals.

Figure 9:
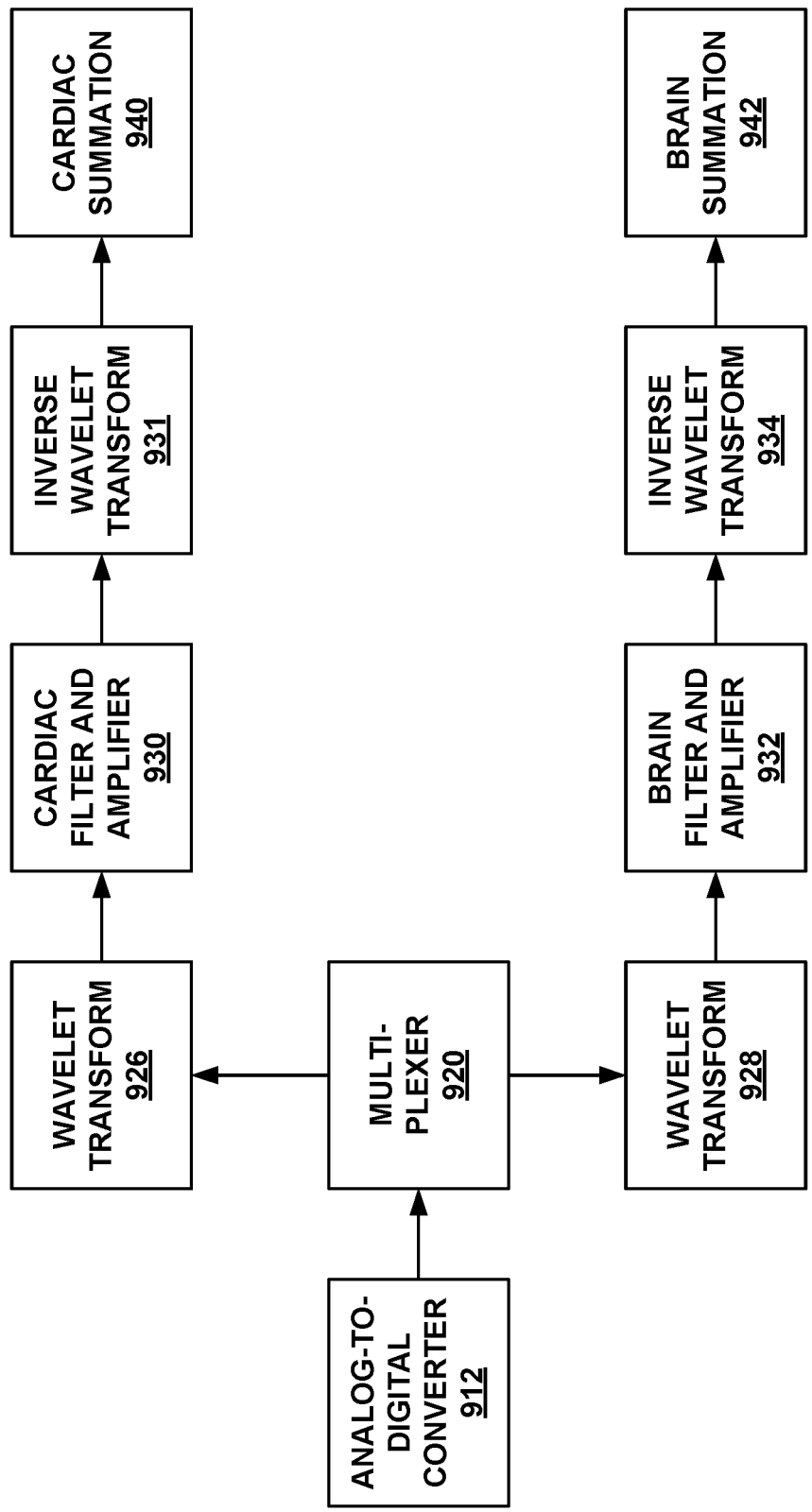
FIG. 9 is a block diagram of circuitry for generating cardiac and brain signals using a wavelet transforms.
Figure 10A:
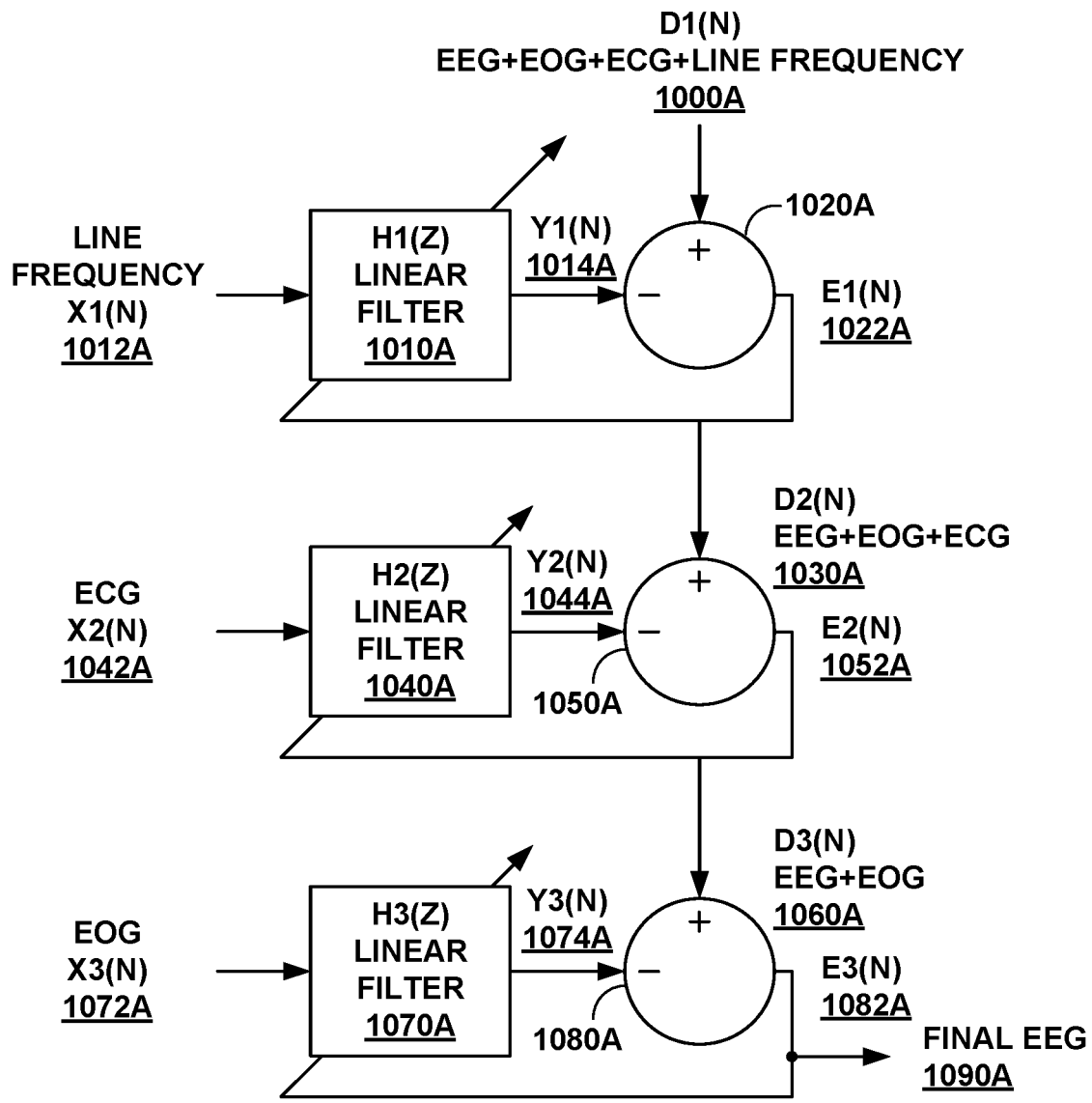
FIGS. 10A and 10B are block diagrams of adaptive filters.
Figure 10B:
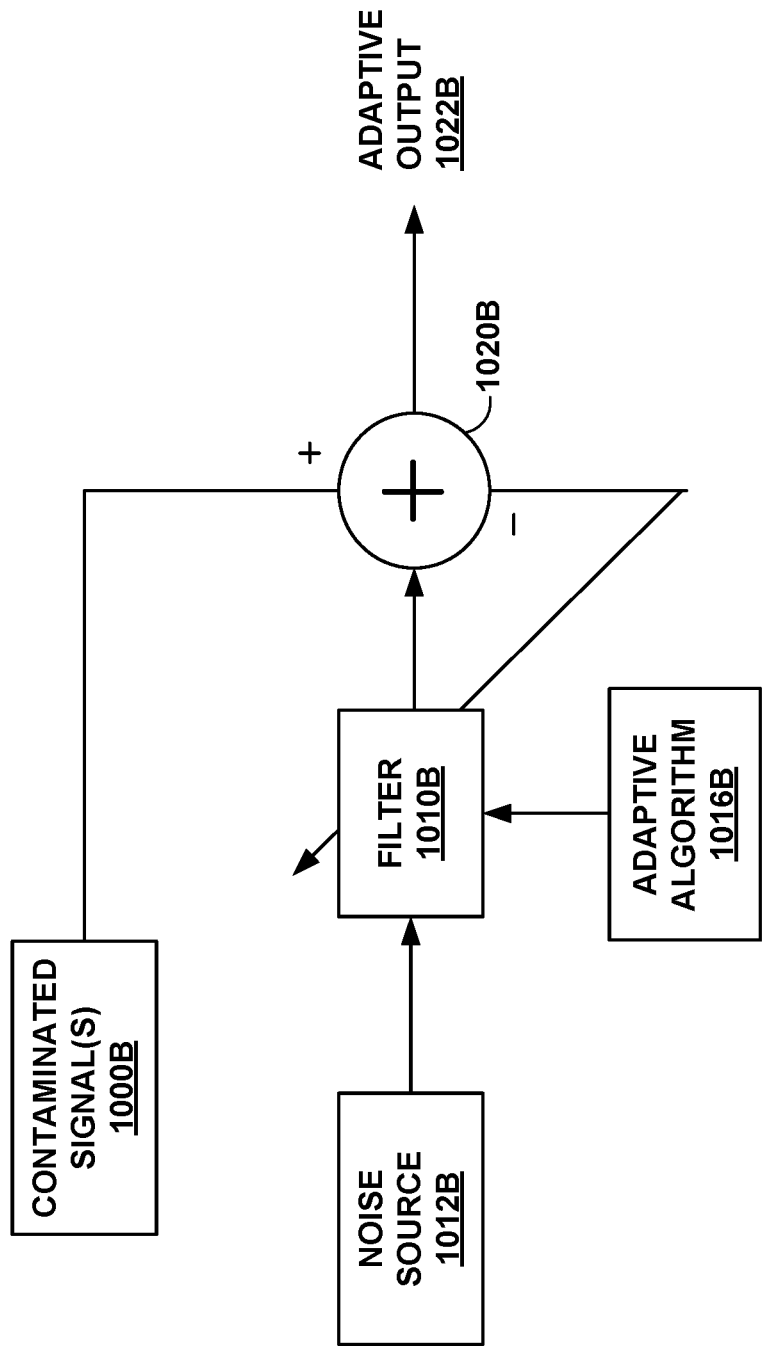

Filters 830A-830C and 832A-832C may include high-pass filters, low-pass filters, and/or amplifiers for generating cardiac and brain signals, respectively. Example circuits and processing techniques for generating cardiac and brain signals are shown in FIGS. 9, 10A, and 10B. The generated cardiac and brain signals are routed summation blocks 840 and 842, which may be configured to generate composite cardiac and brain signals. Summation blocks 840 and 842 may be configured to sum, average, perform scaled addition, and/or otherwise combine the cardiac and brain signals generated by filters 830A-830C and 832A-832C. By generating a composite signal, the signal-to-noise ratio may increase, for example, through direct addition. The composite cardiac and brain signals may be digitized signal (e.g., digital number values). The composite cardiac signal, for example, may include a representation of the R wave, which is the portion of a cardiac signal with the highest amplitude.

FIG. 9 is a block diagram of circuitry for generating cardiac and brain signals using a wavelet transforms. In the example shown in FIG. 9, the input signal is converted to a digitized signal by ADC 912 before multiplexer 920 splits or copies the digitized signal. At blocks 926 and 928, circuitry performs wavelet transform or any other time-to-frequency transform (e.g., Fast Fourier Transform) to generate frequency information for the digitize signals. For example, at blocks 926 and 928, the circuitry may be configured to decompose the digitized signals into different subspaces for noise, cardiac signal, and brain signal. Additionally or alternatively, the circuitry may be configured to use principal components, wavelets, and/or independent component analysis, which is a type of blind source separation (BSS) to decompose the signals into distinct components. Filter and amplifier blocks 930 and 932 may be configured to filter the wavelet-transformed signals to remove frequencies outside of desired frequency ranges before amplifying the filtered signals. Using a classification technique, noise and other artifacts can be zeroed out or ignored. At blocks 931 and 934, the circuitry may be configured to perform an inverse wavelet transform to create clean, reconstructed cardiac and brain signals before generating composite signals at blocks 940 and 942.

An example of a BSS algorithm can expand from using a single channel to using multiple signals with a non-stationary or maximum overlap wavelet transform or empirical mode decomposition. In this algorithm, independent component analysis can be applied to each transformed signal. The components of the transformed signal can be classified as noise, cardiac signal, or brain signal and separated from each other, with noise components being discarded. cardiac and brain components can be separated and inverse transformed generating clear cardiac and brain signals, respectively. Additional example details of BSS algorithms are described in "Separation of Sources From Single-Channel EEG Signals Using Independent Component Analysis" by Maddirala et al., published in IEEE Transactions on Instrumentation and Measurement in 2018, the entire contents of which are incorporated herein by reference.

Additionally or alternatively, where two or more sensed channels are available, multiple virtual signals can be constructed by projecting the sensed signals in different directions in space. In the case of two real channels, virtual signals can be created by projection on to degree increments, for example. Independent component analysis can be applied to each virtual vector. The resulting components are then classified as noise, cardiac signal, or brain signal and separated from each, with noise components being discarded. cardiac and brain components separated and inverse transformed generating clear cardiac and brain signals, respectively. Additional example details of generating virtual signals are described in commonly assigned U.S. Pat. No. 6,505,067, entitled "System and Method for Deriving a Virtual ECG or EGM Signal," issued on Jan. 7, 2003, the entire contents of which are incorporated herein by reference.

Additionally or alternatively, circuitry of this disclosure may be configured to use machine-learning techniques and/or artificial intelligence to generate cardiac and brain signals. For example, the circuitry may be configured to implement machine-learning techniques to update the coefficients in a digital filter or in another algorithm. The machine-learning techniques may include frequency-based approaches, wavelet processing approaches, adaptive signal processing approaches, and/or artificial-intelligence-based approaches to generate cardiac and brain signals based on sensed differential signals.

FIGS. 10A and 10B are block diagrams of adaptive filters for removing noise from an input signal. FIG. 10A depicts a cascade of adaptive filters, where the first adaptive filter receives primary signal 1000A and secondary signal 1012A. Linear filter 1010A is configured to generate output 1014A, which is subtracted from primary signal 1000A at adder block 1020A to generate error signal 1022A. The adaptive filter may be configured to minimize error signal 1022A to remove the artifacts (e.g., line frequency from mains power or fluorescent lights) from primary signal 1000A. Error signal 1022A becomes primary signal 1030A for the second adaptive filter, which removes ECG signal 1042A or another cardiac signal, which can be a real or artificial ECG signal. Output 1044A of linear filter 1040A represents a good estimate of the ECG artifacts present in the EEG record or in the record of another brain signal. At adder block 1050A, output 1044A is subtracted from primary signal 1030A to generate error signal 1052A, which becomes primary signal 1060A for the third adaptive filter, which removes electrooculography (EOG) signal 1072A, which can be a real or artificial EOG signal. Output 1074A of linear filter 1070A can be a replica of the EOG artifacts present in the EEG record. At adder block 1080A, output 1074A is subtracted from primary signal 1060A to generate error signal 1082A, which becomes final EEG signal 1090A without artifacts.

Adaptive filtering techniques can use a reference signal correlated with an artifact as shown in FIGS. 10A and 10B. There are also adaptive filtering techniques that do not use a separate reference artifact signal but instead use a trigger signal (reference impulse) when the artifact occurs and/or coordinated with the occurrence of the artifact. This is possible in the case where R waves are detectable in the signals, but the signals contain EEG as well. The objective of an adaptive recurrent filtering technique is to adapt filter coefficients, or weights, so that the impulse response of the desired signal is acquired. The reference signal can be an impulse coincident in time with the first sample of the signal complex. Each recurrence of the signal complex results in a new reference impulse and a new update of all the filter weights. Circuitry can obtain the desired impulse response by minimizing the mean squared error between the primary and the reference inputs.

For an adaptive recurrent filter, at each time step, circuitry adapts only one filter weight. All the filter weights are adapted once each recurring cycle. To implement the adaptive recurrent filter, circuitry can identify a reference impulse train coincident with the QRS complexes, or detection of peaks is a signal indicative of mechanical activity of the heart. The reference impulse is located in such a manner that the filter weights span the entire QRS-T complex. This identification may be accomplished by placing the impulse at the very beginning of the QRS complex. When a pacemaker is being used, the circuitry can obtain the reference impulse sequence by detecting the pacemaker spike. For non-paced rhythms, QRS detection is a common first step in arrhythmia detection algorithms and can be carried out in hardware. The reference impulse is coincident with each occurrence of the QRS complex. Circuitry may be configured to select the actual filter weights so as to span the entire QRS complex.

The adaptive filter shown in FIG. 10B illustrates the concept of noise cancellation with input signals 1000B and 1012B. Contaminated signal 1000B includes both noise and the desired source signal. Filter 1010B using adaptive algorithm 1016B filters the noise source 1012B, and adder block 1020B subtracts the filtered noise from the contaminated signal 1000B to generate adaptive output 1022B. A processed ECG signal may be used for noise source 1012B to generate an brain signal using adaptive output 1022B. Additional example details of adaptive filters are described in "Adaptive Filtering Applications," by Correa et al., published in 2011, and "ECG Artifact Removal of EEG Signal Using Adaptive Neural Network," by Routray et al., published in 2018, the entire contents of which are incorporated herein by reference.

Figure 11:
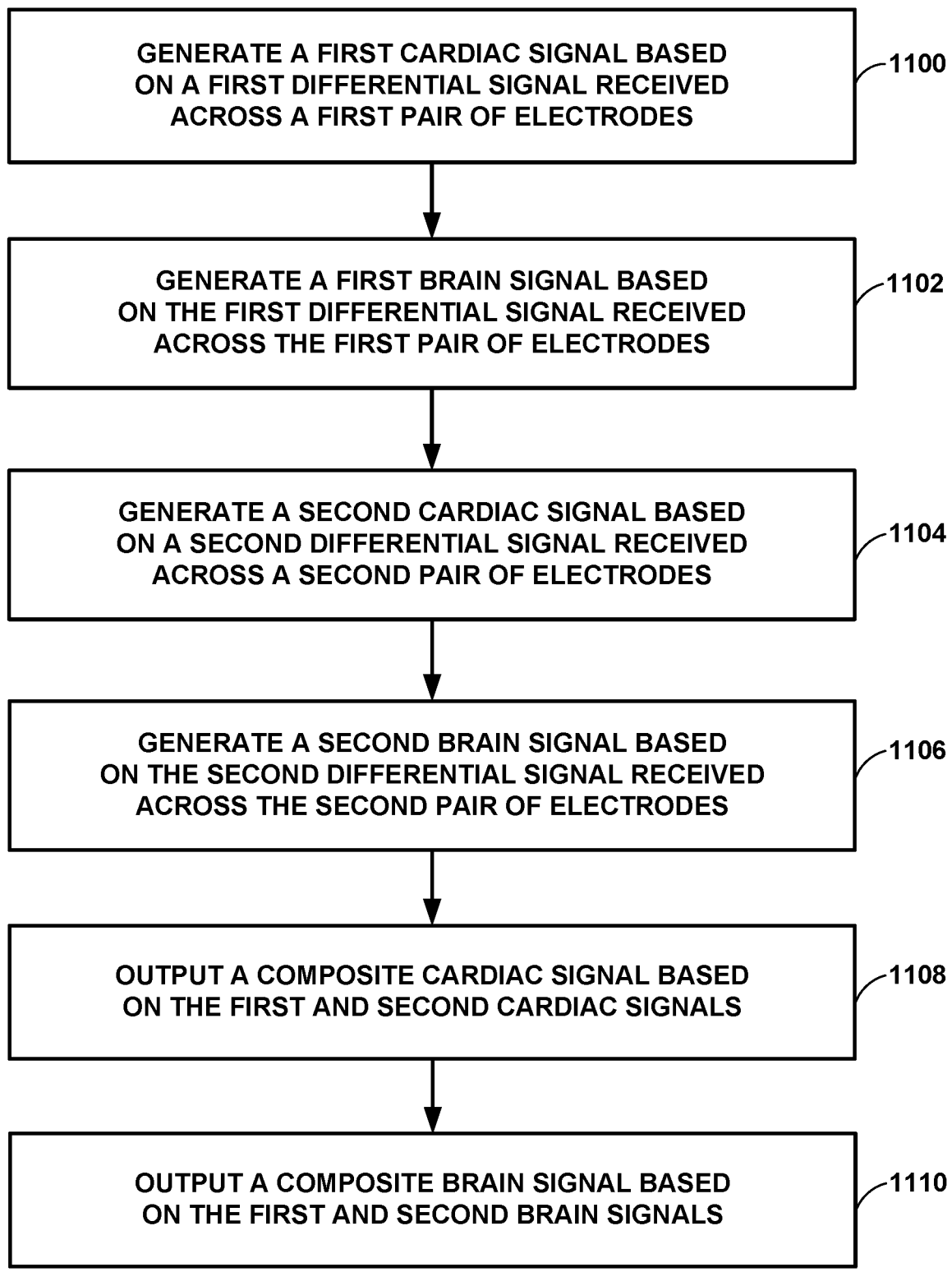
FIG. 11 is a flow diagram of an example technique for generating composite cardiac and brain signals.

FIG. 11 is a flow diagram of an example technique for generating composite cardiac and brain signals. The circuitry shown in FIG. 8 will be described as performing the techniques of example FIG. 11, but other components, devices, and systems (e.g., sensor device 106 or sensor devices 210, 220, or 230) may perform similar functionality in other examples.

As shown in the example of FIG. 11, filter 830A generates a first cardiac signal based on a first raw differential signal 800A received across a first pair of electrodes (1100). Filter 832A generates a first brain signal based on the first raw differential signal 800A received across the first pair (1102). Filter 830B generates a second cardiac signal based on a second raw differential signal 800B received across a second pair of electrodes (1104). Filter 832B generates a second brain signal based on the second raw differential signal 800B received across the second pair (1106). Filters 830A, 830B, 832A, and 832B can use analog filter circuitry and/or digital filters to generate the cardiac and brain signals. Additionally or alternatively, filters 830A, 830B, 832A, and 832B may be configured to convert the differential signals to the frequency domain before filtering.

Summation block 840 outputs a composite cardiac signal based on the first and second cardiac signals received from filters 830A and 830B (1108). Summation block 842 outputs a composite brain signal based on the first and second brain signals received from filters 832A and 832B (1110). Summation blocks 840 and 842 may be configured to generate the composite signals by summing, averaging, and/or performing scaled addition. Although not shown in FIG. 8, post-processing may include comparing high-noise data to population data via a machine-learning algorithm and updating for real-time processing to reduce noise rejection.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques could be fully implemented in one or more circuits or logic elements. The techniques of this disclosure may be implemented in a wide variety of devices or apparatuses, including sensor device, an IMD, an external programmer, a combination of a sensor device and external programmer, an integrated circuit (IC) or a set of ICs, and/or discrete electrical circuitry, residing in a sensor device and/or external programmer.

Example 1

A device includes at least three electrodes including a first pair of electrodes and a second pair of electrodes; circuitry configured to: generate a first cardiac signal based on a first differential signal received across the first pair; generate a first brain signal based on the first differential signal received across the first pair; generate a second cardiac signal based on a second differential signal received across the second pair; generate a second brain signal based on the second differential signal received across the second pair; output a composite cardiac signal based on the first cardiac signal and the second cardiac signal; and output a composite brain signal based on the first brain signal and the second brain signal.

Example 2

A device includes at least three segmented electrodes including: a first segmented electrode including a first portion and a second portion; a second segmented electrode including a third portion and a fourth portion; and a third segmented electrode including a fifth portion and a sixth portion; and circuitry configured to: generate a first cardiac signal based on a first differential signal received across the first portion and the third portion; generate a first brain signal based on the first differential signal received across the second portion and the fourth portion; generate a second cardiac signal based on a second differential signal received across the first portion and the fifth portion; generate a second brain signal based on the second differential signal received across the second portion and the sixth portion; output a composite cardiac signal based on the first cardiac signal and the second cardiac signal; and output a composite brain signal based on the first brain signal and the second brain signal.

Example 3

The device of the preceding examples or any combination thereof, wherein the first cardiac signal includes an electrocardiogram signal.

Example 4

The device of the preceding examples or any combination thereof, wherein the first cardiac signal includes a pressure pulse signal.

Example 5

The device of the preceding examples or any combination thereof, wherein the first brain signal includes an electroencephalogram signal.

Example 6

The device of the preceding examples or any combination thereof, wherein the at least three electrodes include a first electrode, a second electrode, a third electrode, and a fourth electrode.

Example 7

The device of the preceding examples or any combination thereof, wherein the fourth electrode is positioned on an opposite surface of a housing of the device from the first, second, and third electrodes.

Example 8

The device of the preceding examples or any combination thereof, further including a housing and a lead extending from the housing.

Example 9

The device of the preceding examples or any combination thereof, wherein the lead is configured to be attached to a skull of a patient.

Example 10

The device of the preceding examples or any combination thereof, wherein a first electrode of the at least three electrodes is positioned on the lead.

Example 11

The device of the preceding examples or any combination thereof, further including a second lead extending from a housing of the device.

Example 12

The device of the preceding examples or any combination thereof, wherein the second lead is configured to be attached to a skull of a patient.

Example 13

The device of the preceding examples or any combination thereof, wherein a second electrode of the at least three electrodes is positioned on the second lead.

Example 14

The device of the preceding examples or any combination thereof, wherein the at least three electrodes further includes a third pair of electrodes configured to receive a third differential signal.

Example 15

The device of the preceding examples or any combination thereof, wherein the circuitry is further configured to generate a third cardiac signal based on the third differential signal received across the third pair.

Example 16

The device of the preceding examples or any combination thereof, wherein the circuitry is further configured to generate a third brain signal based on the third differential signal received across the third pair.

Example 17

The device of the preceding examples or any combination thereof, wherein the circuitry is configured to output the composite cardiac signal based on the first, second, and third cardiac signals.

Example 18

The device of the preceding examples or any combination thereof, wherein the circuitry is configured to output the composite brain signal based on the first, second, and third brain signals.

Example 19

The device of the preceding examples or any combination thereof, wherein the circuitry is configured to receive the first differential signal as a first raw signal from the first pair.

Example 20

The device of the preceding examples or any combination thereof, wherein the circuitry is configured to receive the second differential signal as a second raw signal from the second pair.

Example 21

The device of the preceding examples or any combination thereof, wherein the circuitry is further configured to generate a third differential signal as a virtual signal based on the first raw signal and the second raw signal.

Example 22

The device of the preceding examples or any combination thereof, wherein the circuitry is further configured to generate a third cardiac signal based on the third differential signal.

Example 23

The device of the preceding examples or any combination thereof, wherein the circuitry is further configured to generate a third brain signal based on the third differential signal.

Example 24

The device of the preceding examples or any combination thereof, wherein the at least three electrodes includes a segmented electrode.

Example 25

The device of the preceding examples or any combination thereof, wherein the segmented electrode includes a first electrode portion separated form a second electrode portion by an insulative material.

Example 26

The device of the preceding examples or any combination thereof, wherein the circuitry is configured to generate the first cardiac signal based on a first raw signal received by the first portion of the segmented electrode, and wherein the circuitry is configured to generate the first brain signal based on a second raw signal received by the second portion of the segmented electrode.

Example 27

The device of the preceding examples or any combination thereof, wherein the circuitry is configured to output the composite cardiac signal by summing the first cardiac signal and the second cardiac signal.

Example 28

The device of the preceding examples or any combination thereof, wherein the circuitry is configured to output the composite cardiac signal by averaging the first cardiac signal and the second cardiac signal.

Example 29

The device of the preceding examples or any combination thereof, wherein the circuitry is configured to generate the first brain signal by filtering the first differential signal using an adaptive filter.

Example 30

The device of the preceding examples or any combination thereof, wherein the circuitry is configured to generate the first brain signal by filtering the first differential signal using a cascade of adaptive filters.

Example 31

The device of the preceding examples or any combination thereof, wherein the circuitry is configured to generate the first brain signal using a processed cardiac signal to characterize a noise source.

Example 32

The device of the preceding examples or any combination thereof, wherein the circuitry is configured to generate the first brain signal using a trigger signal coordinated with an occurrence of an artifact.

Example 33

The device of the preceding examples or any combination thereof, wherein the circuitry is configured to filter the first differential signal to generate a first filtered signal.

Example 34

The device of the preceding examples or any combination thereof, wherein the circuitry is configured to generate the first cardiac based on the first filtered signal.

Example 35

The device of the preceding examples or any combination thereof, wherein the circuitry is configured to generate the first brain based on the first filtered signal.

Example 36

The device of the preceding examples or any combination thereof, wherein the circuitry includes a splitter configured to: deliver a first copy of the first differential signal to cardiac generation circuitry; and deliver a second copy of the first differential signal to brain generation circuitry.

Example 37

The device of the preceding examples or any combination thereof, wherein the circuitry includes a multiplexer configured to: deliver a first copy of the first differential signal to cardiac generation circuitry; and deliver a second copy of the first differential signal to brain generation circuitry.

Example 38

The device of the preceding examples or any combination thereof, wherein the circuitry includes a transistor network configured to: deliver a first copy of the first differential signal to cardiac generation circuitry; and deliver a second copy of the first differential signal to brain generation circuitry.

Example 39

The device of the preceding examples or any combination thereof, wherein the circuitry is configured to generate first cardiac signal by performing a wavelet transform on the first differential signal.

Example 40

The device of the preceding examples or any combination thereof, wherein the circuitry is configured to generate first brain signal by performing a wavelet transform on the first differential signal.

Example 41

The device of the preceding examples or any combination thereof, wherein the circuitry is configured to generate first cardiac signal by filtering a wavelet-transformed version of the first differential signal.

Example 42

The device of the preceding examples or any combination thereof, wherein the circuitry is configured to generate first brain signal by filtering a wavelet-transformed version of the first differential signal.

Example 43

The device of the preceding examples or any combination thereof, wherein the circuitry is configured to inverse-wavelet-transform the first cardiac signal before generating the composite cardiac signal.

Example 44

The device of the preceding examples or any combination thereof, wherein the circuitry is configured to inverse-wavelet-transform the first brain signal before generating the composite brain signal.

Example 45

The device of the preceding examples or any combination thereof, wherein the device includes an implantable medical device configured to be implanted in a patient.

Example 46

The device of the preceding examples or any combination thereof, wherein the device includes an external patch device configured to be attached to a patient.

Example 47

The device of the preceding examples or any combination thereof, further including a housing carrying the at least three electrodes and containing the circuitry.

Example 48

The device of the preceding examples or any combination thereof, wherein the at least three electrodes are configured to detect brain activity data corresponding to activity in at least one of a P3, Pz, or P4 brain region.

Example 49

The device of the preceding examples or any combination thereof, wherein the device is configured to be disposed at or adjacent a rear portion of a neck or skull of a patient or on the temple(s) of the patient.

Example 50

The device of the preceding examples or any combination thereof, wherein the device is configured to be implanted within a patient.

Example 51

The device of the preceding examples or any combination thereof, wherein the device is configured to be implanted subcutaneously.

Example 52

The device of the preceding examples or any combination thereof, wherein the housing is configured to be disposed on an external surface of skin of a patient.

Example 53

The device of the preceding examples or any combination thereof, wherein the circuitry is configured to determine that a patient has had a stroke based on the composite cardiac signal and the composite brain signal.

Example 54

The device of the preceding examples or any combination thereof, wherein the circuitry is configured to determine that a patient has had a seizure based on the composite cardiac signal and the composite brain signal.

Example 55

The device of the preceding examples or any combination thereof, wherein the circuitry is configured to determine that a patient has had a seizure based on the composite cardiac signal and the composite brain signal.

Example 56

The device of the preceding examples or any combination thereof, wherein the first differential signal includes a digitized signal.

Example 57

The device of the preceding examples or any combination thereof, wherein the first cardiac signal includes a digital number.

Example 58

The device of the preceding examples or any combination thereof, wherein the composite cardiac signal includes a digital number.

Example 59

The device of the preceding examples or any combination thereof, further including a shared clock configured to generate a clock signal for multiple channels.

Example 60

The device of the preceding examples or any combination thereof, wherein the circuitry is configured to generate the first cardiac signal based on the clock signal.

Example 61

The device of the preceding examples or any combination thereof, wherein the circuitry is configured to generate the second cardiac signal based on the clock signal.

Example 62

The device of the preceding examples or any combination thereof, wherein the circuitry is configured to receive a sensed signal from a supplementary electrode on the device.

Example 63

The device of the preceding examples or any combination thereof, wherein the supplementary electrode is positioned on an opposite of a housing of the device from the at least three electrodes.

Example 64

The device of the preceding examples or any combination thereof, wherein the circuitry is configured to receive a sensed signal from a supplementary electrode on a wearable device or an external patch device.

Example 65

The device of the preceding examples or any combination thereof, wherein the circuitry is configured to subtract the sensed signal from the first differential signal and/or second differential signal.

Example 66

The device of the preceding examples or any combination thereof, wherein the circuitry is configured to generate the first brain signal based on a wavelet-based machine learning algorithm, a frequency-based machine learning algorithm, an adaptive-signal-processing-based machine learning algorithm, and/or an artificial-intelligence-based machine learning algorithm.

Example 67

The device of the preceding examples or any combination thereof, wherein a housing of the device has a triangular shape.

Example 68

The device of the preceding examples or any combination thereof, wherein a housing of the device has a boomerang shape.

Example 69

The device of the preceding examples or any combination thereof, wherein a housing of the device has a rectangular shape.

Example 70

The device of the preceding examples or any combination thereof, wherein first and second electrodes of the at least three electrodes are positioned at opposing ends of a housing of the device.

Example 71

The device of the preceding examples or any combination thereof, wherein a third electrode of the at least three electrodes is positioned at a midpoint of a housing of the device.

Example 72

The device of the preceding examples or any combination thereof, wherein first, second, and third electrodes of the at least three electrodes are positioned at vertices of a triangular-shaped housing or a boomerang-shaped housing of the device.

Example 73

The device of the preceding examples or any combination thereof, wherein to generate the first cardiac signal, the circuitry is configured to generate an ensemble-averaged signal using a pulse signal received by the optical sensor as a timing base.

Example 74

The device of the preceding examples or any combination thereof, wherein to generate the second cardiac signal, the circuitry is configured to generate an ensemble-averaged signal using a pulse signal received by the optical sensor as a timing base.

Example 75

The device of the preceding examples or any combination thereof, wherein to generate the first cardiac signal, the circuitry is configured to generate an ensemble-averaged signal based on an electrocardiogram signal.

Example 76

The device of the preceding examples or any combination thereof, wherein to generate the second cardiac signal, the circuitry is configured to generate an ensemble-averaged signal based on an electrocardiogram signal.

Example 77

A method includes generating a first cardiac signal based on a first differential signal received across a first pair of electrodes; generating a first brain signal based on the first differential signal received across the first pair; generating a second cardiac signal based on a second differential signal received across a second pair of electrodes; generating a second brain signal based on the second differential signal received across the second pair; outputting a composite cardiac signal based on the first cardiac signal and the second cardiac signal; and outputting a composite brain signal based on the first brain signal and the second brain signal.

Example 78

The method of example 77, further including the techniques performed by the device of examples 1-76 or any combination thereof.

Example 79

A system includes means for performing the techniques performed by the device of examples 1-76 or any combination thereof.

Example 80

A medical device system includes more than one device including circuitry configured to perform the techniques performed by the device of examples 1-76 or any combination thereof.

Example 81

A device includes a computer-readable medium having executable instructions stored thereon, configured to be executable by processing circuitry for causing the processing circuitry to perform the techniques performed by the device of examples 1-76 or any combination thereof

What is claimed is:

1. A device comprising:
    a housing configured to be subcutaneously implanted at a portion of a neck or a head of a patient;
    at least three electrodes comprising a first pair of electrodes configured to sense a first differential signal and a second pair of electrodes configured to sense a second differential signal, the at least three electrodes positioned on the housing;
    circuitry configured to:
        generate a first cardiac signal based on the first differential signal sensed via the first pair;
        generate a first brain signal based on the first differential signal sensed via the first pair;
        generate a second cardiac signal based on the second differential signal sensed via the second pair;
        generate a second brain signal based on the second differential signal sensed via the second pair;
        output a composite cardiac signal based on the first cardiac signal and the second cardiac signal; and
        output a composite brain signal based on the first brain signal and the second brain signal,
        wherein the first cardiac signal comprises a first electrocardiogram (ECG) signal, the second cardiac signal comprises a second ECG signal, the first brain signal comprises a first electroencephalogram (EEG) signal, and the second brain signal comprises a second EEG signal.

2. The device of claim 1, further comprising an optical sensor,
    wherein to generate the first cardiac signal, the circuitry is configured to generate, based on the first ECG signal, an ensemble-averaged signal using a pulse signal received by the optical sensor as a timing base.

3. The device of claim 1,
    wherein the at least three electrodes further comprises a third pair of electrodes configured to sense a third differential signal,
    wherein the circuitry is further configured to generate a third cardiac signal based on the third differential signal sensed via the third pair,
    wherein the circuitry is further configured to generate a third brain signal based on the third differential signal sensed via the third pair,
    wherein the circuitry is configured to output the composite cardiac signal based on the first, second, and third cardiac signals, and
    wherein the circuitry is configured to output the composite brain signal based on the first, second, and third brain signals.

4. The device of claim 1,
    wherein the circuitry is configured to receive the first differential signal as a first raw signal from the first pair,
    wherein the circuitry is configured to receive the second differential signal as a second raw signal from the second pair,
    wherein the circuitry is further configured to generate a third differential signal as a virtual signal based on the first raw signal and the second raw signal,
    wherein the circuitry is further configured to generate a third cardiac signal based on the third differential signal,
    wherein the circuitry is further configured to generate a third brain signal based on the third differential signal,
    wherein the circuitry is configured to output the composite cardiac signal based on the first, second, and third cardiac signals, and
    wherein the circuitry is configured to output the composite brain signal based on the first, second, and third brain signals.

5. The device of claim 1, wherein the circuitry is configured to output the composite cardiac signal by at least:
    summing the first cardiac signal and the second cardiac signal; or
    averaging the first cardiac signal and the second cardiac signal.

6. The device of claim 1,
    wherein the circuitry is configured to generate the first brain signal by at least filtering the first differential signal using a cascade of adaptive filters,
    wherein the circuitry is configured to generate the first brain signal using a processed cardiac signal to characterize a noise source, and
    wherein the circuitry is configured to generate the first brain signal using a trigger signal coordinated with an occurrence of an artifact.

7. The device of claim 1,
    wherein the circuitry is configured to filter the first differential signal to generate a first filtered signal,
    wherein the circuitry is configured to generate the first cardiac signal based on the first filtered signal, and
    wherein the circuitry is configured to generate the first brain signal based on the first filtered signal.

8. The device of claim 1, wherein the circuitry comprises a splitter configured to:
    deliver a first copy of the first differential signal to generate the first cardiac signal; and
    deliver a second copy of the first differential signal to generate the first brain signal,
    wherein the splitter comprises a multiplexer or a transistor network.

9. The device of claim 1,
    wherein the circuitry is configured to generate the first cardiac signal by at least:
        performing a wavelet transform on the first differential signal;
        filtering a first wavelet-transformed version of the first differential signal; and
        inverse-wavelet-transforming the first wavelet-transformed version before generating the composite cardiac signal, and
    wherein the circuitry is configured to generate the first brain signal by at least:
        performing a wavelet transform on the first differential signal;
        filtering a second wavelet-transformed version of the first differential signal; and
        inverse-wavelet-transforming the second wavelet-transformed version before generating the composite brain signal.

10. The device of claim 1, wherein the device is configured to be disposed at or adjacent a rear portion of a neck or skull of a patient or at a temporal location of the patient.

11. The device of claim 1, wherein the circuitry is configured to determine that a patient has had a stroke or a seizure based on the composite cardiac signal and the composite brain signal.

12. The device of claim 1, further comprising a shared clock configured to generate a clock signal for multiple channels,
    wherein the circuitry is configured to generate the first cardiac signal based on the clock signal, and
    wherein the circuitry is configured to generate the second cardiac signal based on the clock signal.

13. The device of claim 1,
wherein the at least three electrodes include a first electrode, a second electrode, a third electrode, and a fourth electrode, and
wherein the fourth electrode is positioned on an opposite surface of the housing of the device from the first, second, and third electrodes.

14. The device of claim 1, wherein the housing is a triangular-shaped housing or a boomerang-shaped housing, and wherein first, second, and third electrodes of the at least three electrodes are positioned at vertices of the triangular-shaped housing or the boomerang-shaped housing.

15. A device comprising:
a housing configured to be subcutaneously implanted at a portion of a neck or a head of a patient;
at least three segmented electrodes positioned on the housing, the at least three segmented electrodes comprising:
a first segmented electrode including a first portion and a second portion;
a second segmented electrode including a third portion and a fourth portion; and
a third segmented electrode including a fifth portion and a sixth portion; and
circuitry configured to:
generate a first cardiac signal based on a first differential signal received across the first portion and the third portion;
generate a first brain signal based on a second differential signal received across the second portion and the fourth portion;
generate a second cardiac signal based on a third differential signal received across the first portion and the fifth portion;
generate a second brain signal based on a fourth differential signal received across the second portion and the sixth portion;
output a composite cardiac signal based on the first cardiac signal and the second cardiac signal; and
output a composite brain signal based on the first brain signal and the second brain signal.

16. The device of claim 15, further comprising an insulative material separating the first portion of the first segmented electrode from the second portion of the first segmented electrode.

17. The device of claim 15, wherein the circuitry is configured to:
generate a third cardiac signal based on a fifth differential signal received across the third portion and the fifth portion;
generate a third brain signal based on a sixth differential signal received across the fourth portion and the sixth portion;
output the composite cardiac signal based on the first, second, and third cardiac signals; and
output the composite brain signal based on the first, second, and third brain signals.

18. The device of claim 15, wherein the at least three segmented electrodes further include a fourth segmented electrode positioned on an opposite surface of the housing of the device from the first, second, and third segmented electrodes.

19. The device of claim 15,
wherein the circuitry is configured to generate the first cardiac signal based on a first raw signal received by at least the first portion of the segmented electrode, and
wherein the circuitry is configured to generate the first brain signal based on a second raw signal received by at least the second portion of the segmented electrode.

20. A method for operating processing circuitry of a computing device comprising:
generating, by the processing circuitry of the computing device, a first cardiac signal based on a first differential signal sensed via a first pair of electrodes disposed on a housing of a sensor device subcutaneously disposed at a portion of a neck or skull of the patient;
generating, by the processing circuitry of the computing device, a first brain signal based on the first differential signal sensed via the first pair;
generating, by the processing circuitry of the computing device, a second cardiac signal based on a second differential signal sensed via a second pair of electrodes disposed on the housing of the sensor device;
generating, by the processing circuitry of the computing device, a second brain signal based on the second differential signal sensed via the second pair;
outputting a composite cardiac signal based on the first cardiac signal and the second cardiac signal; and
outputting a composite brain signal based on the first brain signal and the second brain signal,
wherein the first cardiac signal comprises a first electrocardiogram (ECG) signal, the second cardiac signal comprises a second ECG signal, the first brain signal comprises a first electroencephalogram (EEG) signal, and the second brain signal comprises a second EEG signal.

* * * * *